United States Patent
Knight et al.

(10) Patent No.: US 10,604,531 B2
(45) Date of Patent: Mar. 31, 2020

(54) ENHANCER OF ZESTE HOMOLOG 2 INHIBITORS

(71) Applicant: GLAXOSMITHKLINE INTELLECTUAL PROPERTY (NO.2) LIMITED, Brentford, Middlesex (GB)

(72) Inventors: Steven David Knight, Collegeville, PA (US); Louis Vincent Lafrance, III, Collegeville, PA (US); Xinrong Tian, Collegeville, PA (US)

(73) Assignee: GLAXOSMITHKLINE INTELLECTUAL PROPERTY (NO.2) LIMITED, Brentford, Middlesex (GB)

( * ) Notice: Subject to any disclaimer, the term of this patent is extended or adjusted under 35 U.S.C. 154(b) by 0 days.

(21) Appl. No.: 16/097,322

(22) PCT Filed: May 1, 2017

(86) PCT No.: PCT/IB2017/052523
§ 371 (c)(1),
(2) Date: Oct. 29, 2018

(87) PCT Pub. No.: WO2017/191545
PCT Pub. Date: Nov. 9, 2017

(65) Prior Publication Data
US 2019/0092785 A1 Mar. 28, 2019

Related U.S. Application Data

(60) Provisional application No. 62/482,964, filed on Apr. 7, 2017, provisional application No. 62/454,143, filed on Feb. 3, 2017, provisional application No. 62/359,904, filed on Jul. 8, 2016, provisional application No. 62/332,131, filed on May 5, 2016.

(51) Int. Cl.
*C07D 495/04* (2006.01)

(52) U.S. Cl.
CPC .................. *C07D 495/04* (2013.01)

(58) Field of Classification Search
CPC .................................. C07D 495/04
See application file for complete search history.

(56) References Cited

U.S. PATENT DOCUMENTS

| 8,410,088 | B2 | 4/2013 | Kuntz et al. |
| 9,505,745 | B2 | 11/2016 | Blackledge, Jr. et al. |
| 9,527,837 | B2 | 12/2016 | Yu et al. |
| 9,562,041 | B2 | 2/2017 | Burgess et al. |
| 9,718,838 | B2 | 8/2017 | Guo et al. |
| 9,790,212 | B2 | 10/2017 | Blackledge, Jr. et al. |
| 9,956,210 | B2 | 5/2018 | Burgess et al. |
| 2012/0264734 | A1 | 10/2012 | Kuntz et al. |
| 2014/0179667 | A1 | 6/2014 | Edwards et al. |
| 2015/0126522 | A1 | 5/2015 | Burgess et al. |
| 2015/0361067 | A1 | 12/2015 | Collins et al. |
| 2018/0265517 | A1 | 9/2018 | Marx et al. |

FOREIGN PATENT DOCUMENTS

| WO | WO 2014/097041 A1 | 6/2014 |
| WO | WO 2014/177982 A1 | 11/2014 |
| WO | WO 2016/066697 A1 | 5/2016 |
| WO | WO 2017/035060 A1 | 3/2017 |

OTHER PUBLICATIONS

Lund. Leukemia, 2014, 28, 44-49. (Year: 2014).*
"Prevention-Prostate Cancer Foundation", http://www.pcf.org/site/c.leJRIROrEpH/b.5802029/k.31EA/Prevention.htm, accessed Apr. 18, 2016. (Year: 2016).*

* cited by examiner

*Primary Examiner* — Noble E Jarrell
(74) *Attorney, Agent, or Firm* — Duke M. Fitch; Edward R. Gimmi

(57) ABSTRACT

This invention relates to novel compounds according to Formula (I) which are inhibitors of Enhancer of Zeste Homolog 2 (EZH2), to pharmaceutical compositions containing them, to processes for their preparation, and to their use in therapy for the treatment of cancers.

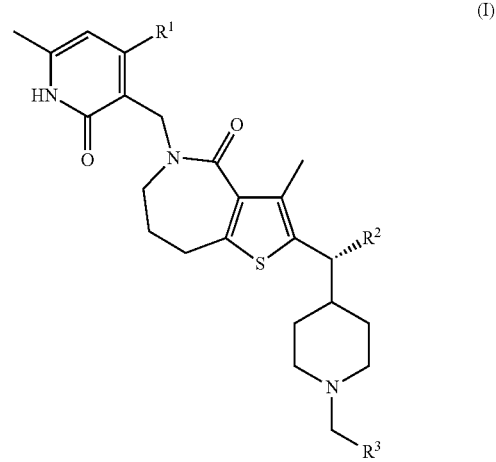

16 Claims, 8 Drawing Sheets

ENHANCER OF ZESTE HOMOLOG 2 INHIBITORS

This application is a § 371 of International Application No. PCT/IB2017/052523, filed 1 May 2017, which claims priority of U.S. Provisional Application Nos. 62/482,964, filed 7 Apr. 2017; 62/454,143, filed 3 Feb. 2017; 62/359,904, filed 8 Jul. 2016; and 62/332,131, filed 5 May 2016.

FIELD OF THE INVENTION

This invention relates to compounds which inhibit Enhancer of Zeste Homolog 2 (EZH2) and thus are useful for inhibiting the proliferation of and/or inducing apoptosis in cancer cells.

BACKGROUND OF THE INVENTION

Epigenetic modifications play an important role in the regulation of many cellular processes including cell proliferation, differentiation, and cell survival. Global epigenetic modifications are common in cancer, and include global changes in DNA and/or histone methylation, dysregulation of non-coding RNAs and nucleosome remodeling leading to aberrant activation or inactivation of oncogenes, tumor suppressors and signaling pathways. However, unlike genetic mutations which arise in cancer, these epigenetic changes can be reversed through selective inhibition of the enzymes involved. Several methylases involved in histone or DNA methylation are known to be dysregulated in cancer. Thus, selective inhibitors of particular methylases will be useful in the treatment of proliferative diseases such as cancer.

EZH2 (human EZH2 gene: Cardoso, C, et al; *European J of Human Genetics*, Vol. 8, No. 3 Pages 174-180, 2000) is the catalytic subunit of the Polycomb Repressor Complex 2 (PRC2) which functions to silence target genes by tri-methylating lysine 27 of histone H3 (H3K27me3). Histone H3 is one of the five main histone proteins involved in the structure of chromatin in eukaryotic cells. Featuring a main globular domain and a long N-terminal tail, Histones are involved with the structure of the nucleosomes, a 'beads on a string' structure. Histone proteins are highly post-translationally modified however Histone H3 is the most extensively modified of the five histones. The term "Histone H3" alone is purposely ambiguous in that it does not distinguish between sequence variants or modification state. Histone H3 is an important protein in the emerging field of epigenetics, where its sequence variants and variable modification states are thought to play a role in the dynamic and long term regulation of genes.

Increased EZH2 expression has been observed in numerous solid tumors including those of the prostate, breast, skin, bladder, liver, pancreas, head and neck and correlates with cancer aggressiveness, metastasis and poor outcome (Varambally et al. *Nature* 419:624-629, 2002; Kleer et al. *Proc Natl Acad Sci USA* 100:11606-11611, 2003; Breuer et al. *Neoplasia* 6:736-743, 2004; Bachmann et al. *Prostate* 65:252-259, 2005; Weikert et al. *Int. J. Mol. Med.* 16:349-353, 2005; Sudo et al. *British Journal of Cancer* 92:1754-1758, 2005; Bachmann et al. *Journal of Clinical Oncology* 24:268-273, 2006). For instance, there is a greater risk of recurrence after prostatectomy in tumors expressing high levels of EZH2, increased metastasis, shorter disease-free survival and increased death in breast cancer patients with high EZH2 levels (Varambally et al. *Nature* 419:624-629, 2002; Kleer et al. *Proc Natl Acad Sci USA* 100:11606-11611, 2003). More recently, inactivating mutations in UTX (ubiquitously transcribed tetratricopeptide repeats X), a H3K27 demethylase which functions in opposition to EZH2, have been identified in multiple solid and hematological tumor types (including renal, glioblastoma, esophageal, breast, colon, non-small cell lung, small cell lung, bladder, multiple myeloma, and chronic myeloid leukemia tumors), and low UTX levels correlate with poor survival in breast cancer suggesting that loss of UTX function leads to increased H3K27me3 and repression of target genes (Wang et al. *Genes & Development* 24:327-332, 2010). Together, these data suggest that increased H3K27me3 levels contribute to cancer aggressiveness in many tumor types and that inhibition of EZH2 activity may provide therapeutic benefit.

Numerous studies have reported that direct knockdown of EZH2 via siRNA or shRNA or indirect loss of EZH2 via treatment with the SAH hydrolase inhibitor 3-deazaneplanocin A (DZNep) decreases cancer cell line proliferation and invasion in vitro and tumor growth in vivo (Gonzalez et al., 2008, GBM 2009). While the precise mechanism by which aberrant EZH2 activity leads to cancer progression is not known, many EZH2 target genes are tumor suppressors suggesting that loss of tumor suppressor function is a key mechanism. In addition, EZH2 overexpression in immortalized or primary epithelial cells promotes anchorage independent growth and invasion and requires EZH2 catalytic activity (Kleer et al. *Proc Natl Acad Sci USA* 100:11606-11611, 2003; Cao et al. *Oncogene* 27:7274-7284, 2008).

Thus, there is strong evidence to suggest that inhibition of EZH2 activity decreases cellular proliferation and invasion. Accordingly, compounds that inhibit EZH2 activity would be useful for the treatment of cancer.

Latent human immunodeficiency virus (HIV) proviruses are silenced as the result of deacetylation and methylation of histones located at the viral long terminal repeat (LTR). Chromatin immunoprecipitation experiments using latently infected Jurkat T-cell lines demonstrated that EZH2 was present at high levels at the LTR of silenced HIV proviruses and was rapidly displaced following proviral reactivation. Knockdown of EZH2 induced up to 40% of the latent HIV proviruses. Knockdown of EZH2 also sensitized latent proviruses to external stimuli, such as T-cell receptor stimulation, and slowed the reversion of reactivated proviruses to latency. Similarly, cell populations that responded poorly to external stimuli carried HIV proviruses that were enriched in H3K27me3 and relatively depleted in H3K9me3. These findings suggest that PRC2-mediated silencing is an important feature of HIV latency and that inhibitors of histone methylation may play a useful role in induction strategies designed to eradicate latent HIV pools (Friedman et al. *J. Virol.* 85: 9078-9089, 2011). Additional studies have shown that H3K27 demethylation at the proviral promoter sensitizes latent HIV to the effects of vorinostat in ex vivo cultures of resting $CD4^+$ T cells (Tripathy et al. *J. Virol.* 89: 8392-8405, 2015).

SUMMARY OF THE INVENTION

The present invention relates to compounds according to Formula (I) or pharmaceutically acceptable salts thereof:

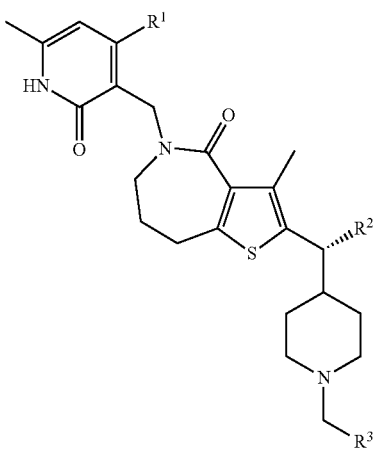

(I)

wherein:
R¹ is $(C_1-C_4)$alkyl or $(C_1-C_4)$alkoxy;
R² is $(C_1-C_3)$alkyl; and
R³ is $(C_1-C_5)$alkyl, halo$(C_1-C_5)$alkyl, hydroxy$(C_1-C_5)$ alkyl, $(C_1-C_4)$alkoxy$(C_1-C_8)$alkyl-, $(C_3-C_5)$cycloalkyl, or $(C_6-C_{10})$bicycloalkyl, wherein said $(C_3-C_5)$cycloalkyl or $(C_6-C_{10})$bicycloalkyl are each optionally substituted by one or two groups independently selected from halogen, hydroxyl, $(C_1-C_4)$alkoxy, $(C_1-C_4)$alkyl, and halo$(C_1-C_4)$ alkyl.

Another aspect of this invention relates to a method of inducing apoptosis in cancer cells of solid tumors; treating solid tumor cancers.

Another aspect of the invention relates to pharmaceutical preparations comprising compounds of Formula (I) and pharmaceutically acceptable excipients.

In another aspect, there is provided the use of a compound of Formula (I) or a pharmaceutically acceptable salt or solvate thereof, in the manufacture of a medicament for use in the treatment of a disorder mediated by EZH2, such as by inducing apoptosis in cancer cells.

In another aspect, this invention provides for the use of a compound of Formula (I) or a pharmaceutically acceptable salt thereof for the treatment of diseases mediated by EZH2. The invention further provides for the use of a compound of Formula (I) or a pharmaceutically acceptable salt thereof as an active therapeutic substance in the treatment of a disease mediated by EZH2.

In another aspect, the invention provides a compound of Formula (I) or a pharmaceutically acceptable salt thereof for use in therapy.

In another aspect, there is provided a compound of Formula (I) or a pharmaceutically acceptable salt thereof for use in the treatment of a disorder mediated by EZH2.

In another aspect, there is provided a compound of Formula (I) or a pharmaceutically acceptable salt thereof for use in the treatment of cellular proliferation diseases.

In another aspect, there is provided a compound of Formula (I) or a pharmaceutically acceptable salt thereof for use in the treatment of cancer, including the treatment of solid tumors, for example brain cancer (gliomas), glioblastomas, leukemias, lymphomas, Bannayan-Zonana syndrome, Cowden disease, Lhermitte-Duclos disease, breast cancer, inflammatory breast cancer, Wilm's tumor, Ewing's sarcoma, Rhabdomyosarcoma, ependymoma, medulloblastoma, colon cancer, gastric cancer, bladder cancer, head and neck cancer, kidney cancer, lung cancer, liver cancer, melanoma, renal cancer, ovarian cancer, pancreatic cancer, prostate cancer, sarcoma cancer, osteosarcoma cancer, giant cell tumor of bone, and thyroid cancer. In another aspect, there is provided a compound of Formula (I) or a pharmaceutically acceptable salt thereof for use in the treatment of a hematologic cancer, for example acute myeloid leukemia, chronic myeloid leukemia, acute lymphoblastic leukemia, chronic lymphocytic leukemia, myeloproliferative diseases, multiple myeloma, myelodysplastic syndrome, Hodgkin's disease, and non-Hodgkin's lymphoma, in particular a non-Hodgkin's lymphoma, for example diffuse large B-cell lymphoma (DLBCL) and follicular lymphoma.

In another aspect there is provided methods of co-administering the presently invented compounds of Formula (I) with other active ingredients.

In another aspect there is provided a combination of a compound of Formula (I) or a pharmaceutically acceptable salt thereof and at least one anti-neoplastic agent for use in the treatment of a disorder mediated by EZH2.

In another aspect there is provided a combination of a compound of Formula (I) or a pharmaceutically acceptable salt thereof and at least one anti-neoplastic agent for use in the treatment of cellular proliferation diseases.

In another aspect there is provided a combination of a compound of Formula (I) or a pharmaceutically acceptable salt thereof and at least one anti-neoplastic agent for use in the treatment of cancer, including the treatment of solid tumors, for example brain cancer (gliomas), glioblastomas, leukemias, lymphomas, Bannayan-Zonana syndrome, Cowden disease, Lhermitte-Duclos disease, breast cancer, inflammatory breast cancer, Wilm's tumor, Ewing's sarcoma, Rhabdomyosarcoma, ependymoma, medulloblastoma, colon cancer, gastric cancer, bladder cancer, head and neck cancer, kidney cancer, lung cancer, liver cancer, melanoma, renal cancer, ovarian cancer, pancreatic cancer, prostate cancer, sarcoma cancer, osteosarcoma cancer, giant cell tumor of bone, and thyroid cancer. In another aspect, there is provided a combination of a compound of Formula (I) or a pharmaceutically acceptable salt thereof and at least one anti-neoplastic agent for use in the treatment of a hematologic cancer, for example acute myeloid leukemia, chronic myeloid leukemia, acute lymphoblastic leukemia, chronic lymphocytic leukemia, myeloproliferative diseases, multiple myeloma, myelodysplastic syndrome, Hodgkin's disease, and non-Hodgkin's lymphoma, in particular a non-Hodgkin's lymphoma, for example diffuse large B-cell lymphoma (DLBCL) and follicular lymphoma.

DETAILED DESCRIPTION OF THE INVENTION

Figure 1:
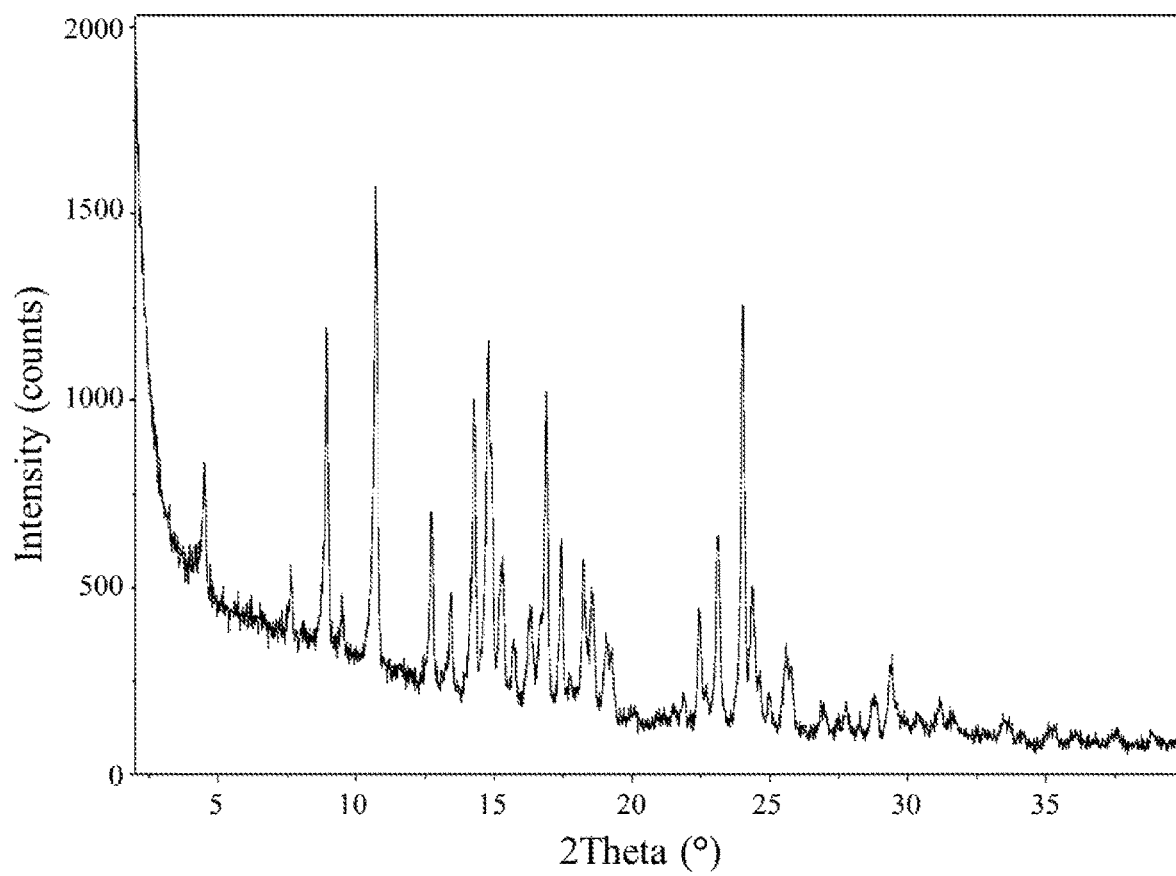
FIG. 1 shows an X-ray powder diffraction pattern of the hydrochloric acid salt of the compound of Example 1 (Form II).

This invention relates to compounds of the Formula (I) as defined above or pharmaceutically acceptable salts thereof.

In one embodiment, this invention relates to compounds of Formula (I) wherein $R^1$ is $(C_1-C_4)$alkyl or $(C_1-C_4)$alkoxy. In another embodiment, this invention relates to compounds of Formula (I) wherein $R^1$ is $(C_1-C_4)$alkyl. In another embodiment, this invention relates to compounds of Formula (I) wherein $R^1$ is methyl, ethyl, n-propyl, or methoxy. In another embodiment, this invention relates to compounds of Formula (I) wherein $R^1$ is methyl or methoxy. In a specific embodiment, this invention relates to compounds of Formula (I) wherein $R^1$ is methyl.

In one embodiment, this invention relates to compounds of Formula (I) wherein $R^2$ is $(C_1-C_3)$alkyl. In another embodiment, this invention relates to compounds of Formula (I) wherein $R^2$ is methyl, ethyl, n-propyl, or isopropyl. In another embodiment, this invention relates to compounds of Formula (I) wherein $R^2$ is methyl or ethyl. In a specific embodiment, this invention relates to compounds of Formula (I) wherein $R^2$ is methyl.

In one embodiment, this invention relates to compounds of Formula (I) wherein $R^3$ is $(C_1-C_5)$alkyl, halo$(C_1-C_5)$alkyl, hydroxy$(C_1-C_5)$alkyl, $(C_1-C_4)$alkoxy$(C_1-C_5)$alkyl-, $(C_3-C_5)$cycloalkyl, or $(C_6-C_{10})$bicycloalkyl, wherein said $(C_3-C_5)$cycloalkyl or $(C_6-C_{10})$bicycloalkyl are each optionally substituted by one or two groups independently selected from halogen, hydroxyl, $(C_1-C_4)$alkoxy, $(C_1-C_4)$alkyl, and halo$(C_1-C_4)$alkyl. In another embodiment, this invention relates to compounds of Formula (I) wherein $R^3$ is $(C_1-C_6)$alkyl, halo$(C_1-C_6)$alkyl, $(C_3-C_5)$cycloalkyl, or $(C_6-C_{10})$bicycloalkyl, wherein said $(C_3-C_5)$cycloalkyl or $(C_6-C_{10})$bicycloalkyl are each optionally substituted by one or two groups independently selected from halogen, hydroxyl, $(C_1-C_4)$alkoxy, $(C_1-C_4)$alkyl, and halo$(C_1-C_4)$alkyl. In another embodiment, this invention relates to compounds of Formula (I) wherein $R^3$ is $(C_1-C_6)$alkyl, halo$(C_1-C_6)$alkyl, $(C_3-C_5)$cycloalkyl, or $(C_6-C_{10})$bicycloalkyl, wherein said $(C_3-C_5)$cycloalkyl or $(C_6-C_{10})$bicycloalkyl are each optionally substituted by one or two groups independently selected from halogen and $(C_1-C_4)$alkyl. In another embodiment, this invention relates to compounds of Formula (I) wherein $R^3$ is $(C_1-C_6)$alkyl, halo$(C_1-C_6)$alkyl, $(C_3-C_5)$cycloalkyl, or $(C_6-C_{10})$bicycloalkyl, wherein said $(C_3-C_5)$cycloalkyl or $(C_6-C_{10})$bicycloalkyl are each optionally substituted by fluoro or methyl. In another embodiment, this invention relates to compounds of Formula (I) wherein $R^3$ is $(C_1-C_6)$alkyl or halo$(C_1-C_6)$alkyl. In another embodiment, this invention relates to compounds of Formula (I) wherein $R^3$ is $(C_1-C_4)$alkyl. In another embodiment, this invention relates to compounds of Formula (I) wherein $R^3$ is tert-butyl. In another embodiment, this invention relates to compounds of Formula (I) wherein $R^3$ is $(C_3-C_5)$cycloalkyl or $(C_6-C_{10})$bicycloalkyl, each of which is optionally substituted by one or two groups independently selected from halogen and $(C_1-C_4)$alkyl. In another embodiment, this invention relates to compounds of Formula (I) wherein $R^3$ is $(C_3-C_5)$cycloalkyl or $(C_6-C_{10})$bicycloalkyl, each of which is optionally substituted by fluoro or methyl. In another embodiment, this invention relates to compounds of Formula (I) wherein $R^3$ is $(C_3-C_5)$cycloalkyl which is optionally substituted by fluoro or methyl. In another embodiment, this invention relates to compounds of Formula (I) wherein $R^3$ is $(C_3-C_5)$cycloalkyl which is optionally substituted by methyl. In another embodiment, this invention relates to compounds of Formula (I) wherein $R^3$ is cyclobutyl which is optionally substituted by methyl.

Specific compounds of this invention include:
(R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one;
(R)-2-(1-(1-(cyclobutylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one;
(R)-5-((4,6-dimethyl-2-oxo-1,2-dihydropyridin-3-yl)methyl)-2-(1-(1-isobutylpiperidin-4-yl)ethyl)-3-methyl-5,6,7,8-tetrahydro-4H-thieno[3,2-c]azepin-4-one;
(R)-2-(1-(1-(cyclopentylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one;
(R)-5-((4,6-dimethyl-2-oxo-1,2-dihydropyridin-3-yl)methyl)-2-(1-(1-(2,2-dimethylbutyl)piperidin-4-yl)ethyl)-3-methyl-5,6,7,8-tetrahydro-4H-thieno[3,2-c]azepin-4-one;
(R)-5-((4,6-dimethyl-2-oxo-1,2-dihydropyridin-3-yl)methyl)-2-(1-(1-(2-fluoro-2-methylpropyl)piperidin-4-yl)ethyl)-3-methyl-5,6,7,8-tetrahydro-4H-thieno[3,2-c]azepin-4-one;
(R)-2-(1-(1-(cyclopropylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one;
(R)-5-((4,6-dimethyl-2-oxo-1,2-dihydropyridin-3-yl)methyl)-3-methyl-2-(1-(1-((1-methylcyclopentyl)methyl)piperidin-4-yl)ethyl)-5,6,7,8-tetrahydro-4H-thieno[3,2-c]azepin-4-one;
(R)-2-(1-(1-(bicyclo[2.2.2]octan-1-ylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one;
(R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one; and
(R)-5-((4,6-dimethyl-2-oxo-1,2-dihydropyridin-3-yl)methyl)-3-methyl-2-(1-(1-((1-methylcyclopropyl)methyl)piperidin-4-yl)ethyl)-5,6,7,8-tetrahydro-4H-thieno[3,2-c]azepin-4-one;
or pharmaceutically acceptable salts thereof.

Typically, but not absolutely, the salts of the present invention are pharmaceutically acceptable salts. Salts of the disclosed compounds containing a basic amine or other basic functional group may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, γ-hydroxybutyrates, glycolates, tartrates mandelates, and sulfonates, such as xylenesulfonates, methanesulfonates, propanesulfonates, naphthalene-1-sulfonates and naphthalene-2-sulfonates.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acid such as lysine and arginine.

Other salts, which are not pharmaceutically acceptable, may be useful in the preparation of compounds of this invention and these should be considered to form a further aspect of the invention. These salts, such as oxalic or trifluoroacetate, while not in themselves pharmaceutically acceptable, may be useful in the preparation of salts useful as intermediates in obtaining the compounds of the invention and their pharmaceutically acceptable salts.

The compound of Formula (I) may exist in a crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that the compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The present invention is further directed to crystalline forms of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one.

In some embodiments, a crystalline form the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by an X-ray powder diffraction (XRPD) pattern comprising at least nine diffraction angles, when measured using Cu $K_\alpha$ radiation, selected from a group consisting of about 4.5, 7.7, 8.9, 9.5, 10.7, 12.7, 13.4, 14.3, 14.8, 14.9, 15.3, 15.7, 16.3, 16.9, 17.4, 18.3, 18.6, 19.1, 21.9, 22.4, 23.1, 24.0, 24.4, 25.0, 25.6, 26.9, 27.7, 28.8, and 29.4 degrees 2θ. In another embodiment, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by an X-ray powder diffraction (XRPD) pattern comprising at least eight diffraction angles or at least seven diffraction angles or at least six diffraction angles or at least five diffraction angles or at least four diffraction angles, when measured using Cu $K_\alpha$ radiation, selected from a group consisting of about 4.5, 7.7, 8.9, 9.5, 10.7, 12.7, 13.4, 14.3, 14.8, 14.9, 15.3, 15.7, 16.3, 16.9, 17.4, 18.3, 18.6, 19.1, 21.9, 22.4, 23.1, 24.0, 24.4, 25.0, 25.6, 26.9, 27.7, 28.8, and 29.4 degrees 2θ. In another embodiment, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by an X-ray powder diffraction (XRPD) pattern comprising at least three diffraction angles, when measured using Cu $K_\alpha$ radiation, selected from a group consisting of about 4.5, 7.7, 8.9, 9.5, 10.7, 12.7, 13.4, 14.3, 14.8, 14.9, 15.3, 15.7, 16.3, 16.9, 17.4, 18.3, 18.6, 19.1, 21.9, 22.4, 23.1, 24.0, 24.4, 25.0, 25.6, 26.9, 27.7, 28.8, and 29.4 degrees 2θ.

In still another embodiment, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by an X-ray powder diffraction (XRPD) pattern comprising diffraction angles, when measured using Cu $K_\alpha$ radiation, of about 8.9, 10.7, 14.3, 14.8, 16.9, and 24.0 degrees 2θ. In yet another embodiment, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by an X-ray powder diffraction (XRPD) pattern substantially in accordance with FIG. 1.

In other embodiments, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by a Raman spectrum comprising at least twelve peaks at positions selected from a group consisting of peaks at about 455, 479, 505, 534, 542, 565, 612, 693, 758, 791, 854, 995, 1047, 1114, 1148, 1209, 1241, 1279, 1315, 1390, 1438, 1473, 1551, 1628, 1655, 2735, 2917, and 2953 cm$^{-1}$. In another embodiment, the hydrochloric acid salt of (R)-5-((4,6-dimethyl-2-oxo-1,2-dihydropyridin-3-yl)methyl)-3-methyl-2-

(1-(1-neopentylpiperidin-4-yl)ethyl)-5,6,7,8-tetrahydro-4H-thieno[3,2-c]azepin-4-one is characterized by a Raman spectrum comprising at least eleven peaks or at least ten peaks or at least nine peaks or at least eight peaks or at least seven peaks at positions selected from a group consisting of peaks at about 455, 479, 505, 534, 542, 565, 612, 693, 758, 791, 854, 995, 1047, 1114, 1148, 1209, 1241, 1279, 1315, 1390, 1438, 1473, 1551, 1628, 1655, 2735, 2917, and 2953 cm$^{-1}$. In another embodiment, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by a Raman spectrum comprising at least six peaks at positions selected from a group consisting of peaks at about 455, 479, 505, 534, 542, 565, 612, 693, 758, 791, 854, 995, 1047, 1114, 1148, 1209, 1241, 1279, 1315, 1390, 1438, 1473, 1551, 1628, 1655, 2735, 2917, and 2953 cm$^{-1}$.

In still another embodiment, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by a Raman spectrum comprising peaks at about 505, 534, 612, 1241, 1315, 1390, 1438, 1473, 1551, 1628, 2917, and 2953 cm$^{-1}$. In yet another embodiment, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by a Raman spectrum substantially in accordance with FIG. 2.

Figure 3:
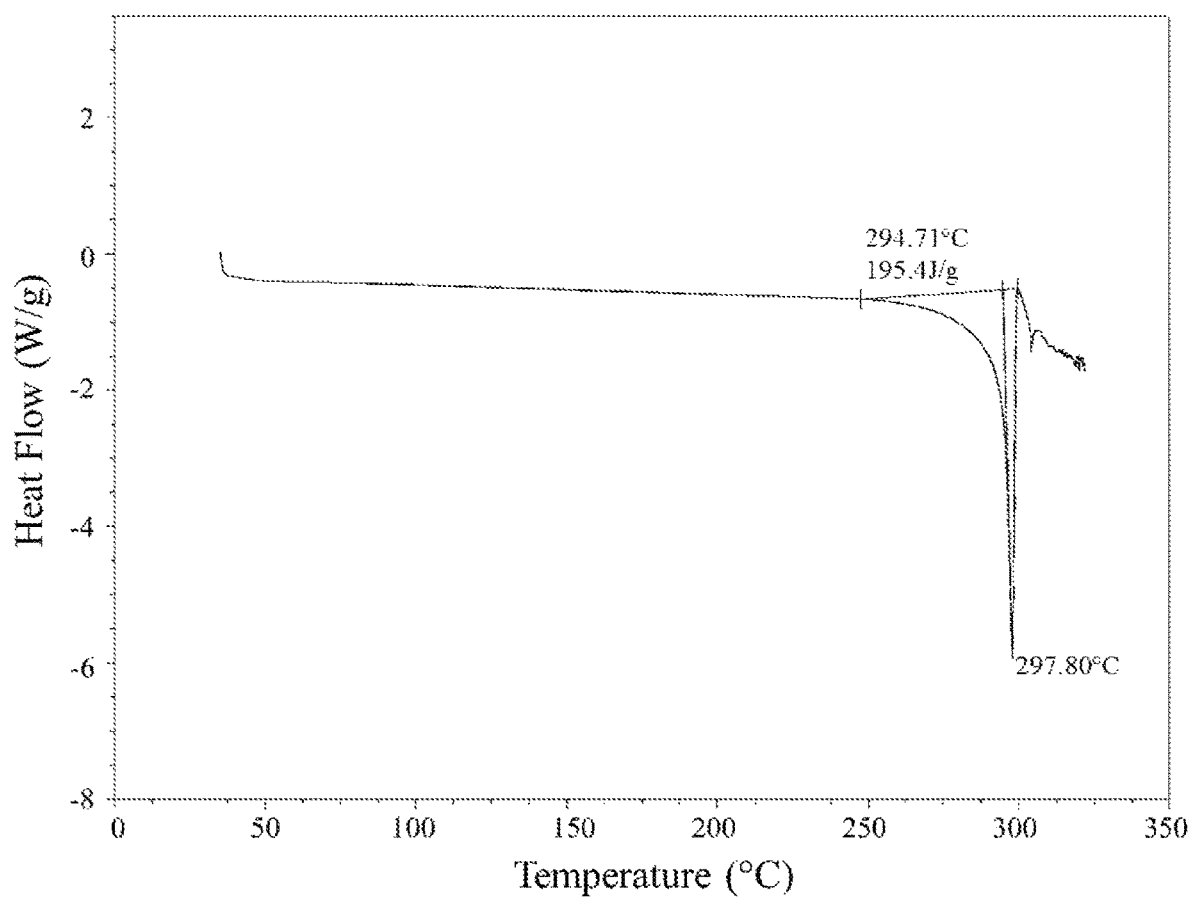
FIG. 3 shows a differential scanning calorimetry trace of the hydrochloric acid salt of the compound of Example 1 (Form II).
Figure 4:
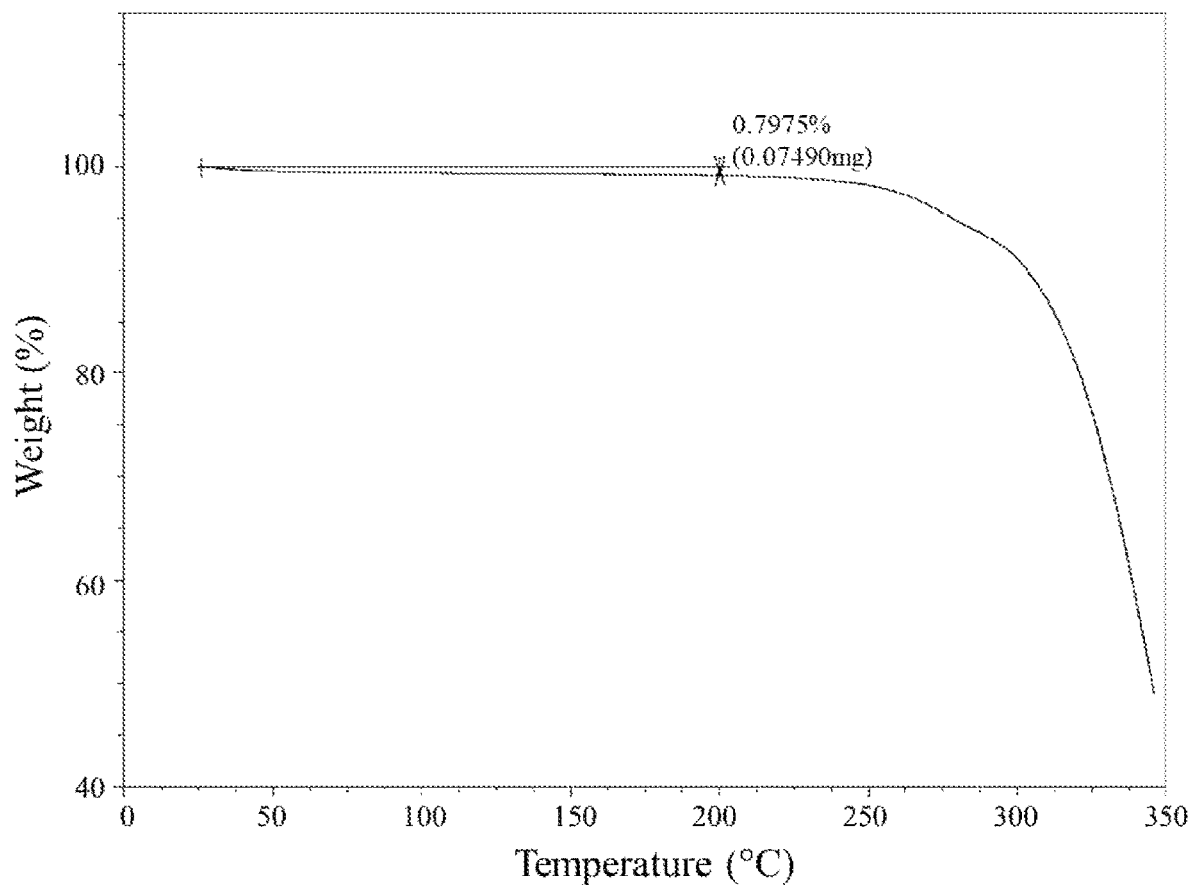
FIG. 4 shows a thermogravimetric analysis trace of the hydrochloric acid salt of the compound of Example 1 (Form II).

In further embodiments, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by a differential scanning calorimetry trace substantially in accordance with FIG. 3 and/or a thermogravimetric analysis trace substantially in accordance with FIG. 4.

In still further embodiments, as a person having ordinary skill in the art will understand, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by any combination of the analytical data characterizing the aforementioned embodiments. For example, in one embodiment, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by an X-ray powder diffraction (XRPD) pattern substantially in accordance with FIG. 1 and a Raman spectrum substantially in accordance with FIG. 2 and a differential scanning calorimetry trace substantially in accordance with FIG. 3 and a thermogravimetric analysis trace substantially in accordance with FIG. 4. In another embodiment, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by an X-ray powder diffraction (XRPD) pattern substantially in accordance with FIG. 1 and a Raman spectrum substantially in accordance with FIG. 2. In another embodiment, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by an X-ray powder diffraction (XRPD) pattern substantially in accordance with FIG. 1 and a differential scanning calorimetry trace substantially in accordance with FIG. 3. In another embodiment, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by an X-ray powder diffraction (XRPD) pattern substantially in accordance with FIG. 1 and a thermogravimetric analysis trace substantially in accordance with FIG. 4. In another embodiment, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by an X-ray powder diffraction (XRPD) pattern comprising diffraction angles, when measured using Cu K$_\alpha$ radiation, of about 8.9, 10.7, 14.3, 14.8, 16.9, and 24.0 degrees 2θ, and a Raman spectrum comprising peaks at about 505, 534, 612, 1241, 1315, 1390, 1438, 1473, 1551, 1628, 2917, and 2953 cm$^{-1}$. In another embodiment, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by an X-ray powder diffraction (XRPD) pattern comprising diffraction angles, when measured using Cu K$_\alpha$ radiation, of about 8.9, 10.7, 14.3, 14.8, 16.9, and 24.0 degrees 2θ, and a differential scanning calorimetry trace substantially in accordance with FIG. 3. In another embodiment, the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is characterized by an X-ray powder diffraction (XRPD) pattern comprising diffraction angles, when measured using Cu K$_\alpha$ radiation, of about 8.9, 10.7, 14.3, 14.8, 16.9, and 2θ degrees 2θ, and a thermogravimetric analysis trace substantially in accordance with FIG. 4.

The present invention is further directed to crystalline forms of the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one.

In some embodiments, a crystalline form the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by an X-ray powder diffraction (XRPD) pattern comprising at least nine diffraction angles, when measured using Cu K$_\alpha$ radiation, selected from a group consisting of about 8.1, 10.2, 11.2, 12.4, 12.8, 13.8, 15.3, 15.5, 16.0, 17.2, 18.3, 18.8, 19.4, 19.8, 20.6, 22.4, 23.8, 24.4, 24.9, 25.6, 26.4, and 27.4 degrees 2θ. In another embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by an X-ray powder diffraction (XRPD) pattern comprising at least eight diffraction angles or at least seven diffraction angles or at least six diffraction angles or at least five diffraction angles or at least four diffraction angles, when measured using Cu K$_\alpha$ radiation, selected from a group consisting of about 8.1, 10.2, 11.2, 12.4, 12.8, 13.8, 15.3, 15.5, 16.0, 17.2, 18.3, 18.8, 19.4, 19.8, 20.6, 22.4, 23.8, 24.4, 24.9, 25.6, 26.4, and 27.4 degrees 2θ. In another embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by an X-ray powder diffraction (XRPD) pattern comprising at least three diffraction angles, when measured using Cu K$_\alpha$ radiation, selected from a group consisting of about 8.1, 10.2, 11.2, 12.4, 12.8, 13.8, 15.3, 15.5, 16.0, 17.2, 18.3, 18.8, 19.4, 19.8, 20.6, 22.4, 23.8, 24.4, 24.9, 25.6, 26.4, and 27.4 degrees 2θ.

In still another embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by an X-ray powder diffraction (XRPD) pattern comprising diffraction angles, when measured using Cu K$_\alpha$ radiation, of about 11.2, 13.8, 15.5, 18.8, 19.4, and 22.4 degrees 2θ. In yet another embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by an X-ray powder diffraction (XRPD) pattern substantially in accordance with FIG. 5.

In other embodiments, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by a Raman spectrum comprising at least twelve peaks at positions selected from a group consisting of peaks at about 436, 480, 511, 538, 550, 566, 611, 683, 776, 814, 852, 887, 925, 986, 1050, 1140, 1169, 1227, 1252, 1277, 1313, 1338, 1373, 1391, 1428, 1462, 1482, 1553, 1620, 2865, 2922, 2955, and 2973 cm$^{-1}$. In another embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by a Raman spectrum comprising at least eleven peaks or at least ten peaks or at least nine peaks or at least eight peaks or at least seven peaks at positions selected from a group consisting of peaks at about 436, 480, 511, 538, 550, 566, 611, 683, 776, 814, 852, 887, 925, 986, 1050, 1140, 1169, 1227, 1252, 1277, 1313, 1338, 1373, 1391, 1428, 1462, 1482, 1553, 1620, 2865, 2922, 2955, and 2973 cm$^{-1}$. In another embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by a Raman spectrum comprising at least six peaks at positions selected from a group consisting of peaks at about 436, 480, 511, 538, 550, 566, 611, 683, 776, 814, 852, 887, 925, 986, 1050, 1140, 1169, 1227, 1252, 1277, 1313, 1338, 1373, 1391, 1428, 1462, 1482, 1553, 1620, 2865, 2922, 2955, and 2973 cm$^{-1}$.

In still another embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by a Raman spectrum comprising peaks at about 611, 1169, 1227, 1277, 1313, 1482, 1553, 1620, 2922, and 2955 cm$^{-1}$. In yet another embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by a Raman spectrum substantially in accordance with FIG. 6.

Figure 7:
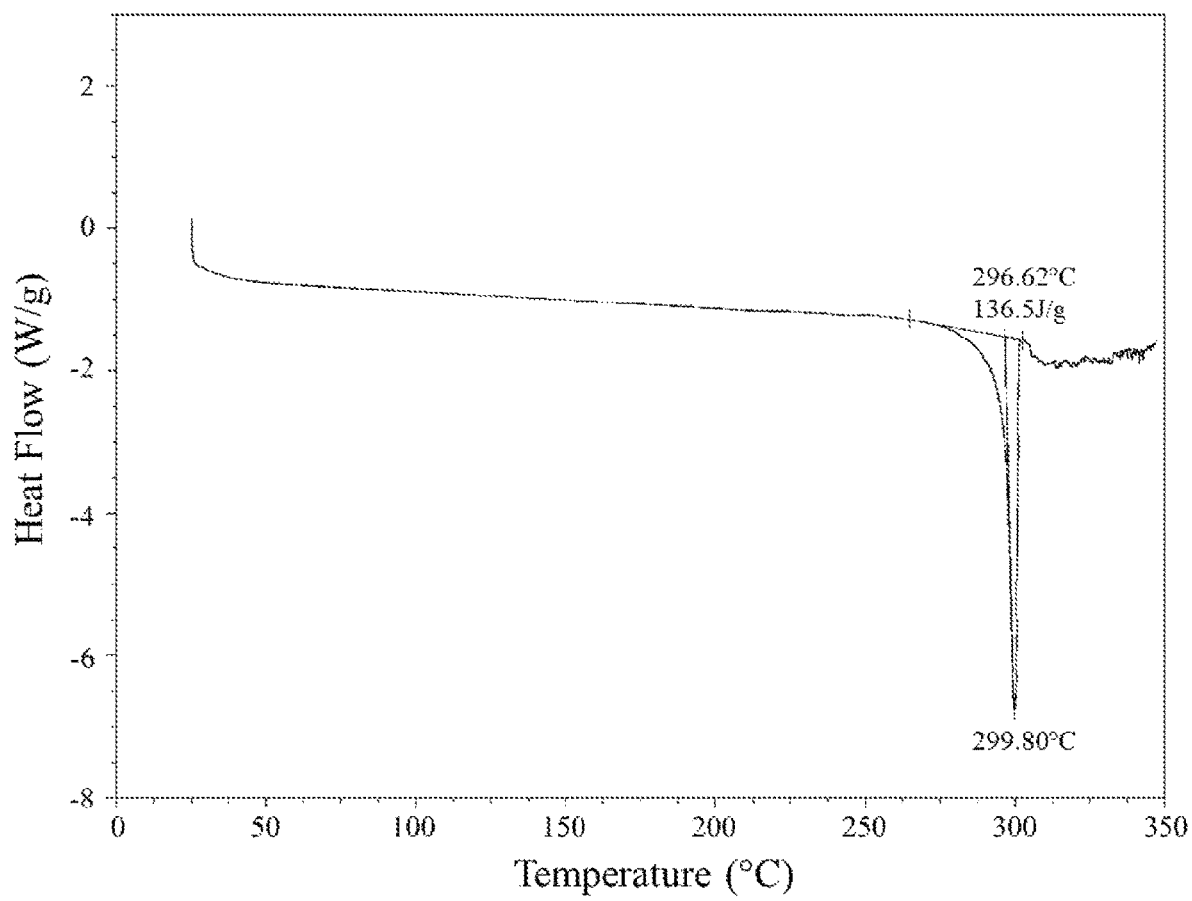
FIG. 7 shows a differential scanning calorimetry trace of the hydrochloric acid salt of the compound of Example 10 (Form I).
Figure 8:
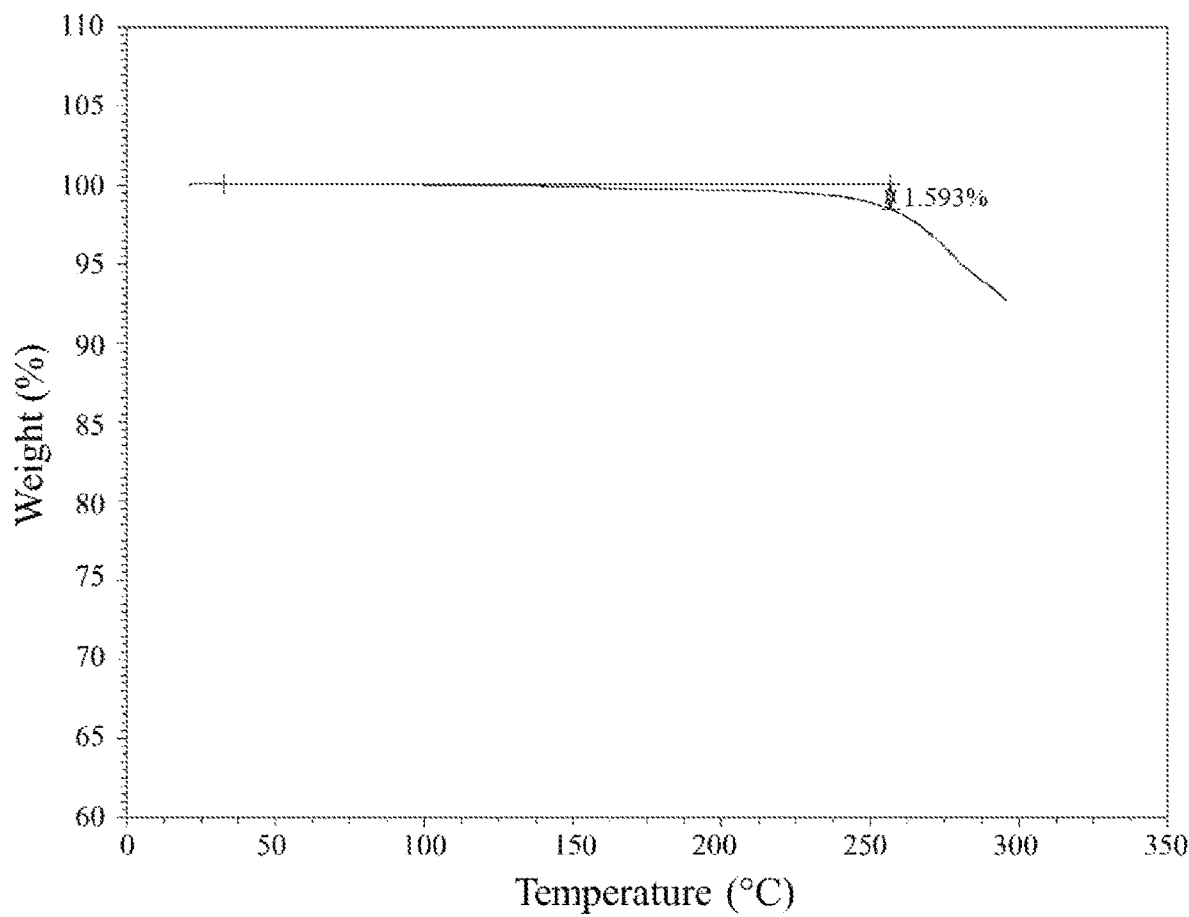
FIG. 8 shows a thermogravimetric analysis trace of the hydrochloric acid salt of the compound of Example 10 (Form I).

In further embodiments, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by a differential scanning calorimetry trace substantially in accordance with FIG. 7 and/or a thermogravimetric analysis trace substantially in accordance with FIG. 8.

In still further embodiments, as a person having ordinary skill in the art will understand, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by any combination of the analytical data characterizing the aforementioned embodiments. For example, in one embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by an X-ray powder diffraction (XRPD) pattern substantially in accordance with FIG. 5 and a Raman spectrum substantially in accordance with FIG. 6 and a differential scanning calorimetry trace substantially in accordance with FIG. 7 and a thermogravimetric analysis trace substantially in accordance with FIG. 8. In another embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by an X-ray powder diffraction (XRPD) pattern substantially in accordance with FIG. 5 and a Raman spectrum substantially in accordance with FIG. 6. In another embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by an X-ray powder diffraction (XRPD) pattern substantially in accordance with FIG. 5 and a differential scanning calorimetry trace substantially in accordance with FIG. 7. In another embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by an X-ray powder diffraction (XRPD) pattern substantially in accordance with FIG. 5 and a thermogravimetric analysis trace substantially in accordance with FIG. 8. In another embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by an X-ray powder diffraction (XRPD) pattern comprising diffraction angles, when measured using Cu K$_\alpha$ radiation, of about 11.2, 13.8, 15.5, 18.8, 19.4, and 22.4 degrees 2θ, and a Raman spectrum comprising peaks at about 611, 1169, 1227, 1277, 1313, 1482, 1553, 1620, 2922, and 2955 cm$^1$. In another embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by an X-ray powder diffraction (XRPD) pattern comprising diffraction angles, when measured using Cu K$_\alpha$ radiation, of about 11.2, 13.8, 15.5, 18.8, 19.4, and 22.4 degrees 2θ, and a differential scanning calorimetry trace substantially in accordance with FIG. 7. In another embodiment, the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is characterized by an X-ray powder diffraction (XRPD) pattern comprising diffraction angles, when measured using Cu K$_\alpha$ radiation, of about 11.2, 13.8, 15.5, 18.8, 19.4, and 22.4 degrees 2θ, and a thermogravimetric analysis trace substantially in accordance with FIG. 8.

Figure 5:
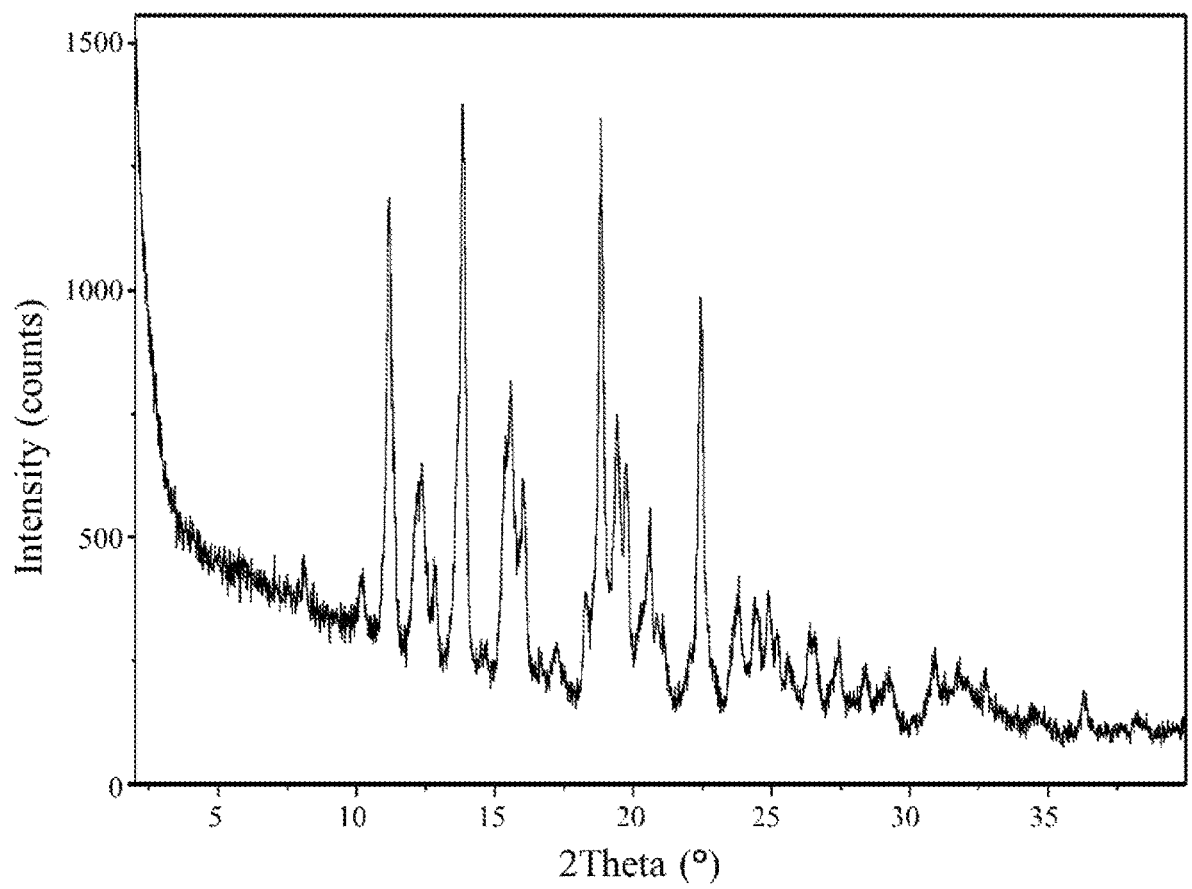
FIG. 5 shows an X-ray powder diffraction pattern of the hydrochloric acid salt of the compound of Example 10 (Form I).

An XRPD pattern will be understood to comprise a diffraction angle (expressed in degrees 2θ) of "about" a value specified herein when the XRPD pattern comprises a diffraction angle within ±0.3 degrees 2θ of the specified value. Further, it is well known and understood to those skilled in the art that the apparatus employed, humidity, temperature, orientation of the powder crystals, and other parameters involved in obtaining an X-ray powder diffraction (XRPD) pattern may cause some variability in the appearance, intensities, and positions of the lines in the diffraction pattern. An X-ray powder diffraction pattern that is "substantially in accordance" with that of FIG. 1 or 5 provided herein is an XRPD pattern that would be considered by one skilled in the art to represent a compound possessing the same crystal form as the compound that provided the XRPD pattern of FIG. 1 or 5. That is, the XRPD pattern may be identical to that of FIG. 1 or 5, or more likely it may be somewhat different. Such an XRPD pattern may not necessarily show each of the lines of any one of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay an XRPD pattern of a sample of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one, with FIG. 1 and, using expertise and knowledge in the art, readily determine whether the XRPD pattern of the sample is substantially in accordance with the XRPD pattern of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one (Form II) disclosed herein. If the XRPD pattern is substantially in accordance with FIG. 1, the sample form can be readily and accurately identified as having the same form as the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one (Form II) disclosed herein. Similarly, if an XRPD pattern of a sample of the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is substantially in accordance with FIG. 5, the sample form can be readily and accurately identified as having the same form as the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one (Form I) disclosed herein.

Figure 2:
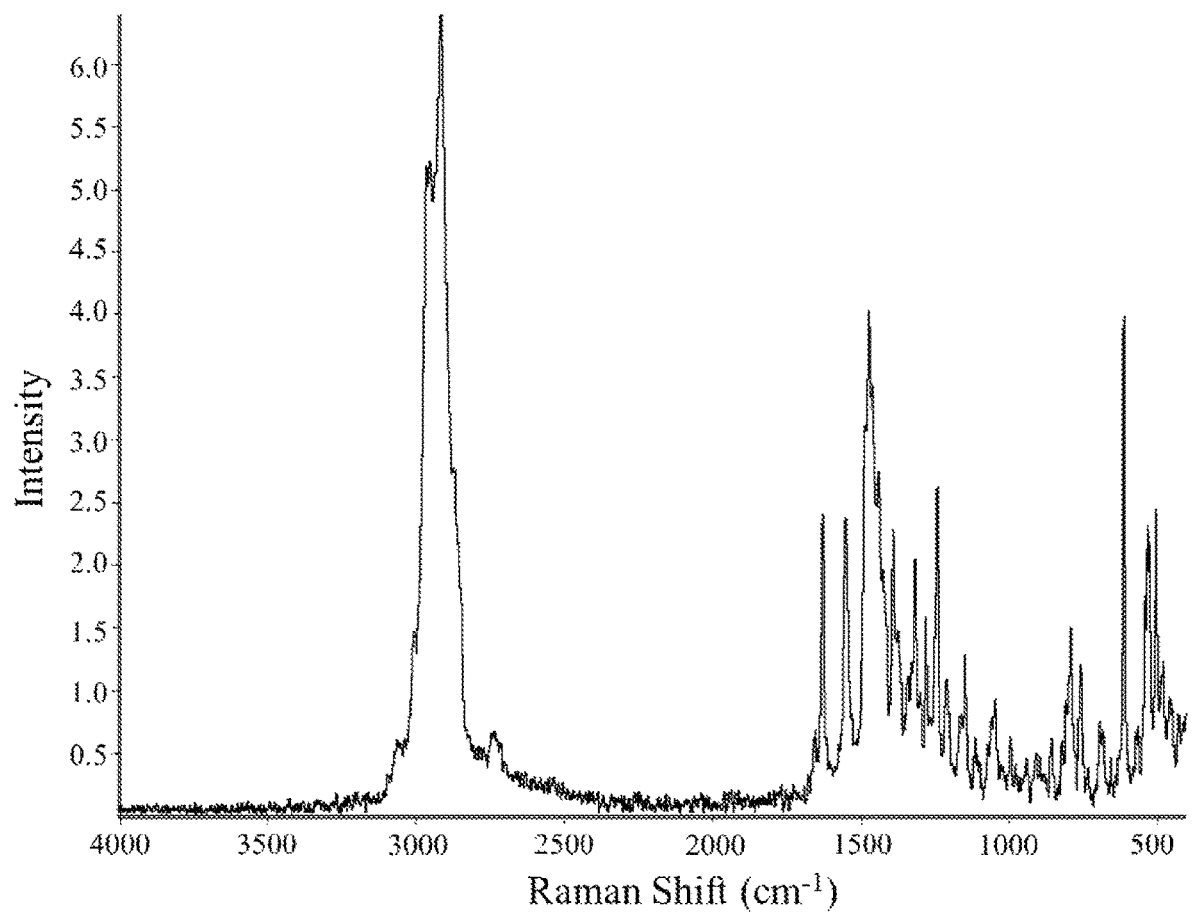
FIG. 2 shows a Raman spectrum of the hydrochloric acid salt of the compound of Example 1 (Form II).
Figure 6:
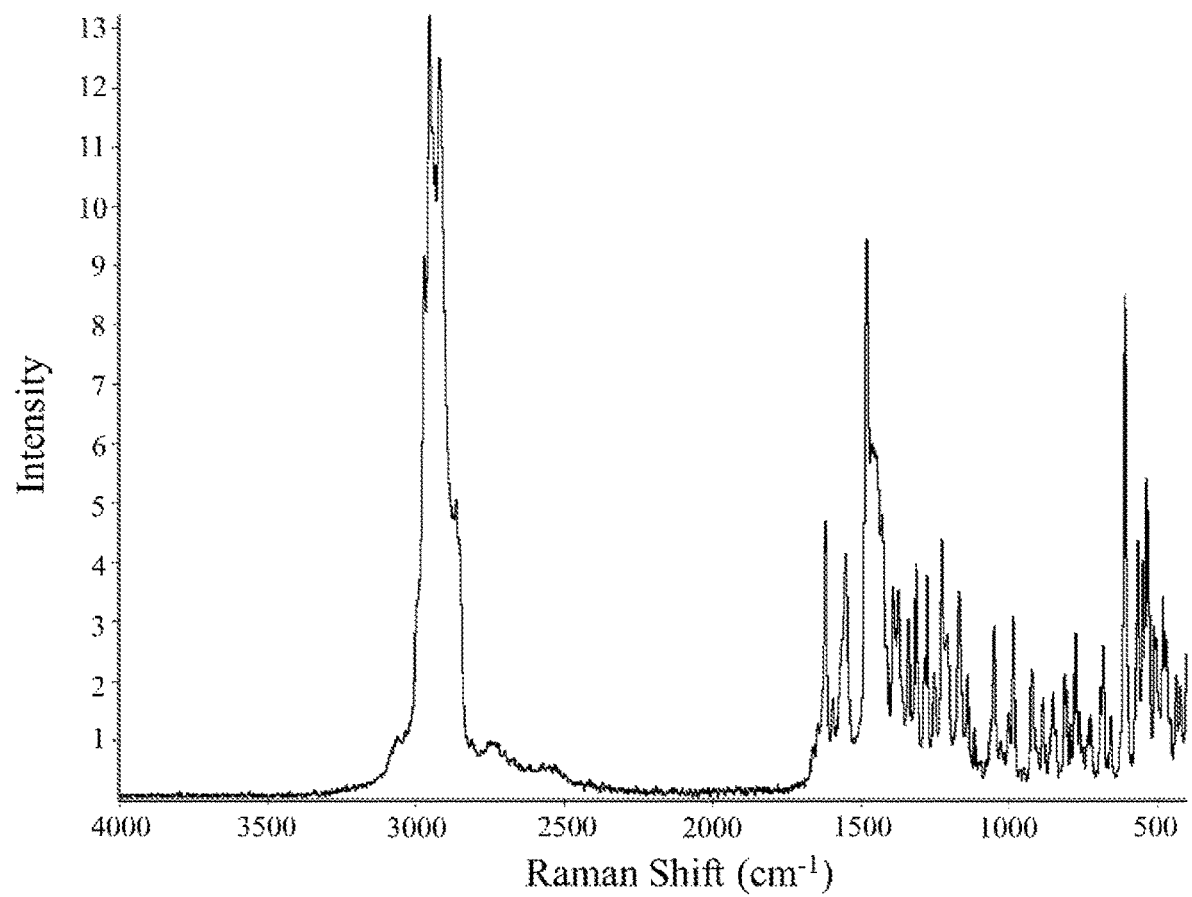
FIG. 6 shows a Raman spectrum of the hydrochloric acid salt of the compound of Example 10 (Form I).

A Raman spectrum will be understood to comprise a peak (expressed in $cm^{-1}$) of "about" a value specified herein when the Raman spectrum comprises a peak within ±5.0 $cm^{-1}$ of the specified value. Further, it is also well known and understood to those skilled in the art that the apparatus employed, humidity, temperature, orientation of the powder crystals, and other parameters involved in obtaining a Raman spectrum may cause some variability in the appearance, intensities, and positions of the peaks in the spectrum. A Raman spectrum that is "substantially in accordance" with that of FIG. 2 or 6 provided herein is a Raman spectrum that would be considered by one skilled in the art to represent a compound possessing the same crystal form as the compound that provided the Raman spectrum of FIG. 2 or 6. That is, the Raman spectrum may be identical to that of FIG. 2 or 6, or more likely it may be somewhat different. Such a Raman spectrum may not necessarily show each of the peaks of any one of the spectra presented herein, and/or may show a slight change in appearance, intensity, or a shift in position of said peaks resulting from differences in the conditions involved in obtaining the data. A person skilled in the art is capable of determining if a sample of a crystalline compound has the same form as, or a different form from, a form disclosed herein by comparison of their Raman spectra. For example, one skilled in the art can overlay a Raman spectrum of a sample of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one, with FIG. 2 and, using expertise and knowledge in the art, readily determine whether the Raman spectrum of the sample is substantially in accordance with the Raman spectrum of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one (Form II) disclosed herein. Similarly, if the Raman spectrum is substantially in accordance with FIG. 6, the sample form can be readily and accurately identified as having the same form as the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one (Form I) disclosed herein.

The compound of Formula (I) or a salt thereof may exist in stereoisomeric forms (e.g., it contains one or more asymmetric carbon atoms). The individual stereoisomers (enantiomers and diastereomers) and mixtures of these are included within the scope of the present invention. Likewise, it is understood that a compound or salt of Formula (I) may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. It is to be understood that the present invention includes all combinations and subsets of the particular groups defined hereinabove.

The subject invention also includes isotopically-labeled compounds, which are identical to those recited in Formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulfur, fluorine, chlorine, and iodine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$, and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^{3}H$, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of Formula (I) and following of this invention can generally be prepared by carrying out the procedures disclosed in the Schemes and/or in the Examples below, by substituting a readily available isotopically labeled reagent for a non-isotopically labeled reagent.

The invention further provides a pharmaceutical composition (also referred to as pharmaceutical formulation) comprising a compound of Formula (I) or pharmaceutically acceptable salt thereof and one or more excipients (also referred to as carriers and/or diluents in the pharmaceutical arts). The excipients are acceptable in the sense of being compatible with the other ingredients of the formulation and not deleterious to the recipient thereof (i.e., the patient).

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting of the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

Pharmaceutical compositions may be in unit dose form containing a predetermined amount of active ingredient per unit dose. Such a unit may contain a therapeutically effective dose of the compound of Formula (I) or salt thereof or a fraction of a therapeutically effective dose such that multiple unit dosage forms might be administered at a given time to achieve the desired therapeutically effective dose. Preferred unit dosage formulations are those containing a daily dose or sub-dose, as herein above recited, or an appropriate fraction thereof, of an active ingredient. Furthermore, such pharmaceutical compositions may be prepared by any of the methods well-known in the pharmacy art.

Pharmaceutical compositions may be adapted for administration by any appropriate route, for example, by oral (including buccal or sublingual), rectal, nasal, topical (including buccal, sublingual, or transdermal), vaginal, or parenteral (including subcutaneous, intramuscular, intravenous, or intradermal) routes. Such compositions may be prepared by any method known in the art of pharmacy, for example, by bringing into association the active ingredient with the excipient(s).

When adapted for oral administration, pharmaceutical compositions may be in discrete units such as tablets or capsules; powders or granules; solutions or suspensions in aqueous or non-aqueous liquids; edible foams or whips; oil-in-water liquid emulsions or water-in-oil liquid emulsions. The compound or salt thereof of the invention or the pharmaceutical composition of the invention may also be incorporated into a candy, a wafer, and/or tongue tape formulation for administration as a "quick-dissolve" medicine.

For instance, for oral administration in the form of a tablet or capsule, the active drug component can be combined with an oral, non-toxic pharmaceutically acceptable inert carrier such as ethanol, glycerol, water, and the like. Powders or granules are prepared by comminuting the compound to a suitable fine size and mixing with a similarly comminuted pharmaceutical carrier such as an edible carbohydrate, as, for example, starch or mannitol. Flavoring, preservative, dispersing, and coloring agents can also be present.

Capsules are made by preparing a powder mixture, as described above, and filling formed gelatin or non-gelatinous sheaths. Glidants and lubricants such as colloidal silica, talc, magnesium stearate, calcium stearate, solid polyethylene glycol can be added to the powder mixture before the filling operation. A disintegrating or solubilizing agent such as agar-agar, calcium carbonate, or sodium carbonate can also be added to improve the availability of the medicine when the capsule is ingested.

Moreover, when desired or necessary, suitable binders, lubricants, disintegrating agents, and coloring agents can also be incorporated into the mixture. Suitable binders include starch, gelatin, natural sugars, such as glucose or beta-lactose, corn sweeteners, natural and synthetic gums such as acacia, tragacanth, sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, and aliginate, gelatin, or polyvinyl pyrrolidone, a solution retardant such as paraffin, a resorption accelerator such as a quaternary salt, and/or an absorption agent such as bentonite, kaolin, or dicalcium phosphate. The powder mixture can be granulated by wetting a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound or salt of the present invention can also be combined with a free-flowing inert carrier and compressed into tablets directly without going through the granulating or slugging steps. A clear opaque protective coating consisting of a sealing coat of shellac, a coating of sugar, or polymeric material, and a polish coating of wax can be provided. Dyestuffs can be added to these coatings to distinguish different dosages.

Oral fluids such as solutions, syrups, and elixirs can be prepared in dosage unit form so that a given quantity contains a predetermined amount of active ingredient. Syrups can be prepared by dissolving the compound or salt thereof of the invention in a suitably flavoured aqueous solution, while elixirs are prepared through the use of a non-toxic alcoholic vehicle. Suspensions can be formulated by dispersing the compound or salt of the invention in a non-toxic vehicle. Solubilizers and emulsifiers, such as ethoxylated isostearyl alcohols and polyoxyethylene sorbitol ethers, preservatives, flavor additives such as peppermint oil, natural sweeteners, saccharin, or other artificial sweeteners, and the like, can also be added.

Where appropriate, dosage unit formulations for oral administration can be microencapsulated. The formulation can also be prepared to prolong or sustain the release as, for example, by coating or embedding particulate material in polymers, wax, or the like.

In the present invention, tablets and capsules are preferred for delivery of the pharmaceutical composition.

In accordance with another aspect of the invention there is provided a process for the preparation of a pharmaceutical composition comprising mixing (or admixing) a compound of Formula (I) or salt thereof with at least one excipient.

The present invention also provides a method of treatment in a mammal, especially a human. The compounds and compositions of the invention are used to treat cellular proliferation diseases. Disease states which can be treated by the methods and compositions provided herein include, but are not limited to, cancer (further discussed below), autoimmune disease, fungal disorders, arthritis, graft rejection, inflammatory bowel disease, proliferation induced after medical procedures, including, but not limited to, surgery, angioplasty, and the like. It is appreciated that in some cases the cells may not be in a hyper or hypo proliferation state (abnormal state) and still requires treatment. For example, during wound healing, the cells may be proliferating "normally", but proliferation enhancement may be desired. Thus, in one embodiment, the invention herein includes application to cells or individuals afflicted or impending affliction with any one of these disorders or states.

The compositions and methods provided herein are particularly deemed useful for the treatment of cancer including tumors such as prostate, breast, brain, skin, cervical carcinomas, testicular carcinomas, etc. They are particularly useful in treating metastatic or malignant tumors. More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma, diffuse large B-cell lymphoma (DLBCL), follicular lymphoma); Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one or related of the above identified conditions.

The compounds and compositions of the invention may also be used to treat or cure human immunodeficiency virus (HIV) infection. In one embodiment, there is provided a method of treating HIV infection comprising administering to a patient with HIV a therapeutically effective amount of a compound of Formula (I) or a pharmaceutically acceptable salt thereof. In another embodiment, there is provided a method of curing HIV infection comprising administering to a patient with HIV a therapeutically effective amount of a compound of Formula (I) or a pharmaceutically acceptable salt thereof. In another embodiment, there is provided the use of a compound of Formula (I) or a pharmaceutically acceptable salt or solvate thereof, in the manufacture of a medicament for use in the treatment of HIV infection. In another embodiment, there is provided the use of a compound of Formula (I) or a pharmaceutically acceptable salt or solvate thereof, in the manufacture of a medicament for use in the cure of HIV infection. In another embodiment, there is provided a compound of Formula (I) or a pharmaceutically acceptable salt thereof for use in the treatment of HIV infection. In another embodiment, there is provided a compound of Formula (I) or a pharmaceutically acceptable salt thereof for use in the cure of HIV infection.

The instant compounds can be combined with or co-administered with other therapeutic agents, particularly agents that may enhance the activity or time of disposition of the compounds. Combination therapies according to the invention comprise the administration of at least one compound of the invention and the use of at least one other treatment method. In one embodiment, combination therapies according to the invention comprise the administration of at least one compound of the invention and surgical therapy. In one embodiment, combination therapies according to the invention comprise the administration of at least one compound of the invention and radiotherapy. In one embodiment, combination therapies according to the invention comprise the administration of at least one compound of the invention and at least one supportive care agent (e.g., at least one anti-emetic agent). In one embodiment, combination therapies according to the present invention comprise the administration of at least one compound of the invention and at least one other chemotherapeutic agent. In one particular embodiment, the invention comprises the administration of at least one compound of the invention and at least one anti-neoplastic agent. In yet another embodiment, the invention comprises a therapeutic regimen where the EZH2 inhibitors of this disclosure are not in and of themselves active or significantly active, but when combined with another therapy, which may or may not be active as a standalone therapy, the combination provides a useful therapeutic outcome.

By the term "co-administration" and derivatives thereof as used herein refers to either simultaneous administration or any manner of separate sequential administration of an EZH2 inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita, T. S. Lawrence, and S. A. Rosenberg (editors), $10^{th}$ edition (Dec. 5, 2014), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule or anti-mitotic agents; platinum coordination complexes; alkylating agents; antibiotic agents; topoisomerase I inhibitors; topoisomerase II inhibitors; antimetabolites; hormones and hormonal analogues; signal transduction pathway inhibitors; non-receptor tyrosine kinase angiogenesis inhibitors; immunotherapeutic agents; proapoptotic agents; cell cycle signalling inhibitors; proteasome inhibitors; heat shock protein inhibitors; inhibitors of cancer metabolism; and cancer gene therapy agents.

Examples of a further active ingredient or ingredients for use in combination or co-administered with the present EZH2 inhibiting compounds are anti-neoplastic agents. Examples of anti-neoplastic agents include, but are not limited to, chemotherapeutic agents; immuno-modulatory agents; immune-modulators; and immunostimulatory adjuvants.

Anti-microtubule or anti-mitotic agents are phase specific agents active against the microtubules of tumor cells during M or the mitosis phase of the cell cycle. Examples of anti-microtubule agents include, but are not limited to, diterpenoids and *vinca* alkaloids.

Platinum coordination complexes are non-phase specific anti-cancer agents, which are interactive with DNA. The platinum complexes enter tumor cells, undergo aquation, and form intra- and interstrand crosslinks with DNA causing adverse biological effects to the tumor. Examples of platinum coordination complexes include, but are not limited to, cisplatin and carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Antibiotic anti-neoplastics are non-phase specific agents, which bind or intercalate with DNA. This action disrupts the ordinary function of the nucleic acids, leading to cell death. Examples of antibiotic anti-neoplastic agents include, but are not limited to, actinomycins such as dactinomycin; anthrocyclins such as daunorubicin and doxorubicin; and bleomycins.

Topoisomerase I inhibitors include, but are not limited to, camptothecins. The cytotoxic activity of camptothecins is believed to be related to its topoisomerase I inhibitory activity.

Topoisomerase II inhibitors include, but are not limited to, epipodophyllotoxins. Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as dexamethasone, prednisone, and prednisolone; aminoglutethimide and other aromatase inhibitors such as anastrozole, letrazole, vorazole, and exemestane; progestrins such as megestrol acetate; estrogens, androgens, and anti-androgens such as flutamide, nilutamide, bicalutamide, cyproterone acetate and 5α-reductases such as finasteride and dutasteride; anti-estrogens such as tamoxifen, toremifene, raloxifene, droloxifene, iodoxyfene, as well as selective estrogen receptor modulators (SERMS); and gonadotropin-releasing hormone (GnRH) and analogues thereof, which stimulate the release of leutinizing hormone (LH) and/or follicle stimulating hormone (FSH), LHRH agonists, and antagonists such as goserelin acetate and leuprolide.

Signal transduction pathway inhibitors are those inhibitors, which block or inhibit a chemical process which evokes an intracellular change. As used herein, this change is cell proliferation or differentiation. Signal transduction inhibitors useful in the present invention include, but are not limited to, inhibitors of receptor tyrosine kinases, non-receptor tyrosine kinases, SH2/SH3 domain blockers, serine/threonine kinases, phosphatidyl inositol-3 kinases, myo-inositol signalling, and Ras oncogenes.

Several protein tyrosine kinases catalyze the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFR), tyrosine kinase with immunoglobulin-like and epidermal growth factor homology domains (TIE-2), insulin growth factor-I (IGFI) receptor, macrophage colony stimulating factor Cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath J. C., Exp. Opin. Ther. Patents, 10(6):803-818 (2000); Shawver L. K., et al., Drug Discov. Today, 2(2): 50-63 (1997); and Lofts, F. J. and Gullick W. J., "Growth factor receptors as targets." in New Molecular Targets for Cancer Chemotherapy, Kerr D. J. and Workman P. (editors), (Jun. 27, 1994), CRC Press. Non-limiting examples of growth factor receptor inhibitors include pazopanib and sorafenib.

Tyrosine kinases, which are not growth factor receptor kinases, are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinha S. and Corey S. J., J. Hematother. Stem Cell Res., 8(5): 465-480 (2004) and Bolen, J. B., Brugge, J. S., Annu. Rev. Immunol., 15: 371-404 (1997).

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall T. E., J. Pharmacol. Toxicol. Methods, 34(3): 125-32 (1995).

Inhibitors of serine/threonine kinases include, but are not limited to, MAP kinase cascade blockers which include blockers of Raf kinases (rafk), Mitogen or Extracellular Regulated Kinase (MEKs), and Extracellular Regulated Kinases (ERKs); Protein kinase C family member blockers including blockers of PKCs (alpha, beta, gamma, epsilon, mu, lambda, iota, zeta); IkB kinases (IKKa, IKKb); PKB family kinases; AKT kinase family members; TGF beta receptor kinases; and mammaliam target of rapamycin (mTOR) inhibitors, including, but not limited to rapamycin (FK506) and rapalogs, RAD001 or everolimus (AFINITOR®), CCI-779 or temsirolimus, AP23573, AZD8055, WYE-354, WYE-600, WYE-687 and Pp 121. Examples of inhibitors of serine/threonine kinases include, but are not limited to, trametinib, dabrafenib, and Akt inhibitors afuresertib and N-{(1S)-2-amino-1-[(3,4-difluorophenyl)methyl]ethyl}-5-chloro-4-(4-chloro-1-methyl-1H-pyrazol-5-yl)-2-furancarboxamide.

Inhibitors of phosphatidyl inositol 3-kinase family members including blockers of PI3-kinase, ATM, DNA-PK, and Ku are also useful in the present invention. Such kinases are discussed in Abraham R. T., Curr. Opin. Immunol., 8(3): 412-418 (1996); Canman C. E., and Lim D. S., Oncogene, 17(25): 3301-3308 (1998); Jackson S. P., Int. J. Biochem. Cell Biol., 29(7): 935-938 (1997); and Zhong H., et al., Cancer Res., 60(6): 1541-1545 (2000).

Also useful in the present invention are myo-inositol signalling inhibitors such as phospholipase C blockers and myo-inositol analogs. Such signal inhibitors are described in Powis G., and Kozikowski A., "Inhibitors of Myo-Inositol Signaling." in New Molecular Targets for Cancer Chemotherapy, Kerr D. J. and Workman P. (editors), (Jun. 27, 1994), CRC Press.

Another group of signal transduction pathway inhibitors are inhibitors of Ras oncogene. Such inhibitors include inhibitors of farnesyltransferase, geranyl-geranyl transferase, and CAAX proteases as well as anti-sense oligonucleotides, ribozymes and other immunotherapies. Such inhibitors have been shown to block ras activation in cells containing wild type mutant ras, thereby acting as antiproliferation agents. Ras oncogene inhibition is discussed in Scharovsky O. G., et al., J. Biomed. Sci., 7(4): 292-298 (2000); Ashby M. N., Curr. Opin. Lipidol., 9(2): 99-102 (1998); and Bennett C. F. and Cowsert L. M., Biochim. Biophys. Acta., 1489(1): 19-30 (1999).

Antagonists to receptor kinase ligand binding may also serve as signal transduction inhibitors. This group of signal transduction pathway inhibitors includes the use of humanized antibodies or other antagonists to the extracellular ligand binding domain of receptor tyrosine kinases. Examples of antibody or other antagonists to receptor kinase ligand binding include, but are not limited to, cetuximab (ERBITUX®), trastuzumab (HERCEPTIN®); trastuzumab emtansine (KADCYLA®); pertuzumab (PERJETA®); ErbB inhibitors including lapatinib, erlotinib, and gefitinib; and 2C3 VEGFR2 specific antibody (see Brekken R. A., et al., Cancer Res., 60(18): 5117-5124 (2000)).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alphav beta$_3$) that will inhibit angiogenesis; endostatin and angiostatin (non-RTK) may also prove useful in combination with the disclosed compounds. (See Bruns C. J., et al., Cancer Res., 60(11): 2926-2935 (2000); Schreiber A. B., et al., Science, 232(4755): 1250-1253 (1986); Yen L., et al., Oncogene, 19(31): 3460-3469 (2000)).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R. T., et al., Cancer Res., 60(13): 3569-3576 (2000); and Chen Y., et al., Cancer Res., 58(9): 1965-1971 (1998).

Agents used in proapoptotic regimens (e.g., Bcl-2 antisense oligonucleotides) may also be used in the combination of the present invention. Members of the Bcl-2 family of proteins block apoptosis. Upregulation of Bcl-2 has therefore been linked to chemoresistance. Studies have shown that the epidermal growth factor (EGF) stimulates anti-apoptotic members of the Bcl-2 family (i.e., Mcl-1). Therefore, strategies designed to downregulate the expression of Bcl-2 in tumors have demonstrated clinical benefit. Such proapoptotic strategies using the antisense oligonucleotide strategy for Bcl-2 are discussed in Waters J. S., et al., J. Clin. Oncol., 18(9): 1812-1823 (2000); and Kitada S., et al., Antisense Res. Dev., 4(2): 71-79 (1994). Examples of small molecule Bcl-2 inhibitors include, but are not limited to venetoclax.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania G. R., and Chang Y. T., Exp. Opin. Ther. Patents, 10(2): 215-230 (2000). Further, p21WAF1/CIP1 has been described as a potent and universal inhibitor of cyclin-dependent kinases (Cdks) (Ball K. L., Prog. Cell Cycle Res., 3: 125-134 (1997)). Compounds that are known to induce expression of p21WAF1/CIP1 have been implicated in the suppression of cell proliferation and as having tumor suppressing activity (Richon V. M., et al., Proc. Natl. Acad. Sci. USA, 97(18): 10014-10019 (2000)), and are included as cell cycle signaling inhibitors. Histone deacetylase (HDAC) inhibitors are implicated in the transcriptional activation of p21WAF1/CIP1 (Vigushin D. M., and Coombes R. C., Anticancer Drugs, 13(1): 1-13 (2002)), and are suitable cell cycle signaling inhibitors for use in combination herein. Examples of such HDAC inhibitors include, but are not limited to vorinostat, romidepsin, panobinostat, valproic acid, and mocetinostat.

Proteasome inhibitors are drugs that block the action of proteasomes, cellular complexes that break down proteins, like the p53 protein. Several proteasome inhibitors are marketed or are being studied for the treatment of cancer. Suitable proteasome inhibitors for use in combination herein include, but are not limited to bortezomib, disulfiram, epigallocatechin gallate, salinosporamide A, and carfilzomib.

The 70 kilodalton heat shock proteins (Hsp70s) and 90 kilodalton heat shock proteins (Hsp90s) are a family of ubiquitously expressed heat shock proteins. Hsp70s and Hsp90s are over expressed certain cancer types. Several Hsp70 and Hsp90 inhibitors are being studied in the treatment of cancer. Examples of Hsp70 and Hsp90 inhibitors for use in combination herein include, but are not limited to tanespimycin and radicicol.

Many tumor cells show a markedly different metabolism from that of normal tissues. For example, the rate of glycolysis, the metabolic process that converts glucose to pyruvate, is increased, and the pyruvate generated is reduced to lactate, rather than being further oxidized in the mitochondria via the tricarboxylic acid (TCA) cycle. This effect is often seen even under aerobic conditions and is known as the Warburg Effect.

Lactate dehydrogenase A (LDH-A), an isoform of lactate dehydrogenase expressed in muscle cells, plays a pivotal role in tumor cell metabolism by performing the reduction of pyruvate to lactate, which can then be exported out of the cell. The enzyme has been shown to be upregulated in many tumor types. The alteration of glucose metabolism described in the Warburg effect is critical for growth and proliferation of cancer cells and knocking down LDH-A using RNA-i has been shown to lead to a reduction in cell proliferation and tumor growth in xenograft models (Tennant D. A., et al., Nat. Rev. Cancer, 10(4): 267-277 (2010); Fantin V. R., et al., Cancer Cell, 9(6): 425-434 (2006)).

High levels of fatty acid synthase (FAS) have been found in cancer precursor lesions. Pharmacological inhibition of FAS affects the expression of key oncogenes involved in both cancer development and maintenance. Alli P. M., et al., Oncogene, 24(1): 39-46 (2005).

Inhibitors of cancer metabolism, including inhibitors of LDH-A and inhibitors of fatty acid biosynthesis (or FAS inhibitors), are suitable for use in combination herein. Cancer gene therapy involves the selective transfer of recombinant DNA/RNA using viral or nonviral gene delivery vectors to modify cancer calls for therapeutic purposes. Examples of cancer gene therapy include, but are not limited to suicide and oncolytic gene therapies, as well as adoptive T-cell therapies.

As used herein "immuno-modulators" refer to any substance including monoclonal antibodies that affects the immune system. Immuno-modulators can be used as anti-neoplastic agents for the treatment of cancer. For example, immune-modulators include, but are not limited to, antibodies or other antagonists to CTLA-4, such as ipilimumab (YERVOY®), and PD-1, such as nivolumab (OPDIVO®) and pembrolizumab (KEYTRUDA®). Other immuno-modulators include, but are not limited to, antibodies or other antagonists to PD-L1, OX-40, LAG3, TIM-3, 41BB, and GITR.

As used herein, "PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L1; and PDCD1L2, PDL2, B7-DC, Btdc and CD273 for PD-L2. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in the any of the aspects of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')2, scFv and Fv fragments. Examples of mAbs that bind to human PD-1, and useful in the various aspects and embodiments of the present invention, are described in U.S. Pat. Nos. 8,552,154; 8,354,509; 8,168,757; 8,008,449; 7,521,051; 7,488,802; WO2004072286; WO2004056875; and WO2004004771.

Other PD-1 antagonists useful in the any of the aspects and embodiments of the present invention include an immunoadhesin that specifically binds to PD-1, and preferably specifically binds to human PD-1, e.g., a fusion protein containing the extracellular or PD-1 binding portion of PD-L1 or PD-L2 fused to a constant region such as an Fc region of an immunoglobulin molecule. Examples of immunoadhesin molecules that specifically bind to PD-1 are described in WO2010027827 and WO2011066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Nivolumab is a humanized monoclonal anti-PD-1 antibody commercially available as OPDIVO®. Nivolumab is indicated for the treatment of some unresectable or metastatic melanomas. Nivolumab binds to and blocks the activation of PD-1, an Ig superfamily transmembrane protein, by its ligands PD-L1 and PD-L2, resulting in the activation of T-cells and cell-mediated immune responses against tumor cells or pathogens. Activated PD-1 negatively regulates T-cell activation and effector function through the suppression of P13k/Akt pathway activation. Other names for nivolumab include: BMS-936558, MDX-1106, and ONO-4538. The amino acid sequence for nivolumab and methods of using and making are disclosed in U.S. Pat. No. 8,008,449.

Pembrolizumab is a humanized monoclonal anti-PD-1 antibody commercially available as KEYTRUDA®. Pembrolizumab is indicated for the treatment of some unresectable or metastatic melanomas. The amino acid sequence of pembrolizumab and methods of using are disclosed in U.S. Pat. No. 8,168,757.

Anti-PD-L1 antibodies and methods of making the same are known in the art. Such antibodies to PD-L1 may be polyclonal or monoclonal, and/or recombinant, and/or humanized. PD-L1 antibodies are in development as immuno-modulatory agents for the treatment of cancer.

Exemplary PD-L1 antibodies are disclosed in U.S. Pat. Nos. 9,212,224; 8,779,108; 8,552,154; 8,383,796; 8,217, 149; US Patent Publication No. 20110280877; WO2013079174; and WO2013019906. Additional exemplary antibodies to PD-L1 (also referred to as CD274 or B7-H1) and methods for use are disclosed in U.S. Pat. Nos. 8,168,179; 7,943,743; 7,595,048; WO2014055897; WO2013019906; and WO2010077634. Specific anti-human PD-L1 monoclonal antibodies useful as a PD-1 antagonist in the treatment method, medicaments and uses of the present invention include MPDL3280A, BMS-936559, MEDI4736, MSB0010718C.

Atezolizumab is a fully humanized monoclonal anti-PD-L1 antibody commercially available as TECENTRIQ™. Atezolizumab is indictated for the treatment of some locally advanced or metastatic urothelial carcinomas. Atezolizumab blocks the interaction of PD-L1 with PD-1 and CD80.

CD134, also known as OX40, is a member of the TNFR-superfamily of receptors which is not constitutively expressed on resting naïve T cells, unlike CD28. OX40 is a secondary costimulatory molecule, expressed after 24 to 72 hours following activation; its ligand, OX40L, is also not expressed on resting antigen presenting cells, but is following their activation. Expression of OX40 is dependent on full activation of the T cell; without CD28, expression of OX40 is delayed and of fourfold lower levels. OX-40 antibodies, OX-40 fusion proteins and methods of using them are disclosed in U.S. Pat. Nos. 7,504,101; 7,758,852; 7,858,765; 7,550,140; 7,960,515; WO2012027328; WO2013028231.

Additional examples of a further active ingredient or ingredients (anti-neoplastic agent) for use in combination or co-administered with the presently invented EZH2 inhibiting compounds are antibodies or other antagonists to CD20, retinoids, or other kinase inhibitors. Examples of such antibodies or antagonists include, but are not limited to rituximab (RITUXAN® and MABTHERA®), of atumumab (ARZERRA®), and bexarotene (TARGRETIN®). Antibodies or antagonists of this sort may be additionally combined with further active agents, including alkylating agents, antibiotic anti-neoplastic agents (such as intercalating agents), other anti-neoplastic agents (such as *vinca* alkaloids), and adrenocorticosteroids. For example such a combination may include rituximab, cyclophosphamide, doxorubicin, vincristine, and prednisone (R-CHOP).

Additional examples of a further active ingredient or ingredients (anti-neoplastic agent) for use in combination or co-administered with the presently invented EZH2 inhibiting compounds are Toll-like Receptor 4 (TLR4) antagonists, including but not limited to aminoalkyl glucosaminide phosphates (AGPs).

AGPs are known to be useful as vaccine adjuvants and immunostimulatory agents for stimulating cytokine production, activating macrophages, promoting innate immune response, and augmenting antibody production in immunized animals. AGPs are synthetic ligands of TLR4. AGPs and their immunomodulating effects via TLR4 are disclosed in patent publications such as WO 2006016997, WO 2001090129, and/or U.S. Pat. No. 6,113,918 and have been reported in the literature. Additional AGP derivatives are disclosed in U.S. Pat. Nos. 7,129,219, 6,911,434, and 6,525,028. Certain AGPs act as agonists of TLR4, while others are recognized as TLR4 antagonists.

Additional non-limiting examples of a further active ingredient or ingredients (anti-neoplastic agent) for use in combination or co-administered with the presently invented EZH2 inhibiting compounds are antibodies to ICOS.

CDRs for murine antibodies to human ICOS having agonist activity are shown in PCT/EP2012/055735 (WO 2012131004). Antibodies to ICOS are also disclosed in WO 2008137915, WO 2010056804, EP 1374902, EP1374901, and EP1125585.

Additional non-limiting examples of a further active ingredient or ingredients (anti-neoplastic agent) for use in combination or co-administered with the presently invented EZH2 inhibiting compounds are STING modulating compounds, CD39 inhibitors and A2a and A2a adenosine antagonists.

Select anti-neoplastic agents that may be used in combination with a compound of Formula (I) or a pharmaceutically acceptable salt thereof, include but are not limited to: abarelix, abemaciclib, abiraterone, afatinib, aflibercept, aldoxorubicin, alectinib, alemtuzumab, arsenic trioxide, asparaginase, axitinib, AZD-9291, belinostat, bendamustine, bevacizumab, blinatumomab, bosutinib, brentuximab vedotin, cabazitaxel, cabozantinib, capecitabine, ceritinib, clofarabine, cobimetinib, crizotinib, daratumumab, dasatinib, degarelix, denosumab, dinutuximab, docetaxel, elotuzumab, entinostat, enzalutamide, epirubicin, eribulin, filgrastim, flumatinib, fulvestrant, fruquintinib, gemtuzumab ozogamicin, ibritumomab, ibrutinib, idelalisib, imatinib, irinotecan, ixabepilone, ixazomib, lenalidomide, lenvatinib, leucovorin, mechlorethamine, necitumumab, nelarabine, netupitant, nilotinib, obinutuzumab, olaparib, omacetaxine, osimertinib, oxaliplatin, paclitaxel, palbociclib, palonosetron, panitumumab, pegfilgrastim, peginterferon alfa-2b, pemetrexed, plerixafor, pomalidomide, ponatinib, pralatrexate, quizartinib, radium-223, ramucirumab, regorafenib, rolapitant, rucaparib, sipuleucel-T, sonidegib, sunitinib, talimogene laherparepvec, tipiracil, topotecan, trabectedin, trifluridine, triptorelin, uridine, vandetanib, velaparib, vemurafenib, venetoclax, vincristine, vismodegib, and zoledronic acid.

In addition, the compounds of Formula (I) may be used in combination with one or more other agents that may be useful in the treatment or cure of HIV.

Examples of such agents include, but are not limited to:

Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, GSK2248761, TMC-278, TMC-125, etravirine, and similar agents;

Protease inhibitors such as saquinavir, ritonavir, indinavir, nelfinavir, amprenavir, fosamprenavir, brecanavir, darunavir, atazanavir, tipranavir, palinavir, lasinavir, and similar agents;

Entry, attachment and fusion inhibitors such as enfuvirtide (T-20), T-1249, PRO-542, PRO-140, TNX-355, BMS-806, BMS-663068 and BMS-626529, 5-Helix and similar agents;

Integrase inhibitors such as raltegravir, elvitegravir, dolutegravir, cabotegravir and similar agents;

Maturation inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

Further examples where the compounds of the present invention may be used in combination with one or more agents useful in the prevention or treatment of HIV are found in Table 1.

TABLE 1

| FDA Approval | Brand Name | Generic Name | Manufacturer |
|---|---|---|---|
| Nucleoside Reverse Transcriptase Inhibitors (NRTIs) | | | |
| 1987 | Retrovir | zidovudine, azidothymidine, AZT, ZDV | GlaxoSmithKline |
| 1991 | Videx | didanosine, dideoxyinosine, ddI | Bristol-Myers Squibb |
| 1992 | Hivid | zalcitabine, dideoxycytidine, ddC | Roche Pharmaceuticals |
| 1994 | Zerit | stavudine, d4T | Bristol-Myers Squibb |
| 1995 | Epivir | lamivudine, 3TC | GlaxoSmithKline |
| 1997 | Combivir | lamivudine + zidovudine | GlaxoSmithKline |
| 1998 | Ziagen | abacavir sulfate, ABC | GlaxoSmithKline |
| 2000 | Trizivir | abacavir + lamivudine + zidovudine | GlaxoSmithKline |
| 2000 | Videx EC | enteric coated didanosine, ddI EC | Bristol-Myers Squibb |
| 2001 | Viread | tenofovir disoproxil fumarate, TDF | Gilead Sciences |
| 2003 | Emtriva | emtricitabine, FTC | Gilead Sciences |
| 2004 | Epzicom | abacavir + lamivudine | GlaxoSmithKline |
| 2004 | Truvada | emtricitabine + tenofovir disoproxil fumarate | Gilead Sciences |

TABLE 1-continued

| FDA Approval | Brand Name | Generic Name | Manufacturer |
|---|---|---|---|
| Non-Nucleosides Reverse Transcriptase Inhibitors (NNRTIs) | | | |
| 1996 | Viramune | nevirapine, NVP | Boehringer Ingelheim |
| 1997 | Rescriptor | delavirdine, DLV | Pfizer |
| 1998 | Sustiva | efavirenz, EFV | Bristol-Myers Squibb |
| 2008 | Intelence | Etravirine | Tibotec Therapeutics |
| Protease Inhibitors (PIs) | | | |
| 1995 | Invirase | saquinavir mesylate, SQV | Roche Pharmaceuticals |
| 1996 | Norvir | ritonavir, RTV | Abbott Laboratories |
| 1996 | Crixivan | indinavir, IDV | Merck |
| 1997 | Viracept | nelfmavir mesylate, NFV | Pfizer |
| 1997 | Fortovase | saquinavir (no longer marketed) | Roche Pharmaceuticals |
| 1999 | Agenerase | amprenavir, APV | GlaxoSmithKline |
| 2000 | Kaletra | lopinavir + ritonavir, LPV/RTV | Abbott Laboratories |
| 2003 | Reyataz | atazanavir sulfate, ATV | Bristol-Myers Squibb |
| 2003 | Lexiva | fosamprenavir calcium, FOS-APV | GlaxoSmithKline |
| 2005 | Aptivus | tripranavir, TPV | Boehringer Ingelheim |
| 2006 | Prezista | Darunavir | Tibotec Therapeutics |
| Fusion Inhibitors | | | |
| 2003 | Fuzeon | Enfuvirtide, T-20 | Roche Pharmaceuticals & Trimeris |
| Entry Inhibitors | | | |
| 2007 | Selzentry | Maraviroc | Pfizer |
| Integrase Inhibitors | | | |
| 2007 | Isentress | Raltegravir | Merck |
| 2013 | Tivicay | Dolutegravir | ViiV Healthcare |
| — | — | Cabotegravir | |

The scope of combinations of compounds of this invention with HIV agents is not limited to those mentioned above, but includes in principle any combination with any pharmaceutical composition useful for the cure or treatment of HIV. As noted, in such combinations the compounds of the present invention and other HIV agents may be administered separately or in conjunction. In addition, one agent may be prior to, concurrent to, or subsequent to the administration of other agent(s).

Compounds of the present invention may be used in combination with one or more agents useful as pharmacological enhancers as well as with or without additional compounds for the prevention or treatment of HIV. Examples of such pharmacological enhancers (or pharmakinetic boosters) include, but are not limited to, ritonavir, GS-9350, and SPI-452. Ritonavir is 10-hydroxy-2-methyl-5-(1-methyethyl)-1-1 [2-(1-methylethyl)-4-thiazolyl]-3,6-dioxo-8,11-bis(phenylmethyl)-2,4,7,12-tetraazatridecan-13-oic acid, 5-thiazolylmethyl ester, [5S-(5S*,8R*,10R*,11R*)] and is available from Abbott Laboratories of Abbott park, Illinois, as Norvir. Ritonavir is an HIV protease inhibitor indicated with other antiretroviral agents for the treatment of HIV infection. Ritonavir also inhibits P450 mediated drug metabolism as well as the P-gycoprotein (Pgp) cell transport system, thereby resulting in increased concentrations of active compound within the organism. GS-9350 is a compound being developed by Gilead Sciences of Foster City Calif. as a pharmacological enhancer. SPI-452 is a compound being developed by *Sequoia* Pharmaceuticals of Gaithersburg, Md., as a pharmacological enhancer.

Provided herein are methods of treatment or prevention of autoimmune and inflammatory conditions and diseases that can be improved by inhibiting EZH1 and/or EZH2 and thereby, e.g., modulate the level of expression of methylation activated and methylation repressed target genes, or modulate the activity of signalling proteins. A method may comprise administering to a human, e.g. a human in need thereof, a therapeutically effective amount of an agent described herein.

Inflammation represents a group of vascular, cellular and neurological responses to trauma. Inflammation can be characterised as the movement of inflammatory cells such as monocytes, neutrophils and granulocytes into the tissues. This is usually associated with reduced endothelial barrier function and oedema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterised by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self tissues.

The aim of anti-inflammatory therapy is therefore to reduce this inflammation, to inhibit autoimmunity when present and to allow for the physiological process or healing and tissue repair to progress.

The agents may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knew, ankle, and foot, and conditions affecting tissues connecting muscles to bones such as tendons. Examples of musculoskeletal inflammation which may be treated with compounds of the invention include arthritis (including, for example, osteoarthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular inflammation refers to inflammation of any structure of the eye, including the eye lids. Examples of ocular inflammation which may be treated in this invention include blepharitis, blepharochalasis, conjunctivitis, dacryoadenitis, keratitis, keratoconjunctivitis sicca (dry eye), scleritis, trichiasis, and uveitis.

Examples of inflammation of the nervous system which may be treated in this invention include encephalitis, Guillain-Barre syndrome, meningitis, neuromyotonia, narcolepsy, multiple sclerosis, myelitis and schizophrenia.

Examples of inflammation of the vasculature or lymphatic system which may be treated in this invention include arthrosclerosis, arthritis, phlebitis, vasculitis, and lymphangitis.

Examples of inflammatory conditions of the digestive system which may be treated in this invention include cholangitis, cholecystitis, enteritis, enterocolitis, gastritis, gastroenteritis, ileitis, and proctitis.

Examples of inflammatory conditions of the reproductive system which may be treated in this invention include cervicitis, chorioamnionitis, endometritis, epididymitis, omphalitis, oophoritis, orchitis, salpingitis, tubo-ovarian abscess, urethritis, vaginitis, vulvitis, and vulvodynia.

The agents may be used to treat autoimmune conditions having an inflammatory component. Such conditions include acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome, Grave's disease, Guillain-Barre syndrome, Hashimoto's disease, Henoch-Schonlein purpura, Kawasaki's disease, lupus erythematosus, microscopic colitis, microscopic polyarteritis, mixed connective tissue disease, multiple sclerosis, myasthenia gravis, opsocionus myoclonus syndrome, optic neuritis, ord's thyroiditis, pemphigus, polyarteritis nodosa, polymyalgia, Reiter's syndrome, Sjogren's syndrome, temporal arteritis, Wegener's granulomatosis, warm autoimmune haemolytic anemia, interstitial cystitis, lyme disease, morphea, sarcoidosis, scleroderma, ulcerative colitis, and vitiligo.

The agents may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celliac disease).

Other inflammatory conditions which may be treated in this invention include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, astopic dermatitis, drug hypersensitivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis.

Preferred treatments include any one of treatment of transplant rejection, psoriatic arthritis, multiple sclerosis, Type 1 diabetes, asthma, systemic lupus erythematosis, chronic pulmonary disease, and inflammation accompanying infectious conditions (e.g., sepsis).

Pharmaceutical compositions may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the Formula (I), depending on the condition being treated, the route of administration and the age, weight and condition of the patient, or pharmaceutical compositions may be presented in unit dose forms containing a predetermined amount of active ingredient per unit dose. Preferred unit dosage compositions are those containing a daily dose or sub-dose, as herein above recited, or an appropriate fraction thereof, of an active ingredient. Furthermore, such pharmaceutical compositions may be prepared by any of the methods well known in the pharmacy art.

Pharmaceutical compositions may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association a compound of formal (I) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of a compound of Formula (I). Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit pharmaceutical compositions for oral administration can be microencapsulated. The formulation can also be prepared to prolong or sustain the release as for example by coating or embedding particulate material in polymers, wax or the like.

Pharmaceutical compositions adapted for rectal administration may be presented as suppositories or as enemas.

Pharmaceutical compositions adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The pharmaceutical compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the pharmaceutical compositions may include other agents conventional in the art having regard to the type of formulation in question, for example those suitable for oral administration may include flavoring agents.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, an effective amount of a compound of Formula (I) for the treatment of anemia will generally be in the range of 0.001 to 100 mg/kg body weight of recipient per day, suitably in the range of 0.01 to 10 mg/kg body weight per day. For a 70 kg adult mammal, the actual amount per day would suitably be from 7 to 700 mg and this amount may be given in a single dose per day or in a number (such as two, three, four, five or six) of sub-doses per day such that the total daily dose is the same. An effective amount of a salt or solvate, etc., may be determined as a proportion of the effective amount of the compound of Formula (I) per se. It is envisaged that similar dosages would be appropriate for treatment of the other conditions referred to above.

In certain embodiments, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one. In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one wherein at least 10% by weight of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is present as the crystalline form of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one (Form II) described herein. In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one wherein at least 20% by weight, or at least 30% by weight, or at least 40% by weight, or at least 50% by weight, or at least 60% by weight, or at least 70% by weight, or at least 80% by weight, or at least 90% by weight of the hydrochloric acid salt of (R)-5-((4,6-dimethyl-2-oxo-1,2-dihydropyridin-3-yl)methyl)-3-methyl-2-(1-neopentylpiperidin-4-yl)ethyl)-5,6,7,8-tetrahydro-4H-thieno[3,2-c]azepin-4-one is present as the crystalline form of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one (Form II) described herein. In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one wherein at least 95% by weight, or at least 96% by weight, or at least 97% by weight, or at least 98% by weight, or at least 99% by weight, or at least 99.5% by weight, or at least 99.8% by weight, or at least 99.9% by weight of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is present as the crystalline form of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one (Form II) described herein.

In certain embodiments, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one. In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one wherein at least 10% by weight of the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is present as the crystalline form of the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one (Form I) described herein. In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one wherein at least 20% by weight, or at least 30% by weight, or at least 40% by weight, or at least 50% by weight, or at least 60% by weight, or at least 70% by weight, or at least 80% by weight, or at least 90% by weight of the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is present as the crystalline form of the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one (Form I) described herein. In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one wherein at least 95% by weight, or at least 96% by weight, or at least 97% by weight, or at least 98% by weight, or at least 99% by weight, or at least 99.5% by weight, or at least 99.8% by weight, or at least 99.9% by weight of the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is present as the crystalline form of the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one (Form I) described herein.

In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one, wherein not more than 90% by weight of the salt is amorphous. In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one, wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of the salt is amorphous. In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one, wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of the salt is amorphous.

In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one, wherein not more than 90% by weight of the salt is amorphous. In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one, wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of the salt is amorphous. In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one, wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of the salt is amorphous.

In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one wherein not more than 90% by weight of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is present in a form other than the crystalline form of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one (Form II) described herein. In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one is present in a form other than the crystalline form of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one (Form II) described herein. In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of the hydrochloric acid salt of (R)-5-((4,6-dimethyl-2-oxo-1,2-dihydropyridin-3-yl)methyl)-3-methyl-2-(1-neopentylpiperidin-4-yl)ethyl)-5,6,7,8-tetrahydro-4H-thieno[3,2-c]azepin-4-one is present in a form other than the crystalline form of the hydrochloric acid salt of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one (Form II) described herein.

In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one wherein not more than 90% by weight of the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is present in a form other than the crystalline form of the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one (Form I) described herein. In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one wherein not more than 80% by weight, or not more than 70% by weight, or not more than 60% by weight, or not more than 50% by weight, or not more than 40% by weight, or not more than 30% by weight, or not more than 20% by weight, or not more than 10% by weight of the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is present in a form other than the crystalline form of the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one (Form I) described herein. In another embodiment, this invention relates to a pharmaceutical composition comprising the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one wherein not more than 5% by weight, or not more than 4% by weight, or not more than 3% by weight, or not more than 2% by weight, or not more than 1% by weight, or not more than 0.5% by weight, or not more than 0.2% by weight, or not more than 0.1% by weight of the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one is present in a form other than the crystalline form of the hydrochloric acid salt of (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one (Form I) described herein.

Definitions

Terms are used within their accepted meanings. The following definitions are meant to clarify, but not limit, the terms defined.

As used herein, the term "alkyl" represents a saturated, straight or branched hydrocarbon moiety having the specified number of carbon atoms. The term "$(C_1-C_4)$alkyl" refers to an alkyl moiety containing from 1 to 4 carbon atoms. Exemplary alkyls include, but are not limited to, methyl, ethyl, n-propyl, isopropyl, n-butyl, isobutyl, s-butyl, t-butyl, pentyl, hexyl, heptyl, and octyl.

"Alkoxy" refers to a group containing an alkyl radical, defined hereinabove, attached through an oxygen linking atom. The term "$(C_1-C_4)$alkoxy" refers to a straight- or branched-chain hydrocarbon radical having at least 1 and up to 4 carbon atoms attached through an oxygen linking atom. Exemplary "$(C_1-C_4)$alkoxy" groups useful in the present invention include methoxy, ethoxy, n-propoxy, isopropoxy, n-butoxy, s-butoxy, isobutoxy, and t-butoxy.

When the term "alkyl" is used in combination with other substituent groups, such as "halo$(C_1-C_5)$alkyl", "hydroxy$(C_1-C_5)$alkyl", or "$(C_1-C_4)$alkoxy$(C_1-C_5)$alkyl-", the term "alkyl" is intended to encompass a divalent straight or branched-chain hydrocarbon radical, wherein the point of attachment is through the alkyl moiety. The term "halo$(C_1-C_4)$alkyl" is intended to mean a radical having one or more halogen atoms, which may be the same or different, at one or more carbon atoms of an alkyl moiety containing from 1 to 4 carbon atoms, which is a straight or branched-chain carbon radical. Examples of "halo$(C_1-C_4)$alkyl" groups useful in the present invention include, but are not limited to, —$CF_3$ (trifluoromethyl), —$CCl_3$ (trichloromethyl), 1,1-difluoroethyl, 2-fluoro-2-methylpropyl, 2,2-difluoropropyl, 2,2,2-trifluoroethyl, and hexafluoroisopropyl. Examples of "hydroxy$(C_1-C_5)$alkyl" groups useful in the present invention include, but are not limited to, hydroxymethyl, hydroxyethyl, and hydroxyisopropyl. Examples of "$(C_1-C_4)$alkoxy$(C_1-C_5)$alkyl-" groups useful in the present invention include, but are not limited to, methoxymethyl, methoxyethyl, methoxyisopropyl, ethoxymethyl, ethoxyethyl, ethoxyisopropyl, isopropoxymethyl, isopropoxyethyl, isopropoxyisopropyl, t-butoxymethyl, t-butoxyethyl, and t-butoxyisopropyl.

As used herein, the term "cycloalkyl" refers to a non aromatic, saturated, cyclic hydrocarbon ring containing the specified number of carbon atoms. The term "$(C_3-C_5)$cycloalkyl" refers to a non aromatic cyclic hydrocarbon ring having from three to five ring carbon atoms. Exemplary "$(C_3-C_5)$cycloalkyl" groups useful in the present invention include cyclopropyl, cyclobutyl, and cyclopentyl.

As used herein, the term "bicycloalkyl" refers to a saturated, bridged, fused, or spiro, bicyclic hydrocarbon ring system containing the specified number of carbon atoms. Exemplary "$(C_6-C_{10})$bicycloalkyl" groups include, but are not limited to bicyclo[2.1.1]hexyl, bicyclo[2.1.1]heptyl, bicyclo[3.2.1]octyl, bicyclo[2.2.2]octyl, bicyclo[3.2.2]

nonyl, bicyclo[3.3.1]nonyl, bicyclo[3.3.2]decyl, bicyclo[4.3.1]decyl, bicyclo[2.2.0]hexyl, bicyclo[3.1.0]hexyl, bicyclo[3.2.0]heptyl, bicyclo[4.1.0]heptyl, octahydropentalenyl, bicyclo[4.2.0]octyl, decahydronaphthalenyl, spiro[3.3]heptyl, spiro[2.4]heptyl, spiro[3.4]octyl, spiro[2.5]octyl, spiro[4.4]nonyl, spiro[3.5]nonyl, and spiro[4.5]decyl.

The terms "halogen" and "halo" represent fluoro, chloro, bromo, or iodo substituents. "Hydroxy" or "hydroxyl" is intended to mean the radical —OH.

As used herein, the term "optionally" means that the subsequently described event(s) may or may not occur, and includes both event(s) that occur and event(s) that do not occur.

As used herein, the term "treatment" refers to alleviating the specified condition, eliminating or reducing one or more symptoms of the condition, slowing or eliminating the progression of the condition, and delaying the reoccurrence of the condition in a previously afflicted or diagnosed patient or subject.

"Cure" or "Curing" a disease in a patient is used to denote the eradication, stoppage, halt or end of the human immunodeficiency virus or symptoms, or the progression of the symptoms or virus, for a defined period. As an example, in one embodiment, "cure" or "curing" refers to a therapeutic administration or a combination of administrations that alone or in combination with one or more other compounds induces and maintains sustained viral control (undetectable levels of plasma viremia by, e.g., a polymerase chain reaction (PCR) test, a bDNA (branched chain DNA) test or a NASBA (nucleic acid sequence based amplification) test) of human immunodeficiency virus after a minimum of two years without any other therapeutic intervention. The above PCR, bDNA and NASBA tests are carried out using techniques known and familiar to one skilled in the art. As an example, the eradication, stoppage, halt or end of the human immunodeficiency virus or symptoms, or the progression of the symptoms or virus, may be sustained for a minimum of two years.

As used herein, the term "effective amount" means that amount of a drug or pharmaceutical agent that will elicit the biological or medical response of a tissue, system, animal, or human that is being sought, for instance, by a researcher or clinician.

The term "therapeutically effective amount" means any amount which, as compared to a corresponding subject who has not received such amount, results in improved treatment, healing, or amelioration of a disease, disorder, or side effect, or a decrease in the rate of advancement of a disease or disorder. The term also includes within its scope amounts effective to enhance normal physiological function. For use in therapy, therapeutically effective amounts of a compound of Formula (I), as well as salts thereof, may be administered as the raw chemical. Additionally, the active ingredient may be presented as a pharmaceutical composition.

Compound Preparation

Abbreviations

AcOH acetic acid
Ar Ar gas
Boc tert-butyloxycarbonyl
Bu$_4$NCl tetrabutylammonium chloride
CH$_3$CN acetonitrile
Cs$_2$CO$_3$ cesium carbonate
DCE 1,2-dichloroethane
DCM dichloromethane
DMF N,N-dimethylformamide
DMSO dimethyl sulfoxide
EDC 1-ethyl-3-(3-dimethylaminopropyl)carbodiimide
ES electrospray
Et$_2$O diethyl ether
EtOAc ethyl acetate
EtOH ethanol
h hour(s)
H$_2$ hydrogen gas
HCl hydrochloric acid
H$_2$O water
HOAt 1-hydroxy-7-azabenzotriazole
H$_2$SO$_4$ sulfuric acid
HPLC high-performance liquid chromatography
LCMS liquid chromatography mass spectrometry
LiAlH$_4$ lithium aluminum hydride
MeOH methanol
MgSO$_4$ magnesium sulfate
min minute(s)
M molar
MS mass spectrometry
N normal
N$_2$ nitrogen gas
NaBH$_4$ sodium borohydride
NaBH(OAc)$_3$ sodium triacetoxyborohydride
Na$_2$CO$_3$ sodium carbonate
NaHCO$_3$ sodium bicarbonate
NaHMDS sodium bis(trimethylsilyl)amide
NaOH sodium hydroxide
Na$_2$SO$_4$ sodium sulfate
NBS N-bromosuccinimide
NH$_4$Cl ammonium chloride
NH$_4$OAc ammonium acetate
NH$_4$OH ammonium hydroxide
NMM N-methylmorpholine
Pd(OAc)$_2$ palladium(II) acetate
Pd(PPh$_3$)$_4$ tetrakis(triphenylphosphine)palladium(0)
PLM polarized light microscopy
(R,R)-[COD]Ir[cy$_2$PThrePHOX]((4R,5R)-(+)—O-[1-benzyl-1-(5-methyl-2-phenyl-4,5-dihydrooxazol-4-yl)-2-phenylethyl](dicyclohexylphosphinite)(1,5-cyclooctadiene)iridium(I) tetrakis(3,5-bis(trifluoromethyl)phenylborate
r.t. room temperature
sat. saturated
TBME tert-butyl methyl ether
TFA trifluoroacetic acid
THF tetrahydrofuran Generic Synthesis Schemes The compounds of this invention may be made by a variety of methods, including well-known standard synthetic methods. Illustrative general synthetic methods are set out below and then specific compounds of the invention are prepared in the working examples. The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. In all of the schemes described below, protecting groups for sensitive or reactive groups are employed where necessary in accordance with general principles of synthetic chemistry. Protecting groups are manipulated according to standard methods of organic synthesis (T. W. Green and P.

G. M. Wuts, (1991) *Protecting Groups in Organic Synthesis*, John Wiley & Sons, incorporated by reference with regard to protecting groups). These groups are removed at a convenient stage of the compound synthesis using methods that are readily apparent to those skilled in the art. The selection of processes as well as the reaction conditions and order of their execution shall be consistent with the preparation of compounds of the present invention. Starting materials are commercially available or are made from commercially available starting materials using methods known to those skilled in the art.

Certain compounds of Formula (I) can be prepared according to Scheme 1 or analogous methods. An iridium-mediated borylation, followed by a Suzuki coupling with an appropriately substituted triflate gives the corresponding coupled olefin. An iridium-mediated asymmetric reduction of the olefin, followed by bromination provides the bromothiophene. A palladium-mediated Heck coupling of the bromothiophene with allyl alcohol, followed by a reductive amination of the resultant aldehyde with an appropriately substituted amine furnishes the secondary amine. Saponification of the ester and intramolecular amide formation affords the elaborated thiophenelactam. Removal of the methyl and tert-butylcarbonyl protecting groups provides the pyridone. Reductive amination with an appropriately substituted aldehyde affords compounds of Formula (I).

Scheme 1: Synthesis Compounds of Formula (I).

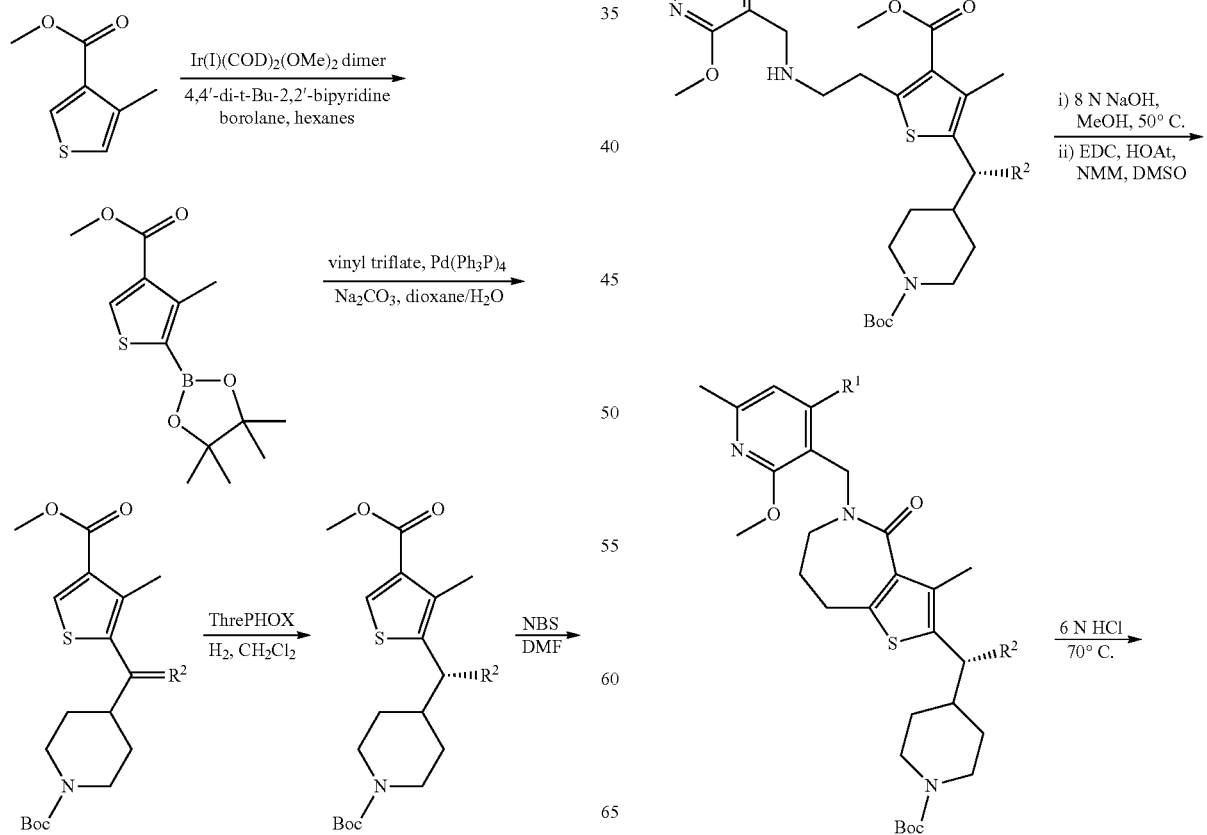

-continued

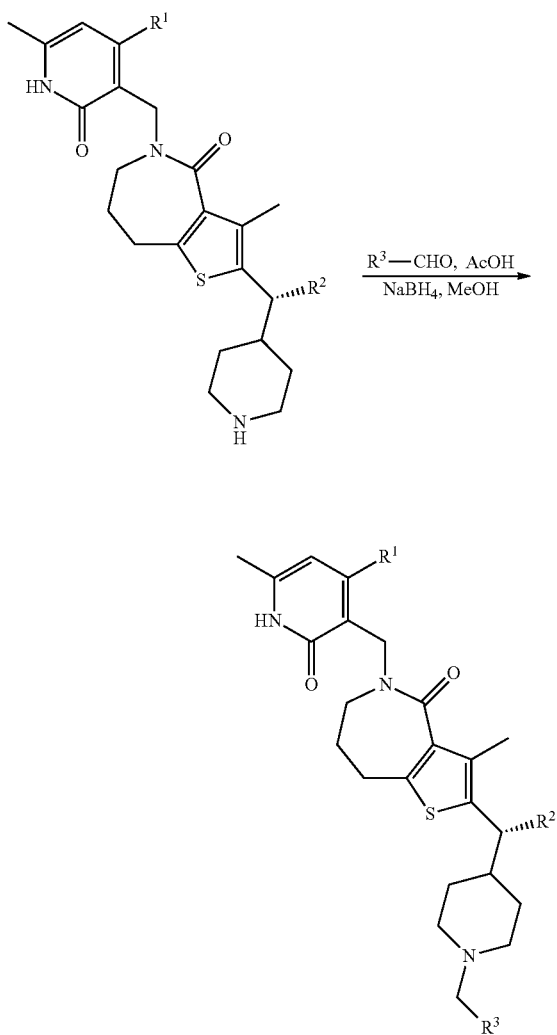

EXPERIMENTALS

The following guidelines apply to all experimental procedures described herein. All reactions were conducted under a positive pressure of nitrogen using oven-dried glassware, unless otherwise indicated. Temperatures designated are external (i.e. bath temperatures), and are approximate. Air and moisture-sensitive liquids were transferred via syringe. Reagents were used as received. Solvents utilized were those listed as "anhydrous" by vendors. Molarities listed for reagents in solutions are approximate, and were used without prior titration against a corresponding standard. All reactions were agitated by stir bar, unless otherwise indicated. Heating was conducted using heating baths containing silicon oil, unless otherwise indicated. Reactions conducted by microwave irradiation (0-400 W at 2.45 GHz) were done so using a Biotage® Initiator 2.0 instrument with Biotage® microwave EXP vials (0.2-20 mL) and septa and caps. Irradiation levels utilized (i.e. high, normal, low) based on solvent and ionic charge were based on vendor specifications. Cooling to temperatures below −70° C. was conducted using dry ice/acetone or dry ice/2-propanol. Magnesium sulfate and sodium sulfate used as drying agents were of anhydrous grade, and were used interchangeably. Solvents described as being removed "in vacuo" or "under reduced pressure" were done so by rotary evaporation.

Preparative normal phase silica gel chromatography was carried out using either a Teledyne ISCO® CombiFlash Companion instrument with RediSep or ISCO® Gold silica gel cartridges (4 g-330 g), or an Analogix® IF280 instrument with SF25 silica gel cartridges (4 g-3-00 g), or a Biotage® SP1 instrument with HP® silica gel cartridges (10 g-100 g). Purification by reverse phase HPLC was conducted using a YMC-pack column (ODS-A 75×30 mm) as solid phase, unless otherwise noted. A mobile phase of 25 mL/min A ($CH_3CN$-0.1% TFA): B (water-0.1% TFA), 10-80% gradient A (10 min) was utilized with UV detection at 214 nM, unless otherwise noted.

A PE Sciex® API 150 single quadrupole mass spectrometer (PE Sciex, Thornhill, Ontario, Canada) was operated using electrospray ionization in the positive ion detection mode. The nebulizing gas was generated from a zero air generator (Balston Inc., Haverhill, Mass., USA) and delivered at 65 psi and the curtain gas was high purity nitrogen delivered from a Dewar liquid nitrogen vessel at 50 psi. The voltage applied to the electrospray needle was 4.8 kV. The orifice was set at 25 V and mass spectrometer was scanned at a rate of 0.5 scan/sec using a step mass of 0.2 amu and collecting profile data.

Method A LCMS. Samples were introduced into the mass spectrometer using a CTC® PAL autosampler (LEAP Technologies, Carrboro, N.C.) equipped with a Hamilton® 10 uL syringe which performed the injection into a Valco 10-port injection valve. The HPLC pump was a Shimadzu® LC-10ADvp (Shimadzu Scientific Instruments, Columbia, Md.) operated at 0.3 mL/min and a linear gradient 4.5% A to 90% B in 3.2 min. with a 0.4 min. hold. The mobile phase was composed of 100% ($H_2O$ 0.02% TFA) in vessel A and 100% ($CH_3CN$ 0.018% TFA) in vessel B. The stationary phase is Aquasil® (C18) and the column dimensions were 1 mm×40 mm. Detection was by UV at 214 nm, evaporative light-scattering (ELSD) and MS.

Method B, LCMS. Alternatively, an Agilent® 1100 analytical HPLC system with an LC/MS was used and operated at 1 mL/min and a linear gradient 5% A to 100% B in 2.2 min with a 0.4 min hold. The mobile phase was composed of 100% ($H_2O$ 0.02% TFA) in vessel A and 100% ($CH_3CN$ 0.018% TFA) in vessel B. The stationary phase was Zobax® (C8) with a 3.5 um partical size and the column dimensions were 2.1 mm×50 mm. Detection was by UV at 214 nm, evaporative light-scattering (ELSD) and MS.

Method C, LCMS. Alternatively, an MDSSCIEX® API 2000 equipped with a capillary column of (50×4.6 mm, 5 μm) was used. HPLC was done on Agilent® 1200 series UPLC system equipped with column Zorbax® SB-$C_{18}$ (50×4.6 mm, 1.8 μm) eluting with $CH_3CN$:$NH_4OAc$ buffer.

$^1$H-NMR spectra were recorded at 400 MHz using a Bruker® AVANCE 400 MHz instrument, with ACD Spect manager v. 10 used for reprocessing. Multiplicities indicated are: s=singlet, d=doublet, t-triplet, q=quartet, quint=quintet, sxt=sextet, m=multiplet, dd=doublet of doublets, dt=doublet of triplets etc. and br indicates a broad signal. All NMRs in DMSO-$d_6$ unless otherwise noted.

Analytical HPLC: Products were analyzed by Agilent® 1100 Analytical Chromatography system, with 4.5×75 mm Zorbax® XDB-C18 column (3.5 um) at 2 mL/min with a 4 min gradient from 5% $CH_3CN$ (0.1% formic acid) to 95% $CH_3CN$ (0.1% formic acid) in $H_2O$ (0.1% formic acid) and a 1 min hold.

Intermediates

Intermediate 1

Methyl 4-methylthiophene-3-carboxylate

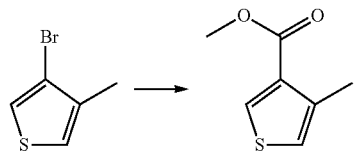

To a stirred solution of 3-bromo-4-methylthiophene (20.0 g, 113 mmol) in THF (100 mL) under nitrogen at RT was added isopropylmagnesium chloride lithium chloride complex 1.3 N in THF (90 mL, 117 mmol) dropwise. The reaction was stirred overnight. The reaction was cooled to −78° C. and treated with methyl chloroformate (12 mL, 155 mmol). The reaction was allowed to warm to RT and stirred for 1 hr. The reaction was diluted with EtOAc, washed with saturated $NaHCO_3$, stirred for 30 min, (formed a white suspension that stayed in the aqueous phase), washed with brine, dried ($Na_2SO_4$), filtered and concentrated under vacuum. The product was short path distilled under vacuum (4 to 2 mm Hg) at 44 to 50° C. (oil bath 50 to 75° C.). The main and late fractions were combined to give the product methyl 4-methylthiophene-3-carboxylate (13.2 g, 85 mmol, 74.8% yield) as a clear liquid. MS(ES) [M+H]$^+$ 156.8.

Alternatively, Intermediate 1 was prepared as follows:

To a stirred solution of 3-bromo-4-methylthiophene (250 g, 1412 mmol) in THF (1200 mL) under nitrogen at r.t. was added a solution of isopropylmagnesium chloride lithium chloride complex (1.3 M in THF) (1086 mL, 1412 mmol) dropwise during 1 hour. The reaction mixture was stirred at r.t. overnight under a nitrogen atmosphere. The next day, the reaction was cooled to −78° C. in a dry ice/acetone bath and treated with methyl chloroformate (153 mL, 1977 mmol). The reaction was allowed to warm to r.t. and stirred for 3 h. The reaction mixture was then diluted with $Et_2O$ (750 mL) and stirred with sat. $NaHCO_3$ (300 mL) for 20 min. The aqueous layer was again extracted with $Et_2O$ (2×250 mL). The combined organic layers were washed with brine (250 mL), dried ($Na_2SO_4$), filtered and concentrated under vacuum to afford crude compound (239 g) as pale yellow liquid. The crude product was purified by short path distillation under vacuum (~3 mm Hg). The product distilled at 50-55° C. using a heating mantle. The forerun, main fraction and late fraction were collected. Main fraction and late fraction were subsequently combined to afford product containing a less polar impurity. The residue was then chromatographed on a silica gel column eluting with a gradient of 0-20% $Et_2O$/hexanes. The fractions corresponding to product by TLC were combined and concentrated under reduced pressure to afford methyl 4-methylthiophene-3-carboxylate (194 g, 1242 mmol, 88% yield) at ~90% purity as a light yellow oil. $^1H$ NMR (400 MHz, $CDCl_3$) δ 8.08 (d, J=3.5 Hz, 1H), 6.94-6.89 (m, 1H), 3.85 (s, 3H), 2.48 (d, J=1.0 Hz, 3H). MS(ES) [M+H]$^+$ 156.9.

Intermediate 2

(2-Methoxy-4,6-dimethylpyridin-3-yl)methanamine

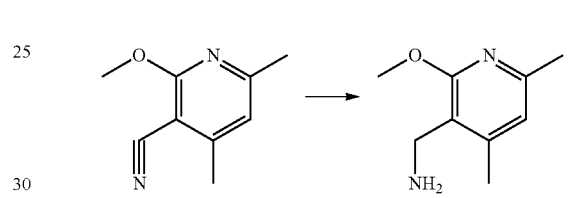

To a cooled (ice water bath) solution of 2-methoxy-4,6-dimethylnicotinonitrile (10 g, 61.7 mmol) in $Et_2O$ (200 mL) was added dropwise 1 M $LiAlH_4$ in $Et_2O$ (123 mL, 123 mmol). The ice bath was removed and the reaction mixture was stirred at r.t. for 16 h. The reaction mixture was cooled in an ice water bath and quenched with a minimum amount of water (until no more hydrogen was generated). The reaction was filtered and the insoluble material was washed with 10:1 DCM/MeOH. The combined organic filtrates were concentrated. The residue was purified via column chromatography (0-30% MeOH/DCM; 100 g-HP-silica gel column) to give (2-methoxy-4,6-dimethylpyridin-3-yl)methanamine (8.9 g) as a yellowish semi-solid.

Alternatively, Intermediate 2 was prepared as follows:

To a cooled (ice water bath) suspension of 2-methoxy-4,6-dimethylnicotinonitrile (50 g, 308 mmol) in $Et_2O$ (1000 mL) was added dropwise 2 M $LiAlH_4$ in THF (308 mL, 617 mmol) over 30 min. The reaction was stirred for 60 min, at which time the ice bath was removed. The reaction mixture was stirred at r.t. for 20 h. The reaction mixture was re-cooled (ice water bath) and quenched dropwise with $H_2O$ (25 mL), followed by 3 M NaOH (25 mL) and more $H_2O$ (75 mL). The cooling bath was removed and $MgSO_4$ (10 heaping scoops) was added. The mixture was stirred for 1 h, at which time it was filtered through Celite®. The solids were washed with $Et_2O$ and the mother liquors were concentrated. The residue was dried under vacuum (hivac) for 2 h to give (2-methoxy-4,6-dimethylpyridin-3-yl)methanamine (50 g, 98% yield) as a yellow oil which solidified upon freezing. MS(ES) [M+H]$^+$ 167.0.

EXAMPLES

Example 1

(R)-5-((4,6-Dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one

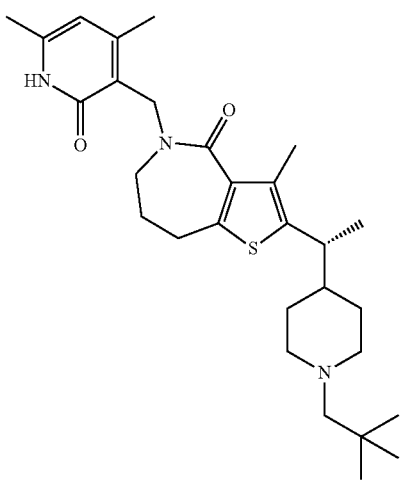 [SMILES: Cc1cc(C)c(CN2CCCc3sc([C@H](C)C4CCN(CC(C)(C)C)CC4)c(C)c3C2=O)c(=O)[nH]1]

a) Methyl 4-methyl-5-(4,4,5,5-tetramethyl-1,3,2-dioxaborolan-2-yl)thiophene-3-carboxylate

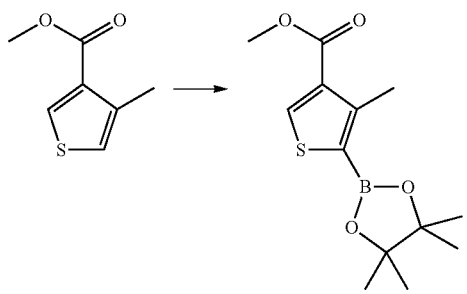

To a 500 mL round-bottom flask under Ar was added (1,5-cyclooctadiene)(methoxy)iridium(I) dimer (1.3 g, 1.961 mmol). With stirring, 4,4,5,5-tetramethyl-1,3,2-dioxaborolane (32 mL, 222 mmol) was added via syringe followed by a solution of 4,4'-di-tert-butyl-2,2'-dipyridyl (1.04 g, 3.87 mmol) in n-hexane (75 mL) (the reaction was kept cool 5-10° C. in a ice bath). After stirring for 1 minute, methyl 4-methylthiophene-3-carboxylate (20.0 g, 128 mmol) was added (gas evolution seen). The reaction was stirred overnight at r.t. The reaction was evaporated to dryness under vacuum and purified by silica gel chromatography (Isco® RediSep Rf Gold 330 g, 0 to 10% EtOAc in hexanes). The pure fractions were combined and evaporated to dryness to give methyl 4-methyl-5-(4,4,5,5-tetramethyl-1,3,2-dioxaborolan-2-yl)thiophene-3-carboxylate (33.1 g, 117 mmol, 92% yield) as a colorless oil, which solidified to a waxy white solid under vacuum. MS(ES) [M+H]$^+$ 200.9 (boronic acid), 283.1 (boronate).

b) tert-Butyl 4-(1-(((trifluoromethyl)sulfonyl)oxy)vinyl)piperidine-1-carboxylate

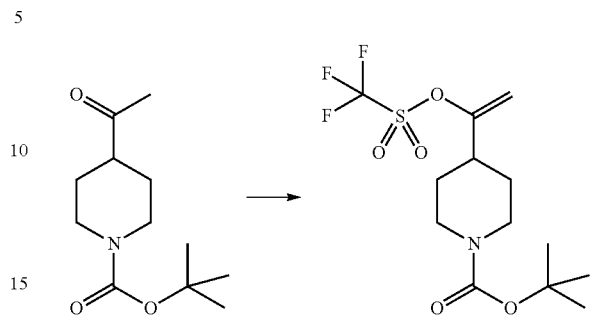

To a stirred solution of tert-butyl 4-acetylpiperidine-1-carboxylate (25 g, 110 mmol) in THF (250 mL) at −78° C. under nitrogen was added dropwise 1 N NaHMDS in THF (130 mL, 130 mmol). The reaction was stirred at −78° C. for 1 h. A solution of 1,1,1-trifluoro-N-(pyridin-2-yl)-N-((trifluoromethyl)sulfonyl)methanesulfonamide (45 g, 126 mmol) in THF (100 mL) was next added dropwise over 15 min. The reaction was stirred for 1 h at −78° C., then at 0° C. for 30 min. The reaction was quenched with cold water (500 mL), extracted with EtOAc (2×250 mL), washed with brine, dried (Na$_2$SO$_4$), filtered and concentrated under vacuum. The crude product was purified by silica gel chromatography (Isco® RediSep Rf Gold 330 g, 0 to 20% EtOAc in hexanes). (UV negative, visualized by charring with H$_2$SO$_4$ in EtOH.) The fractions containing product were combined and evaporated to dryness to give tert-butyl 4-(1-(((trifluoromethyl)sulfonyl)oxy)vinyl)piperidine-1-carboxylate (29.1 g, 81 mmol, 73.6% yield) as a colorless oil. (LCMS and $^1$H NMR showed ~16% of N-Boc-4-ethynylpiperidine) MS(ES) [M+H]$^+$304.0 (-isobutylene), 283.1 (-Boc).

c) tert-Butyl 4-(1-(4-(methoxycarbonyl)-3-methylthiophen-2-yl)vinyl)piperidine-1-carboxylate

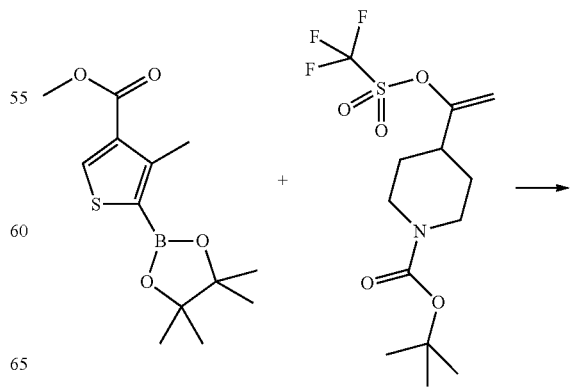

-continued

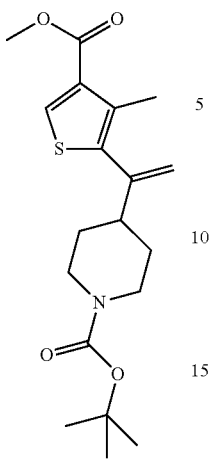

A stirred solution of methyl 4-methyl-5-(4,4,5,5-tetramethyl-1,3,2-dioxaborolan-2-yl)thiophene-3-carboxylate (50 g, 177 mmol), tert-butyl 4-(1-(((trifluoromethyl)sulfonyl)oxy)vinyl)piperidine-1-carboxylate (76 g, 211 mmol) and Na$_2$CO$_3$ (45 g, 536 mmol) in 1,4-dioxane (450 mL) and water (150 mL) was purged with N$_2$ by bubbling for 5 min. The reaction was charged with Pd(PPh$_3$)$_4$ (8 g, 6.92 mmol) and heated at 70° C. under N$_2$ for 1 h (vigourous gas evolution). The reaction was diluted with EtOAc (500 mL), washed with water (500 mL) and brine, dried (Na$_2$SO$_4$), and concentrated under vacuum. The residue was purified by silica gel chromatography (Isco® RediSep Rf Gold 330 g, 0 to 20% EtOAc/hexanes) to give tert-butyl 4-(1-(4-(methoxycarbonyl)-3-methylthiophen-2-yl)vinyl)piperidine-1-carboxylate (58.8 g, 161 mmol, 91% yield) as a light yellow oil. MS(ES) [M+H]$^+$ 266.1 (-Boc), [M+H]$^+$ 278.0 (-isobutylene, -MeOH), [M+H]$^+$ 310.1 (-isobutylene), [M+Na]$^+$388.1.

d) (R)-tert-Butyl 4-(1-(4-(methoxycarbonyl)-3-methylthiophen-2-yl)ethyl)piperidine-1-carboxylate

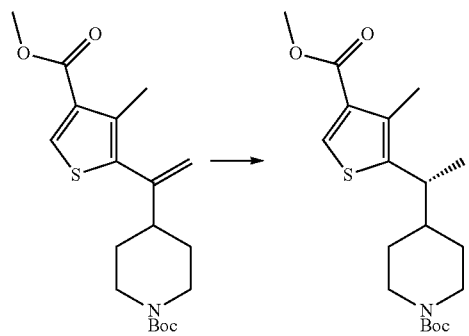 [SMILES: C=C(c1scc(C(=O)OC)c1C)C1CCN(C(=O)OC(C)(C)C)CC1 ; COC(=O)c1csc([C@H](C)C2CCN(C(=O)OC(C)(C)C)CC2)c1C]

A solution of tert-butyl 4-(1-(4-(methoxycarbonyl)-3-methylthiophen-2-yl)vinyl)piperidine-1-carboxylate (31.0 g, 85 mmol) in DCM (500 mL) was purged with a N$_2$ stream for 10 min. To the purged solution was added (R,R)-[COD]Ir[cy$_2$PThrePHOX](2.64 g, 1.527 mmol). The mixture was charged with H$_2$ (50 psi) and shaken (Parr reactor) for 22 h, at which time it was filtered through Celite®, washed with DCM (50 mL), and concentrated. Purification of the residue (330 gram Isco® silica column; gradient B: 3-30%; A=heptane; B=EtOAc) gave (R)-tert-butyl 4-(1-(4-(methoxycarbonyl)-3-methylthiophen-2-yl)ethyl)piperidine-1-carboxylate (30.9 g, 80 mmol, 94% yield) as a thick oil. MS(ES) [M+H]$^+$ 390.2. The optical purity of the product was determined to be 97.6% ee by chiral HPLC (Chiralpak AY-H, 5 microns, 4.6 mm×150 mm; 245, 250 nm UV; 90:10:0.1 n-heptane:EtOH:isopropylamine, isocratic, 1.0 mL/min). The absolute configuration was confirmed by small molecule X-ray crystallography of the L-(+)-tartaric acid salt of the corresponding Boc-deprotected amine.

e) (R)-tert-Butyl 4-(1-(5-bromo-4-(methoxycarbonyl)-3-methylthiophen-2-yl)ethyl)piperidine-1-carboxylate

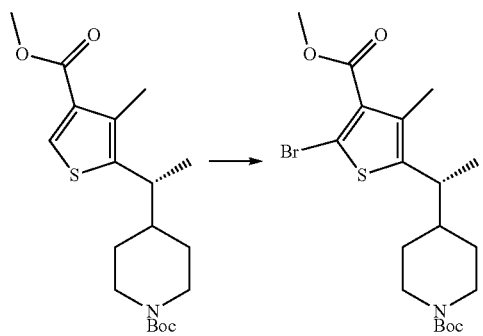 [SMILES: COC(=O)c1csc([C@H](C)C2CCN(C(=O)OC(C)(C)C)CC2)c1C ; COC(=O)c1c(Br)sc([C@H](C)C2CCN(C(=O)OC(C)(C)C)CC2)c1C]

To a solution of (R)-tert-butyl 4-(1-(4-(methoxycarbonyl)-3-methylthiophen-2-yl)ethyl)piperidine-1-carboxylate (33.2 g, 90 mmol) in DMF (500 mL) was added NBS (20.9 g, 117 mmol). The reaction was maintained for approximately 4 h, at which time it was diluted with water and extracted with Et$_2$O (1.5 L). The organics were washed with water, brine, dried over MgSO$_4$, filtered and evaporated. Purification of the residue by column chromatography (5 to 20% EtOAc/hexanes) gave (R)-tert-butyl 4-(1-(5-bromo-4-(methoxycarbonyl)-3-methylthiophen-2-yl)ethyl)piperidine-1-carboxylate (34 g, 72.4 mmol, 80% yield). MS(ES) [M+H]$^+$ 468.2, 470.2 (M+Na).

f) (R)-tert-Butyl 4-(1-(4-(methoxycarbonyl)-3-methyl-5-(3-oxopropyl)thiophen-2-yl)ethyl)piperidine-1-carboxylate

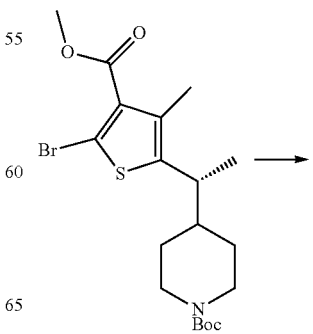

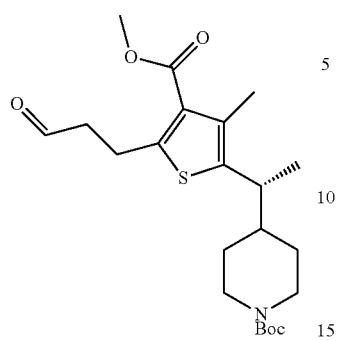

To a solution of (R)-tert-butyl 4-(1-(5-bromo-4-(methoxycarbonyl)-3-methylthiophen-2-yl)ethyl)piperidine-1-carboxylate (50 g, 112 mmol) in DMF (1 L) were added prop-2-en-1-ol (0.023 L, 560 mmol), Bu₄NCl (37.4 g, 134 mmol) and NaHCO₃ (37.6 g, 448 mmol). The reaction mixture was degassed with N₂ and Pd(OAc)₂ (3.77 g, 16.8 mmol) was added. The reaction mixture was heated at 65° C. for 2 h, at which time it allowed to cool to rt. The mixture was diluted with water (1.3 L) and extracted with Et₂O (2×). The combined extracts were dried (MgSO₄) and concentrated. The residue was purified by column chromatography (silica gel, 10 to 40% EtOAc/hexanes) to give (R)-tert-butyl 4-(1-(4-(methoxycarbonyl)-3-methyl-5-(3-oxopropyl)thiophen-2-yl)ethyl)piperidine-1-carboxylate (42 g, 94 mmol, 84% yield) as a pale yellow oil. MS(ES) [M+H]⁺ 446.2 (M+Na) 464.3 (M+MeCN).

g) (R)-tert-Butyl 4-(1-(5-(3-(((2-methoxy-4,6-dimethylpyridin-3-yl)methyl)amino)propyl)-4-(methoxycarbonyl)-3-methylthiophen-2-yl)ethyl)piperidine-1-carboxylate

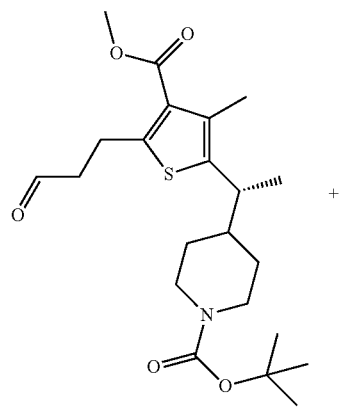

+

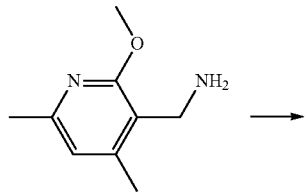

To a solution of (R)-tert-butyl 4-(1-(4-(methoxycarbonyl)-3-methyl-5-(3-oxopropyl)thiophen-2-yl)ethyl)piperidine-1-carboxylate (36.3 g, 86 mmol) in MeOH (600 mL) was added (2-methoxy-4,6-dimethylpyridin-3-yl)methanamine (16.38 g, 99 mmol) as a frozen solid. The reaction was maintained at r.t. for 1.5 h. The reaction was then cooled in an ice bath for 10 min, at which time NaBH₄ (8.11 g, 214 mmol) was added as a solid (some foaming/gas evolution). The mixture was stirred for 15 min. The ice bath was removed and the reaction was stirred at r.t. for 2 h. The reaction was recooled in an ice bath and quenched with sat. aqueous NH₄Cl (200 mL). The ice bath was removed and the reaction was concentrated in vacuo to ~¼ volume. The mixture was diluted with sat. aqueous NH₄Cl and extracted with EtOAc (2×). The combined organics were washed with sat. aqueous NH₄Cl, dried over MgSO₄ (stirred for 15 min), filtered through Celite®, and concentrated to give (R)-tert-butyl 4-(1-(5-(3-(((2-methoxy-4,6-dimethylpyridin-3-yl)methyl)amino)propyl)-4-(methoxycarbonyl)-3-methylthiophen-2-yl)ethyl)piperidine-1-carboxylate (55.5 g, 87 mmol based on 90% purity by HPLC, 100% yield) as an oil. The material was dried in vacuo for 30 min. MS(ES) [M+H]⁺ 574.5.

53 h) (R)-5-(1-(1-(tert-Butoxycarbonyl)piperidin-4-yl)ethyl)-2-(3-(((2-methoxy-4,6-dimethylpyridin-3-yl)methyl)amino)propyl)-4-methylthiophene-3-carboxylic acid

54 i) (R)-tert-Butyl 4-(1-(5-((2-methoxy-4,6-dimethylpyridin-3-yl)methyl)-3-methyl-4-oxo-5,6,7,8-tetrahydro-4H-thieno[3,2-c]azepin-2-yl)ethyl)piperidine-1-carboxylate

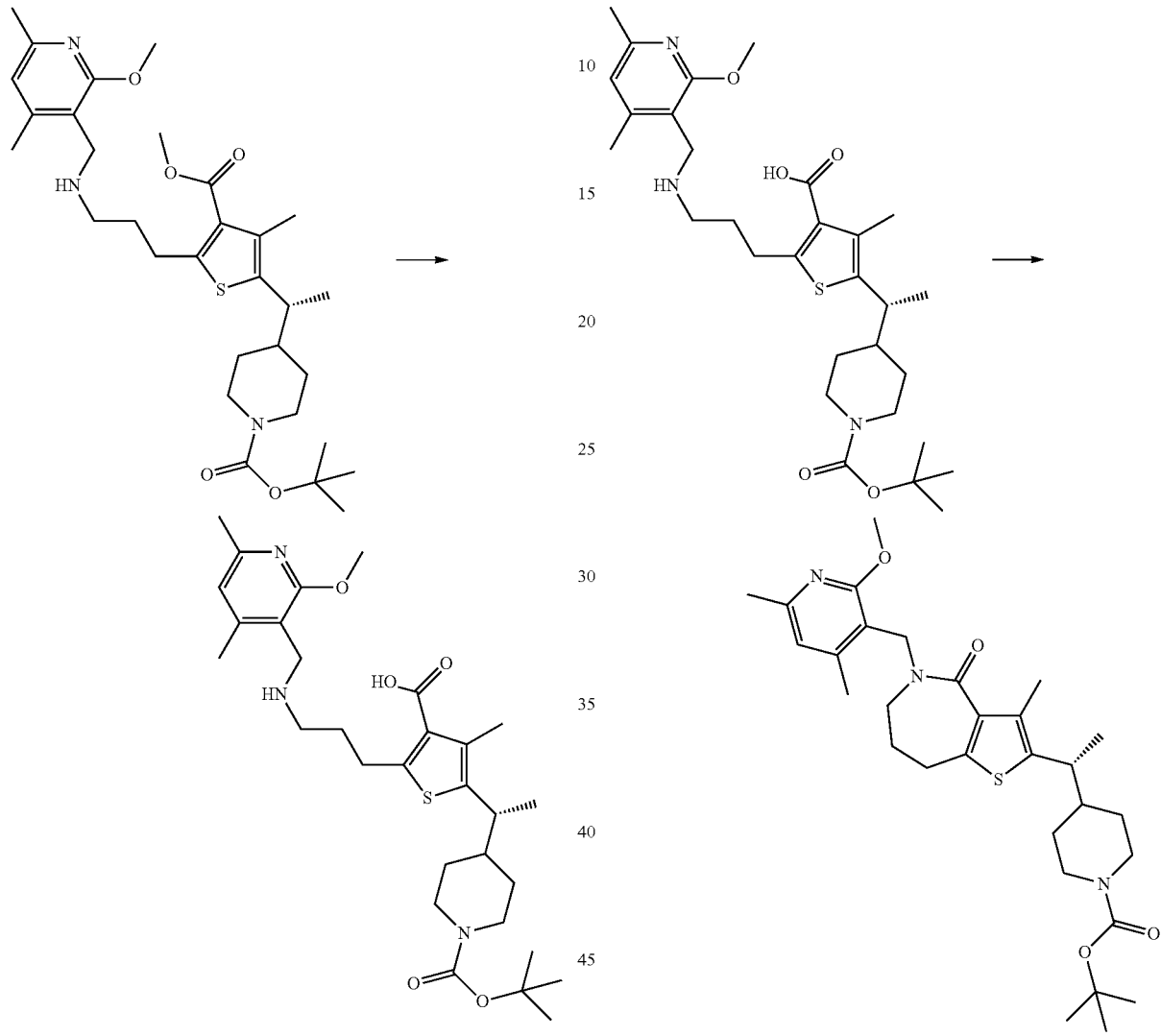

To a solution of (R)-tert-butyl 4-(1-(5-(3-(((2-methoxy-4,6-dimethylpyridin-3-yl)methyl)amino)propyl)-4-(methoxycarbonyl)-3-methylthiophen-2-yl)ethyl)piperidine-1-carboxylate (55 g, 96 mmol) in MeOH (600 mL) and THF (130 mL) was added 5 N NaOH (192 mL, 959 mmol). The reaction was heated at 63° C. for 22 h, at which time it was concentrated in vacuo. The residue was diluted with water (400 mL) and DCM (400 mL) and cooled in an ice bath. To the mixture was added 6 N HCl (158 mL, 949 mmol) to adjust the pH to 5-6 (paper). The mixture was stirred well and the layers were separated. The aqueous layer was extracted with DCM (200 mL) and the combined organics were dried over MgSO₄ (stirred for 30 min), filtered through Celite® and concentrated to give (R)-5-(1-(1-(tert-butoxycarbonyl)piperidin-4-yl)ethyl)-2-(3-(((2-methoxy-4,6-dimethylpyridin-3-yl)methyl)amino)propyl)-4-methylthiophene-3-carboxylic acid (52.5 g, 87 mmol, 91% yield). The residue was dried in vacuo for 2 h. MS(ES) [M+H]⁺ 560.4.

To a solution of (R)-5-(1-(1-(tert-butoxycarbonyl)piperidin-4-yl)ethyl)-2-(3-(((2-methoxy-4,6-dimethylpyridin-3-yl)methyl)amino)propyl)-4-methylthiophene-3-carboxylic acid (52.5 g, 94 mmol), EDC (21.58 g, 113 mmol) and HOAt (15.32 g, 113 mmol) in DMSO (400 mL) was added NMM (25.8 mL, 234 mmol). The reaction was maintained for 18 h, at which time it was poured slowly into ice water (1500 mL). The mixture was vigorously stirred (overhead stirrer) for 40 min. The mixture was filtered and the solids were washed with water and air-dried for ~1 h. The still wet solid was dissolved in DCM and washed with sat. aqueous NH₄Cl, dried (Mg₂SO₄), filtered through Celite®, and concentrated. Purification of the residue by column chromatography (330 g Isco® silica column; gradient B: 4-40%; A=heptane. B=3:1 EtOAc/EtOH) gave (R)-tert-butyl 4-(1-(5-((2-methoxy-4,6-dimethylpyridin-3-yl)methyl)-3-methyl-4-oxo-5,6,7,8-tetrahydro-4H-thieno[3,2-c]azepin-2- yl)ethyl)piperidine-1-carboxylate (34.3 g, 60 mmol, 64% yield) as a glassy yellow solid. MS(ES) [M+H]+ 542.4.

j) (R)-5-((4,6-Dimethyl-2-oxo-1,2-dihydropyridin-3-yl)methyl)-3-methyl-2-(1-(piperidin-4-yl)ethyl)-5,6,7,8-tetrahydro-4H-thieno[3,2-c]azepin-4-one

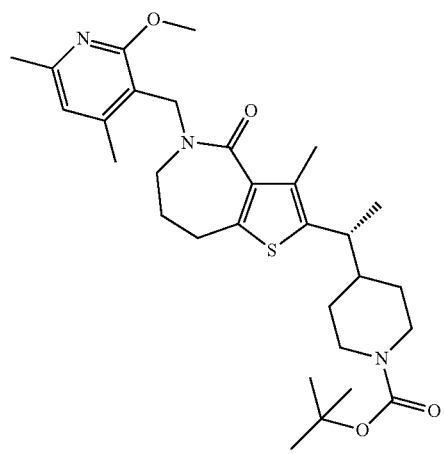

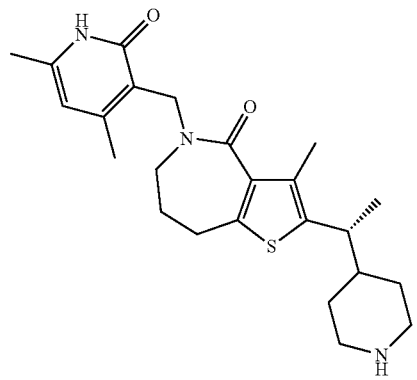

To a solution of (R)-tert-butyl 4-(1-(5-((2-methoxy-4,6-dimethylpyridin-3-yl)methyl)-3-methyl-4-oxo-5,6,7,8-tetrahydro-4H-thieno[3,2-c]azepin-2-yl)ethyl)piperidine-1-carboxylate (34.3 g, 63.3 mmol) in MeOH (450 mL) was added 4 N HCl in 1,4-dioxane (222 mL, 886 mmol). The reaction was maintained for 15 min at r.t., then heated at 70° C. for 24 h. The reaction was allowed to cool to r.t. and concentrated. The residue was diluted with DCM (500 mL) and water (300 mL) and the pH was adjusted to approximately 11 with concentrated NH₄OH. The mixture was stirred for 15 min, at which time the layers were separated. The aqueous layer was extracted with DCM and the combined organics were dried (Mg₂SO₄), filtered, and concentrated. The residue was dried in vacuo for 18 h to give (R)-5-((4,6-dimethyl-2-oxo-1,2-dihydropyridin-3-yl)methyl)-3-methyl-2-(1-(piperidin-4-yl)ethyl)-5,6,7,8-tetrahydro-4H-thieno[3,2-c]azepin-4-one (29.3 g, 65.1 mmol, 100% yield). MS(ES) [M+H]+ 428.3.

k) (R)-5-((4,6-Dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one

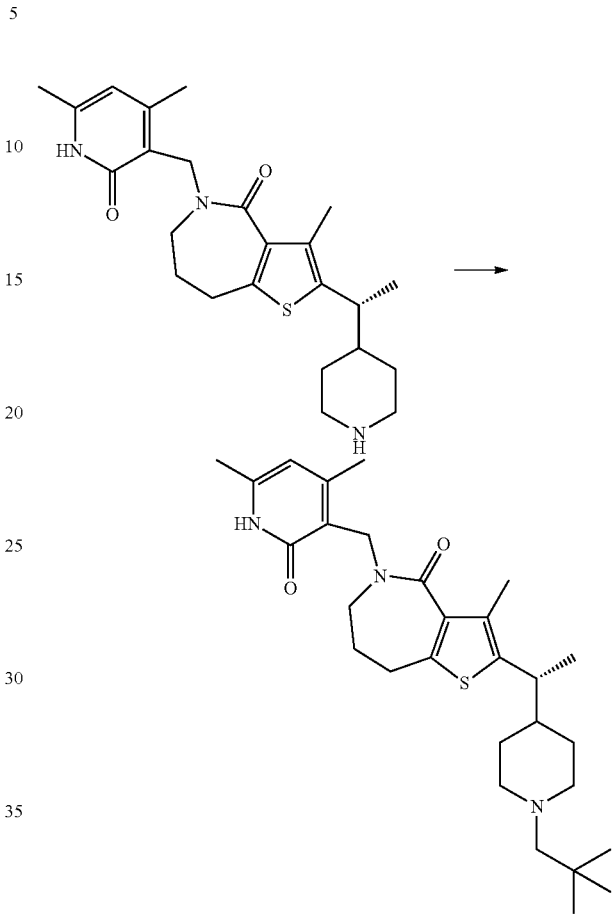

To a solution of (R)-5-((4,6-dimethyl-2-oxo-1,2-dihydropyridin-3-yl)methyl)-3-methyl-2-(1-(piperidin-4-yl)ethyl)-5,6,7,8-tetrahydro-4H-thieno[3,2-c]azepin-4-one (1.15 g, 2.69 mmol) in DCE (30 mL) was added pivalaldehyde (0.747 mL, 6.72 mmol). The reaction was stirred for 5 min, at which time AcOH (0.308 mL, 5.38 mmol) was added. After 15 min, NaBH(OAc)₃ (1.710 g, 8.07 mmol) was added as a solid and the reaction was stirred at r.t. for 18 h. The reaction was diluted with DCM (20 mL) and H₂O. The pH was adjusted to 10 with a combination of sat. NaHCO₃ and sat. Na₂CO₃. The mixture was stirred for 30 min and the layers were separated. The aqueous layer was extracted with DCM and the combined organics were dried over Mg₂SO₄, filtered and concentrated. The residue was purified by column chromatography (40 g Isco® silica column; gradient B: 15-90%; A=heptane; B=3:1 EtOAc/EtOH+1% NH₄OH). The purified residue was treated with DCM and concentrated. The residue was then treated with TBME and concentrated (2×). The solid was further dried in a vacuum oven at 45° C. for 4 h to give (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one (912 mg, 1.777 mmol, 66.1% yield). ¹H NMR (DMSO-d₆) δ 11.58 (s, 1H), 5.91 (s, 1H), 4.61 (d, J=13.7 Hz, 1H), 4.50 (d, J=13.4 Hz, 1H), 3.16-3.28 (m, 2H), 2.75-2.90 (m, 2H), 2.62-2.73 (m, 3H), 1.93-2.20 (m, 13H), 1.74 (d, J=8.9 Hz, 1H), 1.65 (quin, J=6.7 Hz, 2H), 1.33 (d, J=9.4 Hz, 1H), 1.11-1.28 (m, 7H), 0.81 (s, 9H). MS(ES) [M+H]+ 498.4.

Alternatively, the compound of Example 1 was prepared as follows:

a') Methyl 4-methyl-5-(4,4,5,5-tetramethyl-1,3,2-dioxaborolan-2-yl)thiophene-3-carboxylate

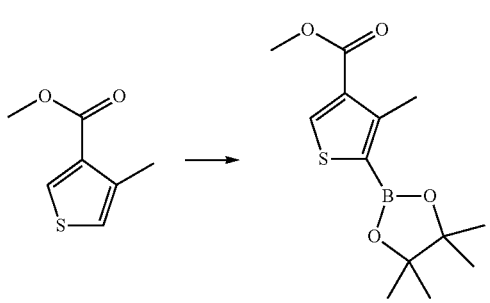

To a cooled (ice bath) mixture of (1,5-cyclooctadiene)(methoxy)iridium(I) dimer (1.6 g, 2.41 mmol) and 4,4,5,5-tetramethyl-1,3,2-dioxaborolane (25 mL, 173 mmol) was added a solution of 4,4'-di-tert-butyl-2,2'-dipyridyl (1.3 g, 4.84 mmol) in n-hexane (75 mL). After stirring for 1 min, methyl 4-methylthiophene-3-carboxylate (25 g, 160 mmol) was added (gas evolution seen). The reaction was allowed to warm to r.t. and was stirred overnight. The reaction was concentrated and the residue was purified by silica gel chromatography (0-10% EtOAc/hexanes) to give methyl 4-methyl-5-(4,4,5,5-tetramethyl-1,3,2-dioxaborolan-2-yl)thiophene-3-carboxylate (29.2 g, 104 mmol, 65% yield) as a colorless oil which solidified to a waxy white solid under vacuum. MS(ES) [M+H]+ 200.9 (boronic acid), 283.1 (boronate).

b') tert-Butyl 4-(1-(((trifluoromethyl)sulfonyl)oxy)vinyl)piperidine-1-carboxylate

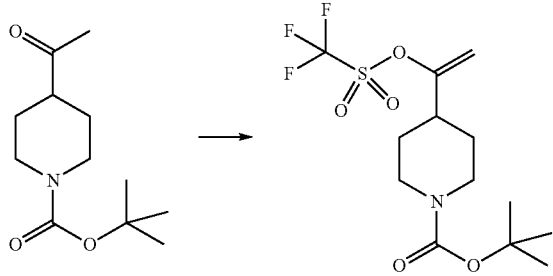 [SMILES: CC(=O)C1CCN(C(=O)OC(C)(C)C)CC1 ; C=C(OS(=O)(=O)C(F)(F)F)C1CCN(C(=O)OC(C)(C)C)CC1]

To a cooled (−78° C.) solution of tert-butyl 4-acetylpiperidine-1-carboxylate (25 g, 110 mmol) in THF (250 mL) under nitrogen was added dropwise 1 N sodium bis(trimethylsilyl)amide in THF (130 mL, 130 mmol). The reaction was maintained at −78° C. for 1 h, at which time a solution of 1,1,1-trifluoro-N-(pyridin-2-yl)-N-((trifluoromethyl)sulfonyl)methanesulfonamide (45 g, 126 mmol) in THF (100 mL) was added dropwise over 15 min. The reaction was maintained for 1 h at −78° C., then at 0° C. for 30 min. The reaction was quenched with cold water (500 mL), extracted with EtOAc (2×250 mL), washed with brine, dried (Na2SO4), and concentrated. The residue was purified by silica gel chromatography (0-20% EtOAc/hexanes) to give tert-butyl 4-(1-(((trifluoromethyl)sulfonyl)oxy)vinyl)piperidine-1-carboxylate (28.8 g, 80 mmol, 73% yield) as a colorless oil. MS(ES) [M+H]+-isobutylene 304.0, [M+H]+-Boc 260.0.

c') tert-Butyl 4-(1-(4-(methoxycarbonyl)-3-methylthiophen-2-yl)vinyl)piperidine-1-carboxylate

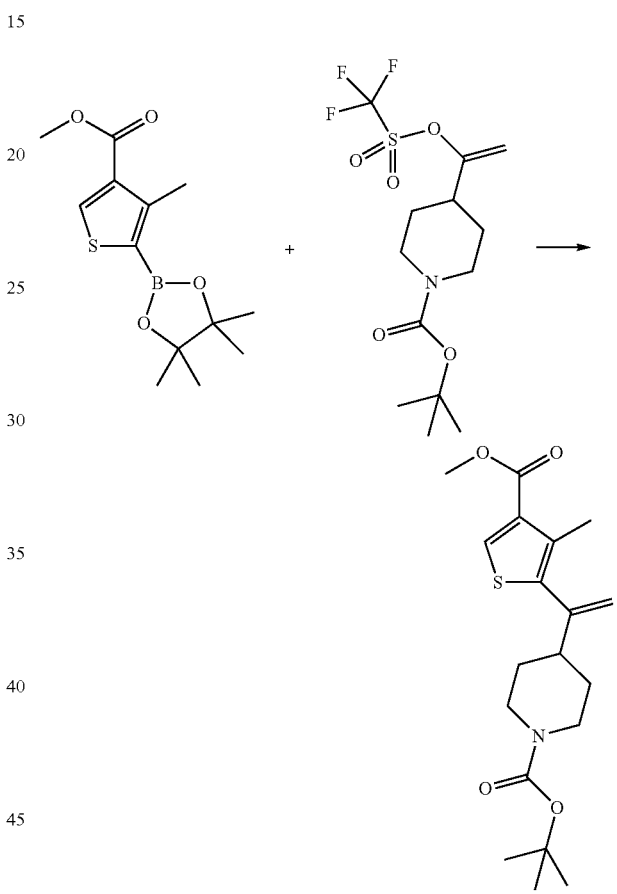

A mixture of methyl 4-methyl-5-(4,4,5,5-tetramethyl-1,3,2-dioxaborolan-2-yl)thiophene-3-carboxylate (33 g, 117 mmol), tert-butyl 4-(1-(((trifluoromethyl)sulfonyl)oxy)vinyl)piperidine-1-carboxylate (50 g, 139 mmol) and NaHCO3 (30 g, 357 mmol) in 1,4-dioxane (300 mL) and water (100 mL) was purged with nitrogen. The reaction was charged with tetrakis(triphenylphosphine)palladium(0) (6.8 g, 5.88 mmol) and heated at 70° C. under N2 for 2 h. The reaction was diluted with EtOAc (300 mL), washed with water (300 mL) and brine, dried (Na2SO4), and concentrated. The residue was purified by silica gel chromatography (0-20% EtOAc/hexanes) to give tert-butyl 4-(1-(4-(methoxycarbonyl)-3-methylthiophen-2-yl)vinyl)piperidine-1-carboxylate (34.5 g, 81% yield) as a light yellow oil. MS(ES) [M+H]+-Boc 266.1, [M+H]+-isobutylene-MeOH 278.0, [M+H]+-isobutylene 310.1, [M+Na]+ 388.1.

d') (R)-tert-Butyl 4-(1-(4-(methoxycarbonyl)-3-methylthiophen-2-yl)ethyl)piperidine-1-carboxylate

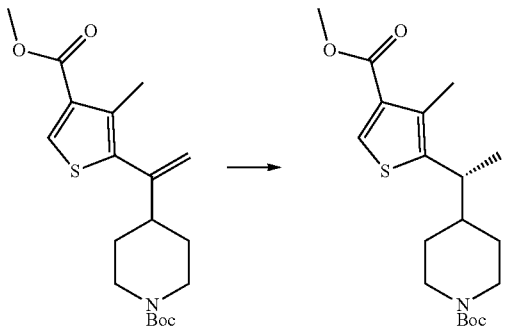 [SMILES: C=C(c1scc(C(=O)OC)c1C)C1CCN(C(=O)OC(C)(C)C)CC1 ; COC(=O)c1csc([C@H](C)C2CCN(C(=O)OC(C)(C)C)CC2)c1C]

A solution of tert-butyl 4-(1-(4-(methoxycarbonyl)-3-methylthiophen-2-yl)vinyl)piperidine-1-carboxylate (42.7 g, 117 mmol) and (R,R)-[COD]Ir[cy$_2$PThrePHOX](2.83 g, 1.636 mmol) in DCM (250 mL) was hydrogenated at 60 psi hydrogen pressure for 15 h on a Parr shaker. The mixture was concentrated and the residue purified by column chromatography (0-25% EtOAc/hexanes) to provide (R)-tert-butyl 4-(1-(4-(methoxycarbonyl)-3-methylthiophen-2-yl)ethyl)piperidine-1-carboxylate (38.3 g, 89% yield) as a faint yellow oil. Chiral HPLC (Chiralpak® AY-H, 5 microns (4.6 mm×150 mm); 240, 250 nm UV; 1.0 mL/min; 90:10:0.1 n-heptane:EtOH:isopropylamine (isocratic)) showed the material to be 98.5% ee. MS(ES) [M+H]$^+$ 368.3.

e') (R)-tert-Butyl 4-(1-(5-bromo-4-(methoxycarbonyl)-3-methylthiophen-2-yl)ethyl)piperidine-1-carboxylate

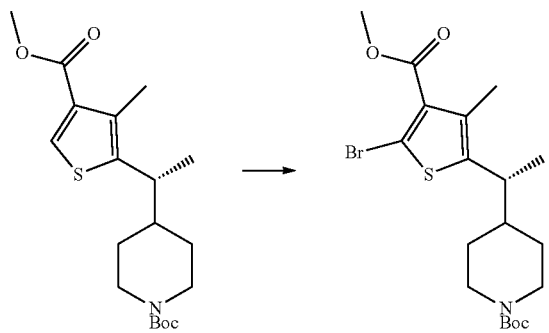 [SMILES: COC(=O)c1csc([C@H](C)C2CCN(C(=O)OC(C)(C)C)CC2)c1C ; COC(=O)c1c(Br)sc([C@H](C)C2CCN(C(=O)OC(C)(C)C)CC2)c1C]

To a cooled (0° C.) solution of (R)-tert-butyl 4-(1-(4-(methoxycarbonyl)-3-methylthiophen-2-yl)ethyl)piperidine-1-carboxylate (72.5 g, 200 mmol) in DMF (200 mL) was added NBS (49.1 g, 276 mmol). The ice bath was removed and the mixture was stirred at r.t. for 6 h. The mixture was poured into water and extracted with Et$_2$O (3×400 mL). The combined organics were concentrated to half volume, washed with aqueous sodium dithionite solution, and concentrated to dryness. Purification of the residue by column chromatography (0-30% EtOAc/hexanes) gave (R)-tert-butyl 4-(1-(5-bromo-4-(methoxycarbonyl)-3-methylthiophen-2-yl)ethyl)piperidine-1-carboxylate (79.8 g, 91% yield) as a light yellow oil. $^1$H NMR (400 MHz, CDCl$_3$) δ 4.24-3.99 (m, 2H), 3.92-3.85 (m, 3H), 2.89 (dd, J=7.1, 8.4 Hz, 1H), 2.72-2.51 (m, 2H), 2.23 (s, 3H), 1.90-1.79 (m, 1H), 1.54-1.48 (m, 1H), 1.45 (s, 9H), 1.31-1.27 (m, 1H), 1.26-1.22 (m, 3H), 1.20-1.02 (m, 2H). MS(ES) [M+H]$^+$ 468.2, 470.2 (M+Na).

f') (R)-tert-Butyl 4-(1-(4-(methoxycarbonyl)-3-methyl-5-(3-oxopropyl)thiophen-2-yl)ethyl)piperidine-1-carboxylate

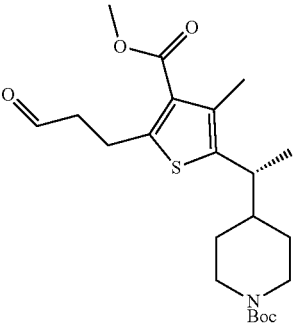

To a solution of (R)-tert-butyl 4-(1-(5-bromo-4-(methoxycarbonyl)-3-methylthiophen-2-yl)ethyl)piperidine-1-carboxylate (44 g) in MeOH (450 mL) was added Darco® activated carbon (40 g). The mixture was heated at 45° C. for 90 min, at which time it was filtered through Celite® and washed with warm MeOH (500 mL). The filtrate was concentrated and the residue was dissolved in EtOAc and heptane. The solution was concentrated and dried under vacuum (hivac) for 1 h to give 38 g of the starting material back.

To a solution of (R)-tert-butyl 4-(1-(5-bromo-4-(methoxycarbonyl)-3-methylthiophen-2-yl)ethyl)piperidine-1-carboxylate (38 g, 85 mmol) in DMF (400 mL) were added prop-2-en-1-ol (20.3 mL, 300 mmol), Bu$_4$NCl (23.7 g, 85 mmol) and Na$_2$CO$_3$ (22.6 g, 213 mmol). The reaction mixture was degassed with N$_2$ for 10-15 min and Pd(OAc)$_2$ (2.9 g, 12.8 mmol) was added. The reaction vessel was evacuated and refilled with N$_2$ (3×) and heated at 65° C. for 40 min. The reaction was allowed to cool to r.t., poured into sat. NH$_4$Cl (1200 mL), and extracted with Et$_2$O (2×). The combined extracts were dried (MgSO$_4$), filtered through Celite®, and concentrated. The residue was purified by column chromatography (3-25% EtOAc/heptanes) to give (R)-tert-butyl 4-(1-(4-(methoxycarbonyl)-3-methyl-5-(3-oxopropyl)thiophen-2-yl)ethyl)piperidine-1-carboxylate (26.2 g, 65% yield). MS(ES) [M+H]$^+$ 446.4 (M+Na).

g') (R)-tert-Butyl 4-(1-(5-(3-(((2-methoxy-4,6-dimethylpyridin-3-yl)methyl)amino)propyl)-4-(methoxycarbonyl)-3-methylthiophen-2-yl)ethyl)piperidine-1-carboxylate

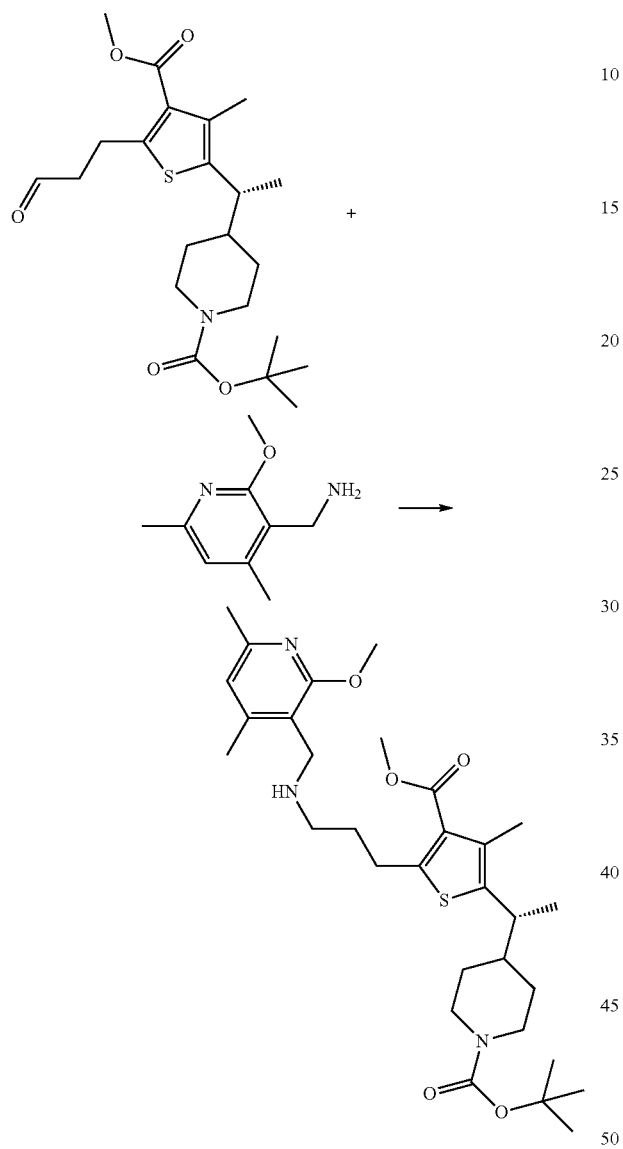

To a solution of (R)-tert-butyl 4-(1-(4-(methoxycarbonyl)-3-methyl-5-(3-oxopropyl)thiophen-2-yl)ethyl)piperidine-1-carboxylate (20 g, 47 mmol) in MeOH (300 mL) was added (2-methoxy-4,6-dimethylpyridin-3-yl)methanamine (9.4 g, 57 mmol) as a frozen solid. The reaction was maintained at r.t. for 1.5 h. The reaction was then cooled in an ice bath for 10 min, at which time NaBH$_4$ (4.5 g, 120 mmol) was added as a solid (vigorous foaming/gas evolution). The mixture was stirred for 15 min. The ice bath was removed and the reaction was stirred at r.t. for 1 h. The reaction was re-cooled in an ice bath and quenched with sat. aqueous NH$_4$Cl (120 mL). The ice bath was removed and the reaction was concentrated to ~¼ volume. The mixture was diluted with sat. aqueous NH$_4$Cl and extracted with EtOAc (2×). The combined organics were washed with brine, dried over MgSO$_4$ (stirred for 15 min), filtered through Celite®, and concentrated to give (R)-tert-butyl 4-(1-(5-(3-(((2-methoxy-4,6-dimethylpyridin-3-yl)methyl)amino)propyl)-4-(methoxycarbonyl)-3-methylthiophen-2-yl)ethyl)piperidine-1-carboxylate (27 g, 99% yield) as a white foam. MS(ES) [M+H]$^+$ 574.5.

h') (R)-5-(1-(1-(tert-Butoxycarbonyl)piperidin-4-yl)ethyl)-2-(3-(((2-methoxy-4,6-dimethylpyridin-3-yl)methyl)amino)propyl)-4-methylthiophene-3-carboxylic acid

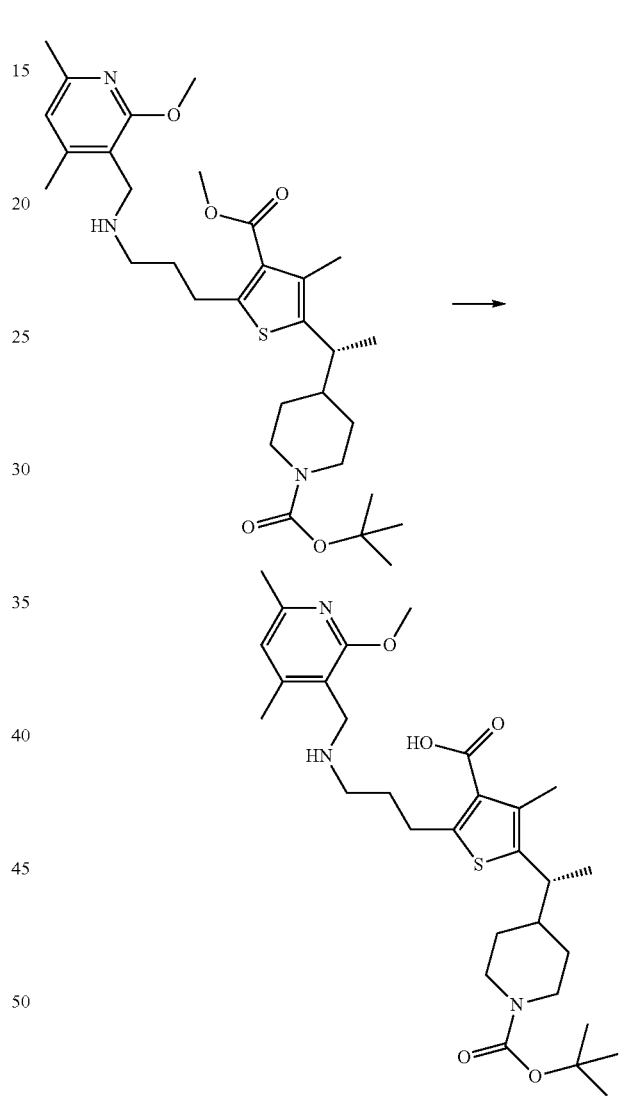

To a solution of (R)-tert-butyl 4-(1-(5-(3-(((2-methoxy-4,6-dimethylpyridin-3-yl)methyl)amino)propyl)-4-(methoxycarbonyl)-3-methylthiophen-2-yl)ethyl)piperidine-1-carboxylate (27 g, 47 mmol) in MeOH (400 mL) and THF (80 mL) was added 5 N NaOH (93 mL, 470 mmol). The reaction was heated at 63° C. for 18 h, at which time it was concentrated. The residue was diluted with water (150 mL) and DCM (300 mL) and cooled in an ice bath. To the mixture was added 6 N HCl (77 mL, 460 mmol) to adjust the pH to 5-6. The mixture was stirred well and the layers were separated. The aqueous layer was extracted with DCM (200 mL) and the combined organics were dried over MgSO$_4$ (stirred for 30 min), filtered through Celite® and concentrated to give (R)-5-(1-(1-(tert-butoxycarbonyl)piperidin-4-yl)ethyl)-2-(3-(((2-methoxy-4,6-dimethylpyridin-3-yl)methyl)amino)propyl)-4-methylthiophene-3-carboxylic acid (25 g, 80% yield). MS(ES) [M+H]+ 560.4.

i') (R)-tert-Butyl 4-(1-(5-((2-methoxy-4,6-dimethyl-pyridin-3-yl)methyl)-3-methyl-4-oxo-5,6,7,8-tetrahydro-4H-thieno[3,2-c]azepin-2-yl)ethyl)piperidine-1-carboxylate

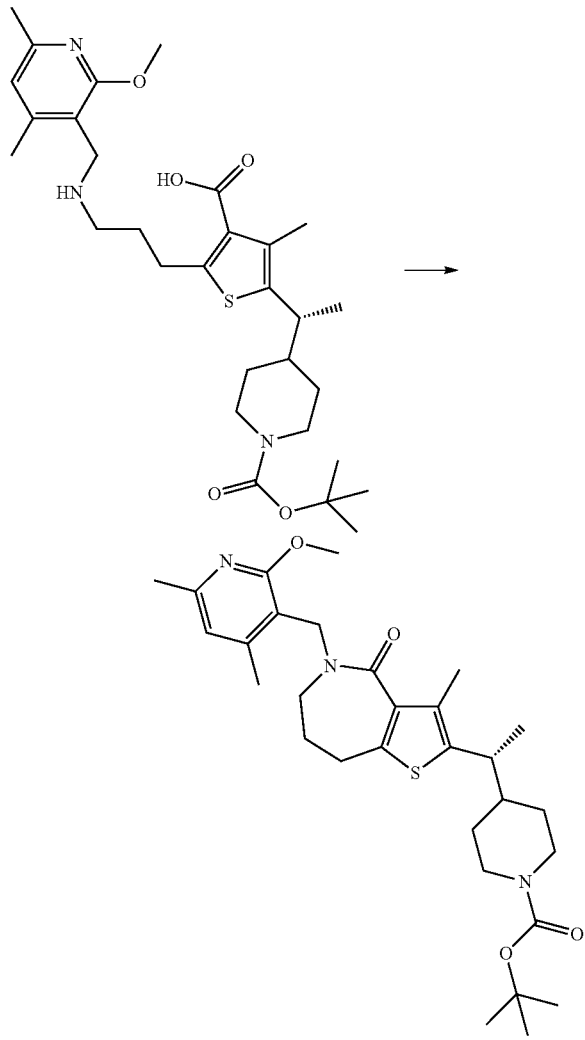

To a solution of (R)-5-(1-(1-(tert-butoxycarbonyl)piperidin-4-yl)ethyl)-2-(3-(((2-methoxy-4,6-dimethylpyridin-3-yl)methyl)amino)propyl)-4-methylthiophene-3-carboxylic acid (25.2 g, 45 mmol), EDC (10.4 g, 54 mmol) and HOAt (6.74 g, 49.5 mmol) in DMSO (200 mL) was added NMM (12.4 mL, 113 mmol). The reaction was maintained for 18 h, at which time it was poured slowly into ice water (1000 mL). The mixture was vigorously stirred (overhead stirrer) for 30 min. The mixture was filtered and the solids were washed with water and air-dried for 20 min. The still wet solid was dissolved in DCM and washed with sat. aqueous NH4Cl, dried (MgSO4), filtered through Celite®, and concentrated. Purification of the residue by column chromatography (8-40% 3:1 EtOAc/EtOH in heptane) gave (R)-tert-butyl 4-(1-(5-((2-methoxy-4,6-dimethylpyridin-3-yl)methyl)-3-methyl-4-oxo-5,6,7,8-tetrahydro-4H-thieno[3,2-c]azepin-2-yl)ethyl)piperidine-1-carboxylate (18.2 g, 72% yield). MS(ES) [M+H]+ 542.3.

j') (R)-5-((4,6-Dimethyl-2-oxo-1,2-dihydropyridin-3-yl)methyl)-3-methyl-2-(1-(piperidin-4-yl)ethyl)-5,6,7,8-tetrahydro-4H-thieno[3,2-c]azepin-4-one

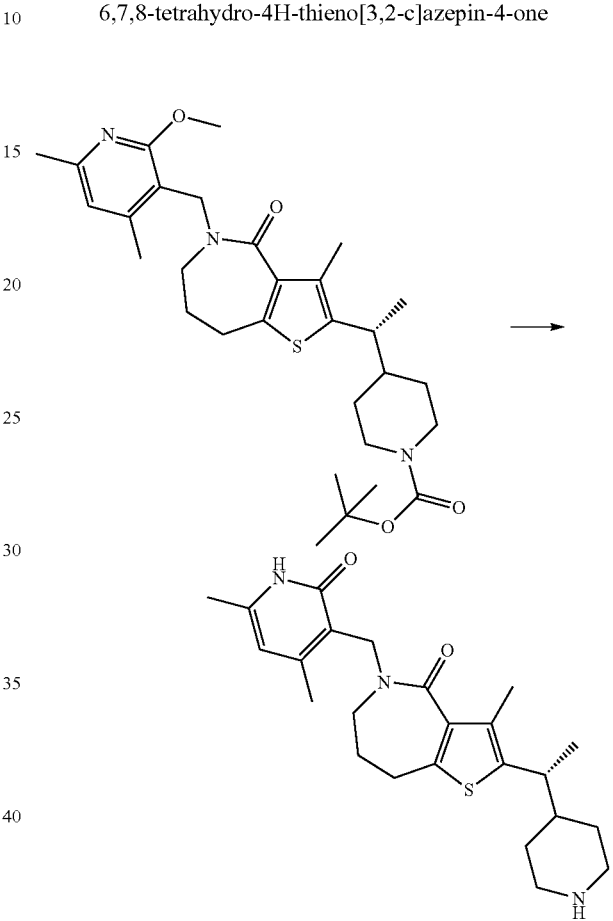

To a solution of (R)-tert-butyl 4-(1-(5-((2-methoxy-4,6-dimethylpyridin-3-yl)methyl)-3-methyl-4-oxo-5,6,7,8-tetrahydro-4H-thieno[3,2-c]azepin-2-yl)ethyl)piperidine-1-carboxylate (18.2 g, 33.6 mmol) in MeOH (200 mL) was added 4 N HCl in 1,4-dioxane (126 mL, 504 mmol). The reaction was maintained for 15 min at r.t., then heated at 70° C. for 30 h. The reaction was allowed to cool to r.t. and concentrated. The residue was diluted with DCM (300 mL) and water (150 mL) and the pH was adjusted to ~11 with concentrated NH4OH. The mixture was stirred for 15 min, at which time the layers were separated. The aqueous layer was extracted with DCM (2x) and the combined organics were dried (MgSO4), filtered, and concentrated. The residue was dissolved in TBME (200 mL) and swirled in a 45° C. water bath for 30 min. A white solid formed. The mixture was concentrated and further dried under vacuum (hivac) for 4 h to give (R)-5-((4,6-dimethyl-2-oxo-1,2-dihydropyridin-3-yl)methyl)-3-methyl-2-(1-(piperidin-4-yl)ethyl)-5,6,7,8-tetrahydro-4H-thieno[3,2-c]azepin-4-one (15.6 g, 106% yield) as a off-white solid that was used without further purification. MS(ES) [M+H]+ 428.3.

k') (R)-5-((4,6-Dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one

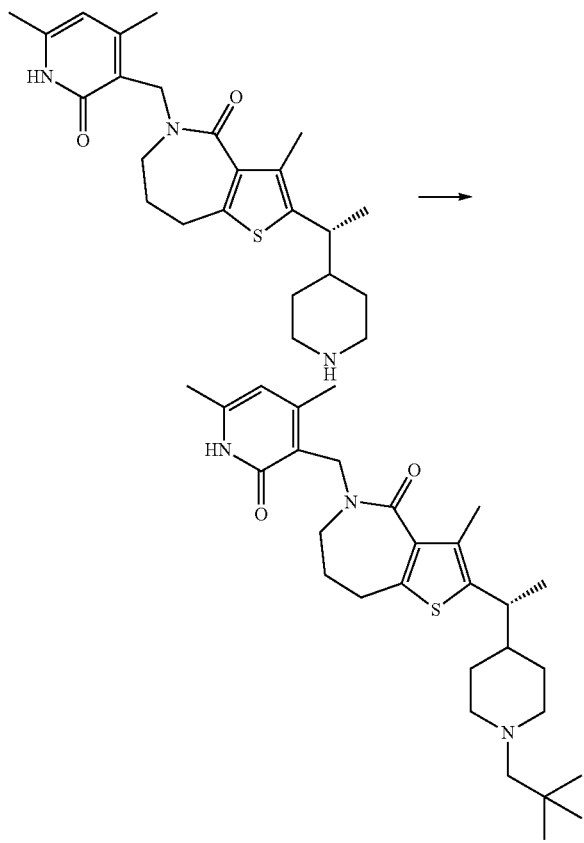

To a solution of (R)-5-((4,6-dimethyl-2-oxo-1,2-dihydropyridin-3-yl)methyl)-3-methyl-2-(1-(piperidin-4-yl)ethyl)-5,6,7,8-tetrahydro-4H-thieno[3,2-c]azepin-4-one (28 g, 66 mmol) in DCE (400 mL) was added pivalaldehyde (15 mL, 140 mmol). The reaction was stirred for 3 min, at which time AcOH (7.9 mL, 140 mmol) was added. After 10 min, NaBH(OAc)$_3$ (41.6 g, 196 mmol) was added as a solid and the reaction was stirred at r.t. for 40 h. The reaction was poured into ice and DCM and stirred well. The pH was adjusted to ~10 with a combination of sat. NaHCO$_3$ and sat. Na$_2$CO$_3$. The mixture was stirred for 15 min and the layers were separated. The aqueous layer was extracted with DCM and the combined organics were dried over MgSO$_4$, filtered through Celite® and concentrated. The residue was purified by column chromatography (10-80% 3:1 EtOAc/EtOH+1% NH$_4$OH in heptane). The purified residue was dried under vacuum (hivac) for 18 h to give (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one (24.5 g, 74% yield). $^1$H NMR (400 MHz, DMSO-d$_6$) δ 0.81 (s, 9H) 1.07-1.29 (m, 6H) 1.33 (d, J=9.63 Hz, 1H) 1.65 (quin, J=6.72 Hz, 2H) 1.74 (d, J=10.14 Hz, 1H) 1.92-2.05 (m, 3H) 2.06-2.20 (m, 10H) 2.62-2.73 (m, 3H) 2.74-2.91 (m, 2H) 3.16-3.29 (m, 2H) 4.50 (d, J=13.43 Hz, 1H) 4.61 (d, J=13.69 Hz, 1H) 5.90 (s, 1H) 11.57 (s, 1H). MS(ES) [M+H]$^+$ 498.4.

Preparation of the Crystalline Hydrochloric Acid Salt of the Compound of Example 1

(R)-5-((4,6-Dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one (20 mg) was combined with acetone (0.2 mL). The mixture was heated to 40° C. with stirring. To the solution was added aqueous HCl (3.0 M, 13 μL). The slurry was temperature-cycled in 1 h blocks between 40° C. and 5° C. overnight. The resulting slurries were stirred at room temperature, checked by PLM for birefringence and isolated by filtration to give the crystalline HCl salt (Form I), which would be used to seed a larger scale preparation.

The experiment was repeated using 50 mg of (R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one and seeding with the Form I crystals from above. However, the experiment produced a new crystalline form of HCl salt, designated Form II. Form II of the HCl salt appeared to be a more stable form, due to the form conversion of Form I seeds to Form II, and the higher endotherm observed by DSC.

(R)-5-((4,6-Dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one (462 mg; 0.928 mmol) was combined with acetone (9.0 mL; 20 vol) at 40° C. with stirring. Aqueous HCl (3.0 M; 309 μL) was added to the solution, followed by seed crystals (Form II). The mixture showed precipitation within a few minutes. The slurry was heated at 40° C. for 1 h, then slowly cooled to 5° C. with cooling rate of 0.1° C./min. The heat-cool cycle was then repeated 3 times over a 24 h period. The slurry was equilibrated at RT for 1 h. The solids were filtered, and the wet cake was analyzed by XRPD. The remaining solids were dried at 40° C. under vacuum with a nitrogen bleed for 4 hours. The yield was 89.3% (443 mg; 0.829 mmol) of crystalline HCl salt.

The crystalline HCl salt was analyzed by XRPD and was consistent with Form II as the wet cake before and after drying. Thermal data showed a weight loss of 0.8% up to 200° C., and a large endotherm at 294° C. associated with decomposition. The PLM image showed small, irregularly shaped particles. The material was a stoichiometric 1:1 salt, as determined by analysis by ion-chromatography. DVS data showed 0.5% total moisture uptake during the first cycle from 40-75% RH. The second cycle, from 5-80% RH, showed a fairly linear sorption of 1.0% followed by a 0.4% decrease between 80-90% RH. XRPD data on the HCl salt after the DVS experiment did not indicate a form change or change in crystallinity.

The X-ray powder diffraction (XRPD) pattern of this material (Form II) is shown in FIG. 1 and a summary of the diffraction angles and d-spacings is given in Table I below. The XRPD analysis was conducted on a PANanalytical X'Pert Pro Diffractometer on Si zero-background wafers using X'celerator™ RTMS (Real Time Multi-Strip) detector. The acquisition conditions included: Cu K$_\alpha$ radiation, generator tension: 45 kV, generator current: 40 mA, step size: 0.02° 2θ. Configuration on the incidental beam side: fixed divergence slit (0.250), 0.04 rad Soller slits, anti-scatter slit (0.250), and 10 mm beam mask. Configuration on the diffracted beam side: fixed divergence slit (0.250) and 0.04 rad Soller slit.

TABLE I

| Diff. Angle [°2θ] | d-spacing [Å] |
|---|---|
| 4.5079 | 19.6026 |
| 7.6605 | 11.5408 |
| 8.9461 | 9.8850 |
| 9.5064 | 9.3037 |
| 10.7274 | 8.2473 |
| 12.7387 | 6.9493 |
| 13.4333 | 6.5915 |
| 14.2730 | 6.2055 |
| 14.7733 | 5.9965 |
| 14.9151 | 5.9398 |
| 15.3236 | 5.7824 |
| 15.7135 | 5.6398 |
| 16.2921 | 5.4407 |
| 16.8882 | 5.2500 |
| 17.4396 | 5.0853 |
| 18.2570 | 4.8594 |
| 18.5517 | 4.7829 |
| 19.0696 | 4.6541 |
| 21.8905 | 4.0603 |
| 22.4380 | 3.9625 |
| 23.1074 | 3.8492 |
| 24.0160 | 3.7056 |
| 24.3592 | 3.6541 |
| 24.9714 | 3.5659 |
| 25.5654 | 3.4844 |
| 26.8997 | 3.3145 |
| 27.7205 | 3.2182 |
| 28.7881 | 3.1013 |
| 29.3745 | 3.0407 |
| 30.3557 | 2.9446 |
| 31.1714 | 2.8694 |
| 33.4428 | 2.6795 |
| 35.2618 | 2.5453 |
| 37.5253 | 2.3968 |
| 38.8381 | 2.3188 |

The Raman spectrum of this material (Form II) was recorded on a Nicolet NXR 9650 FT-Raman Spectrometer, at 4 cm$^{-1}$ resolution with excitation from a Nd:YVO4 laser ($\lambda$=1064 nm). The Raman spectrum of this material is shown in FIG. 2 with major peaks observed at 455.0, 478.7, 505.2, 533.5, 541.7, 565.1, 612.1, 693.5, 757.9, 791.3, 853.9, 995.1, 1046.7, 1113.8, 1148.2, 1208.9, 1240.9, 1279.4, 1315.4, 1390.2, 1437.7, 1473.5, 1550.7, 1628.2, 1654.8, 2735.5, 2917.4, and 2953.0 cm$^{-1}$.

The differential scanning calorimetry (DSC) thermogram of this material (Form II) was recorded on a TA Instruments Q100 Differential Scanning Calorimeter equipped with an autosampler and a refrigerated cooling system under 40 mL/min N$_2$ purge and is shown in FIG. 3. The experiments were conducted using a heating rate of 15° C./min in a crimped aluminum pan. The DSC thermogram of this material (Form II) exhibited a large single endotherm with an onset temperature of about 250° C., a peak temperature about 298° C., and enthalpy of 195.4 J/g. A person skilled in the art would recognize that the onset temperature, peak temperature, and enthalpy of the endotherm may vary depending on the experimental conditions.

The thermogravimetric analysis (TGA) thermogram of this material (Form II) was recorded on a TA Instruments Q500 Thermogravimetric Analyzer and is shown in FIG. 4. The experiments were conducted with 40 mL/min N$_2$ flow and a heating rate of 15° C./min. The TGA thermogram of this material (Form II) exhibited a single weight loss event observed prior to the final thermal decomposition. The weight loss event takes place in the temperature range of 30° C. to 200° C. with a weight loss of about 0.8%.

Example 2

(R)-2-(1-(1-(Cyclobutylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one

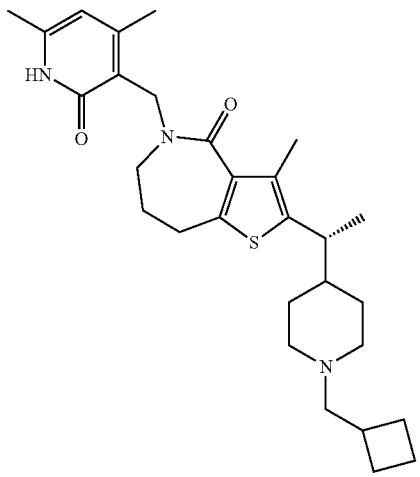 [SMILES: Cc1cc(C)c(CN2CCCc3sc([C@H](C)C4CCN(CC5CCC5)CC4)c(C)c3C2=O)c(=O)[nH]1]

Following the general procedure of Example 1, (R)-2-(1-(1-(cyclobutylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one was prepared. $^1$H NMR (DMSO-d$_6$) δ 11.58 (s, 1H), 5.90 (s, 1H), 4.60 (d, J=13.7 Hz, 1H), 4.50 (d, J=13.7 Hz, 1H), 3.15-3.30 (m, 2H), 2.76-2.90 (m, 2H), 2.62-2.75 (m, 3H), 2.34-2.45 (m, 1H), 2.04-2.31 (m, 11H), 1.90-2.02 (m, 2H), 1.55-1.83 (m, 8H), 1.36 (d, J=12.2 Hz, 1H), 1.05-1.31 (m, 7H). MS(ES) [M+H]$^+$ 496.4.

Example 3

(R)-5-((4,6-Dimethyl-2-oxo-1,2-dihydropyridin-3-yl)methyl)-2-(1-(1-isobutylpiperidin-4-yl)ethyl)-3-methyl-5,6,7,8-tetrahydro-4H-thieno[3,2-c]azepin-4-one

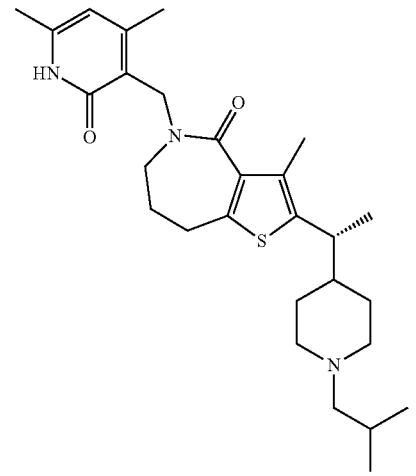 [SMILES: Cc1cc(C)c(CN2CCCc3sc([C@H](C)C4CCN(CC(C)C)CC4)c(C)c3C2=O)c(=O)[nH]1]

Following the general procedure of Example 1, (R)-5-((4,6-dimethyl-2-oxo-1,2-dihydropyridin-3-yl)methyl)-2-(1-(1-isobutylpiperidin-4-yl)ethyl)-3-methyl-5,6,7,8-tetrahydro-4H-thieno[3,2-c]azepin-4-one was prepared. $^1$H NMR (DMSO-d$_6$) δ 11.58 (s, 1H), 5.91 (s, 1H), 4.60 (d, J=13.4 Hz, 1H), 4.50 (d, J=13.4 Hz, 1H), 3.16-3.29 (m, 2H), 2.79-2.93

(m, 2H), 2.74 (d, J=11.2 Hz, 1H), 2.66 (t, J=7.2 Hz, 2H), 2.09-2.20 (m, 9H), 1.95 (d, J=7.4 Hz, 2H), 1.59-1.83 (m, 6H), 1.38 (d, J=11.9 Hz, 1H), 1.07-1.29 (m, 6H), 0.81 (d, J=6.3 Hz, 6H). MS(ES) [M+H]+ 484.4.

Example 4

(R)-2-(1-(1-(Cyclopentylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one

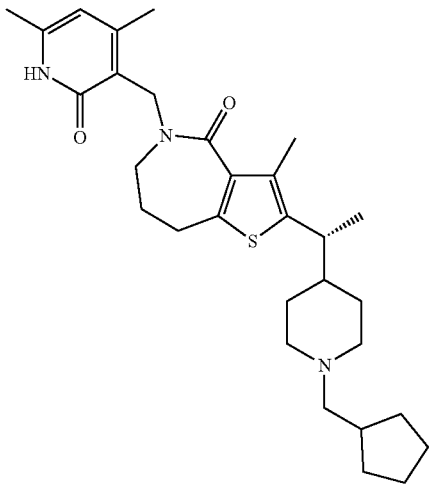 [SMILES: Cc1cc(C)c(CN2CCCc3sc([C@H](C)C4CCN(CC5CCCC5)CC4)c(C)c3C2=O)c(=O)[nH]1]

Following the general procedure of Example 1, (R)-2-(1-(1-(cyclopentylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one was prepared. $^1$H NMR (DMSO-d$_6$) δ 11.51-11.64 (m, 1H), 5.91 (s, 1H), 4.56-4.68 (m, 1H), 4.45-4.54 (m, 1H), 3.24 (t, J=5.45 Hz, 2H), 2.74-2.93 (m, J=8.36 Hz, 3H), 2.67 (t, J=7.22 Hz, 2H), 2.12-2.20 (m, 9H), 1.96-2.11 (m, 3H), 1.66 (d, J=6.84 Hz, 8H), 1.33-1.57 (m, 5H), 1.12-1.22 (m, 7H). MS(ES) [M+H]+ 510.5.

Example 5

(R)-5-((4,6-Dimethyl-2-oxo-1,2-dihydropyridin-3-yl)methyl)-2-(1-(1-(2,2-dimethylbutyl)piperidin-4-yl)ethyl)-3-methyl-5,6,7,8-tetrahydro-4H-thieno[3,2-c]azepin-4-one

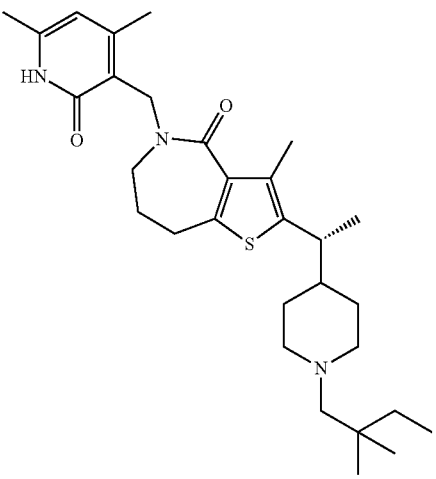 [SMILES: CCC(C)(C)CN1CCC([C@@H](C)c2sc3c(c2C)C(=O)N(Cc2c(C)cc(C)[nH]c2=O)CCC3)CC1]

Following the general procedure of Example 1, (R)-5-((4,6-dimethyl-2-oxo-1,2-dihydropyridin-3-yl)methyl)-2-(1-(1-(2,2-dimethylbutyl)piperidin-4-yl)ethyl)-3-methyl-5,6,7,8-tetrahydro-4H-thieno[3,2-c]azepin-4-one was prepared. $^1$H NMR (DMSO-d$_6$) δ 11.58 (br. s., 1H), 5.91 (s, 1H), 4.56-4.66 (m, 1H), 4.46-4.54 (m, 1H), 3.23 (d, J=13.18 Hz, 1H), 2.74-2.87 (m, J=11.41 Hz, 2H), 2.65-2.70 (m, 3H), 2.16 (s, 3H), 2.13 (d, J=1.52 Hz, 7H), 1.99 (s, 3H), 1.74 (d, J=8.87 Hz, 1H), 1.60-1.69 (m, J=6.84 Hz, 2H), 1.33 (d, J=7.86 Hz, 1H), 1.10-1.26 (m, 9H), 0.73-0.79 (m, 9H). MS(ES) [M+H]+ 512.4.

Example 6

(R)-5-((4,6-Dimethyl-2-oxo-1,2-dihydropyridin-3-yl)methyl)-2-(1-(1-(2-fluoro-2-methylpropyl)piperidin-4-yl)ethyl)-3-methyl-5,6,7,8-tetrahydro-4H-thieno[3,2-c]azepin-4-one

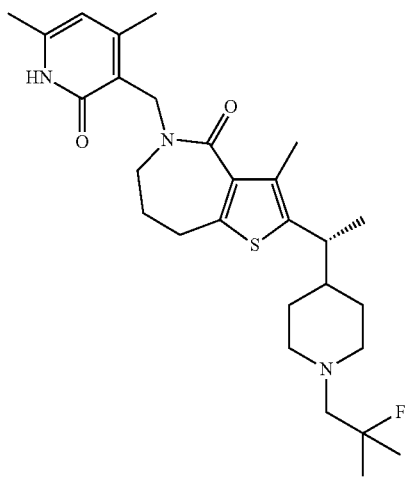 [SMILES: Cc1cc(C)c(CN2CCCc3sc([C@H](C)C4CCN(CC(C)(C)F)CC4)c(C)c3C2=O)c(=O)[nH]1]

a) (R)-5-((2-Methoxy-4,6-dimethylpyridin-3-yl)methyl)-3-methyl-2-(1-(piperidin-4-yl)ethyl)-5,6,7,8-tetrahydro-4H-thieno[3,2-c]azepin-4-one

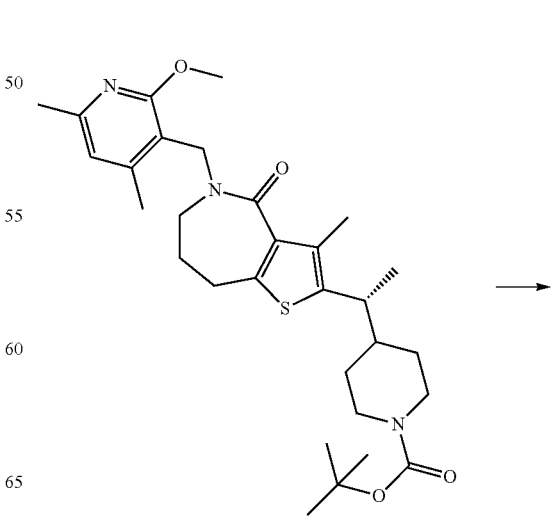

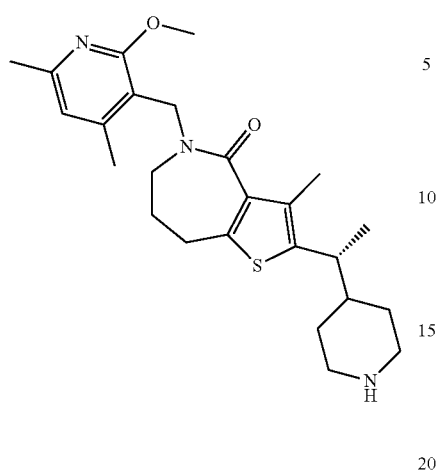

(R)-tert-Butyl 4-(1-(5-((2-methoxy-4,6-dimethylpyridin-3-yl)methyl)-3-methyl-4-oxo-5,6,7,8-tetrahydro-4H-thieno[3,2-c]azepin-2-yl)ethyl)piperidine-1-carboxylate (3.0 g, 5.54 mmol) was treated with a solution of TFA (5.12 mL, 66.5 mmol) in DCM (17 mL). The reaction was maintained for 3.5 h. LCMS showed ~8% starting material remained. To the reaction was slowly added dropwise more TFA (0.7 mL). After 30 min, LCMS showed the reaction was complete. The reaction was slowly poured into a mixture of ice, water, and sat. NaHCO$_3$ with stirring. The mixture was diluted with DCM and was stirred for 15 min (measured pH 8). The layers were separated and the aqueous extracted with DCM. The organics were combined, dried (MgSO$_4$), and concentrated to give (R)-5-((2-methoxy-4,6-dimethylpyridin-3-yl)methyl)-3-methyl-2-(1-(piperidin-4-yl)ethyl)-5,6,7,8-tetrahydro-4H-thieno[3,2-c]azepin-4-one (2.7 g). MS(ES) [M+H]$^+$ 442.2.

b) (R)-2-(1-(1-(2-Fluoro-2-methylpropyl)piperidin-4-yl)ethyl)-5-((2-methoxy-4,6-dimethylpyridin-3-yl)methyl)-3-methyl-5,6,7,8-tetrahydro-4H-thieno[3,2-c]azepin-4-one

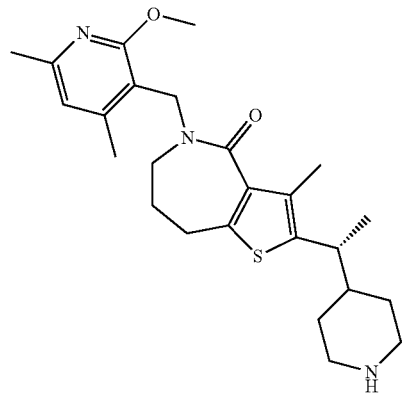

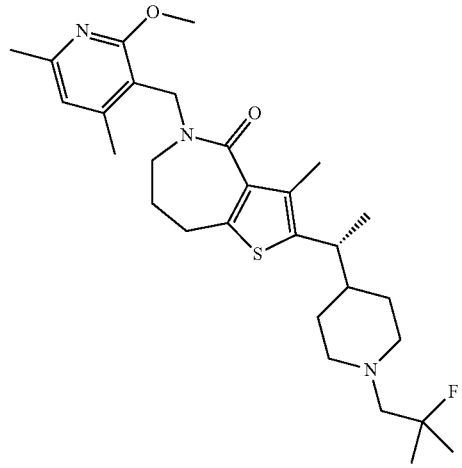

To a solution of (R)-5-((2-methoxy-4,6-dimethylpyridin-3-yl)methyl)-3-methyl-2-(1-(piperidin-4-yl)ethyl)-5,6,7,8-tetrahydro-4H-thieno[3,2-c]azepin-4-one (1.6 g, 3.62 mmol) in CH$_3$CN (20 mL) were added 2-fluoro-2-methylpropyl trifluoromethanesulfonate (1.624 g, 7.25 mmol) and Cs$_2$CO$_3$ (3.54 g, 10.87 mmol). The mixture was heated at 50° C. for 6 h, at which time it was diluted with DCM (30 mL) and filtered. The filtrate was concentrated and the residue was purified using column chromatography (0-60% EtOAc/hexanes) to give (R)-2-(1-(1-(2-fluoro-2-methylpropyl)piperidin-4-yl)ethyl)-5-((2-methoxy-4,6-dimethylpyridin-3-yl)methyl)-3-methyl-5,6,7,8-tetrahydro-4H-thieno[3,2-c]azepin-4-one (1.2 g) as a pale brown solid. MS(ES) [M+H]$^+$ 516.4.

c) (R)-5-((4,6-Dimethyl-2-oxo-1,2-dihydropyridin-3-yl)methyl)-2-(1-(1-(2-fluoro-2-methylpropyl)piperidin-4-yl)ethyl)-3-methyl-5,6,7,8-tetrahydro-4H-thieno[3,2-c]azepin-4-one

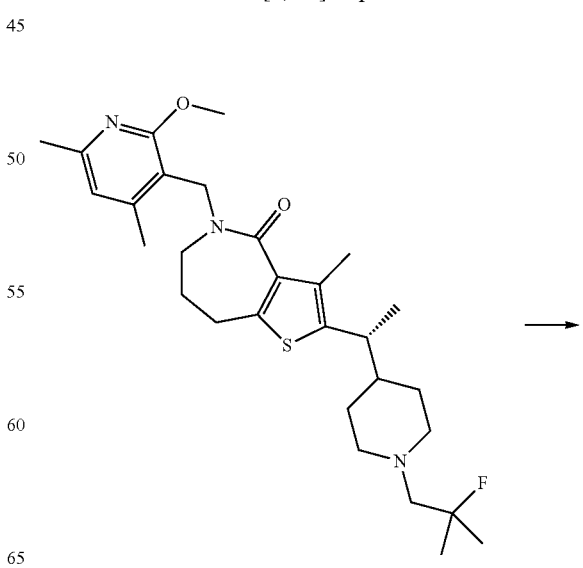

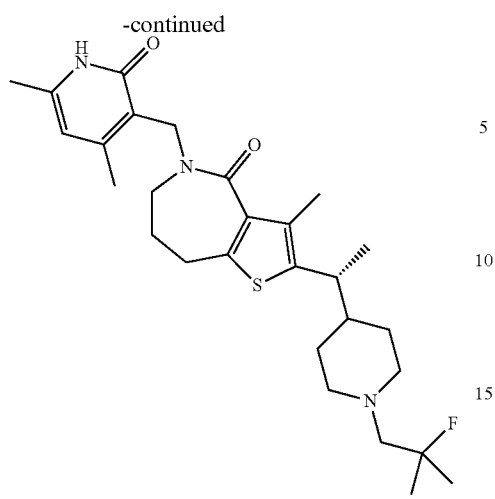

To a solution of (R)-2-(1-(1-(2-fluoro-2-methylpropyl) piperidin-4-yl)ethyl)-5-((2-methoxy-4,6-dimethylpyridin-3-yl)methyl)-3-methyl-5,6,7,8-tetrahydro-4H-thieno[3,2-c]azepin-4-one (1.20 g, 2.327 mmol) in 1,4-dioxane (12 mL) was added 6 N HCl (3.88 mL, 23.27 mmol). The mixture was stirred at 70° C. for 18 h. The mixture was concentrated and the residue was dissolved in MeOH (10 mL). NaHCO$_3$ (0.586 g, 6.98 mmol) was added and the mixture was stirred for 15 min and filtered. The filtrate was concentrated and the residue was purified using column chromatography (10-80% 3:1 EtOAc/MeOH+1% NH$_4$OH in heptane) to give (R)-5-((4,6-dimethyl-2-oxo-1,2-dihydropyridin-3-yl)methyl)-2-(1-(1-(2-fluoro-2-methylpropyl)piperidin-4-yl)ethyl)-3-methyl-5,6,7,8-tetrahydro-4H-thieno[3,2-c]azepin-4-one (960 mg, 81%) as a white solid. $^1$H NMR (400 MHz, methanol-d$_4$) δ 1.23-1.51 (m, 12H), 1.76-1.92 (m, 3H), 1.95-2.13 (m, 2H), 2.22 (s, 3H), 2.28 (s, 3H), 2.30-2.35 (m, 3H), 2.38-2.43 (m, 1H), 2.44-2.49 (m, 1H), 2.78 (t, J=7.35 Hz, 2H), 2.85-2.97 (m, 2H), 3.04 (d, J=11.41 Hz, 1H), 3.35-3.43 (m, 2H), 4.68-4.85 (m, 2H), 6.15 (s, 1H). MS(ES) [M+H]$^+$ 502.6.

Example 7

(R)-2-(1-(1-(Cyclopropylmethyl)piperidin-4-yl) ethyl)-5-((4,6-dimethyl-2-oxo-1,2-dihydropyridin-3-yl)methyl)-3-methyl-5,6,7,8-tetrahydro-4H-thieno[3,2-c]azepin-4-one

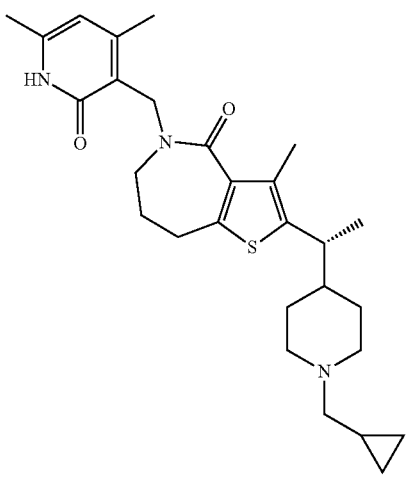 [SMILES: Cc1cc(C)c(CN2CCCc3sc([C@H](C)C4CCN(CC5CC5)CC4)c(C)c3C2=O)c(=O)[nH]1]

Following the general procedure of Example 1, (R)-2-(1-(1-(cyclopropylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one was prepared. $^1$H NMR (DMSO-d$_6$) δ 11.58 (s, 1H) 5.91 (s, 1H) 4.40-4.66 (m, 2H) 3.24 (t, J=6.21 Hz, 2H) 2.98 (d, J=11.15 Hz, 1H) 2.84-2.92 (m, 2H) 2.67 (t, J=7.22 Hz, 2H) 2.15 (d, J=10.65 Hz, 9H) 2.10 (d, J=6.59 Hz, 2H) 1.61-1.86 (m, 5H) 1.39 (d, J=11.91 Hz, 1H) 1.10-1.26 (m, 6H) 0.72-0.83 (m, 1H) 0.38-0.45 (m, 2H) −0.01-0.06 (m, 2H). MS(ES) [M+H]$^+$ 482.4.

Example 8

(R)-5-((4,6-Dimethyl-2-oxo-1,2-dihydropyridin-3-yl)methyl)-3-methyl-2-(1-(1-((1-methylcyclopentyl) methyl)piperidin-4-yl)ethyl)-5,6,7,8-tetrahydro-4H-thieno[3,2-c]azepin-4-one

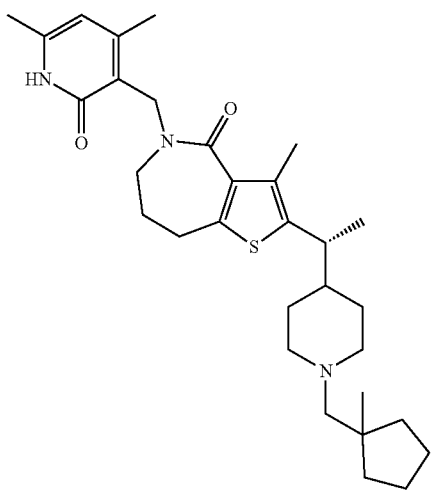 [SMILES: Cc1cc(C)c(CN2CCCc3sc([C@H](C)C4CCN(CC5(C)CCCC5)CC4)c(C)c3C2=O)c(=O)[nH]1]

Following the general procedure of Example 1, (R)-5-((4,6-dimethyl-2-oxo-1,2-dihydropyridin-3-yl)methyl)-3-methyl-2-(1-(1-((1-methylcyclopentyl)methyl)piperidin-4-yl)ethyl)-5,6,7,8-tetrahydro-4H-thieno[3,2-c]azepin-4-one was prepared. $^1$H NMR (400 MHz, methanol-d$_4$) δ 0.90 (m, 3H), 1.12-1.29 (m, 8H), 1.29-1.45 (m, 3H), 1.50-1.72 (m, 6H), 1.76 (d, J=7.86 Hz, 1H), 1.96-2.11 (m, 2H), 2.11-2.24 (m, 11H), 2.60-2.72 (m, 2H), 2.77 (d, J=11.66 Hz, 1H), 2.81-2.93 (m, 2H), 3.19-3.29 (m, 2H), 4.50 (d, J=13.69 Hz, 1H), 4.61 (d, J=13.69 Hz, 1H), 5.91 (s, 1H), 8.17 (s, 1H). MS(ES) [M+H]$^+$524.4.

Example 9

(R)-2-(1-(1-(Bicyclo[2.2.2]octan-1-ylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one

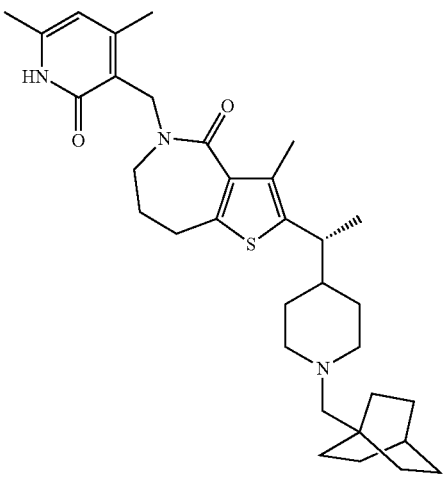 [SMILES: Cc1cc(C)c(CN2CCCc3sc([C@H](C)C4CCN(CC56CCC(CC5)CC6)CC4)c(C)c3C2=O)c(=O)[nH]1]

Following the general procedure of Example 1, (R)-2-(1-(1-(bicyclo[2.2.2]octan-1-ylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one was prepared. $^1$H NMR (400 MHz, methanol-$d_4$) δ 1.32 (d, J=6.84 Hz, 3H), 1.49-1.85 (m, 20H), 2.10 (b, 1H), 2.23 (s, 3H), 2.28 (s, 3H), 2.32 (s, 3H), 2.72-3.19 (m, 7H), 3.35-3.55 (m, 4H), 4.73 (d, J=13.94 Hz, 1H), 4.82 (d, J=13.94 Hz, 1H), 6.15 (s, 1H), 8.51 (s, 1H). MS(ES) [M+H]$^+$ 550.4.

Example 10

(R)-5-((4,6-Dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one

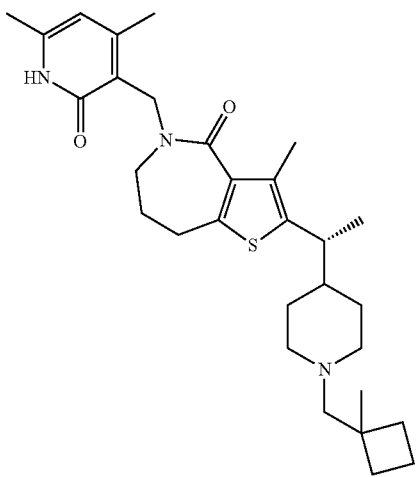 [SMILES: Cc1cc(C)c(CN2CCCc3sc([C@H](C)C4CCN(CC5(C)CCC5)CC4)c(C)c3C2=O)c(=O)[nH]1]

To a solution of (R)-5-((4,6-dimethyl-2-oxo-1,2-dihydropyridin-3-yl)methyl)-3-methyl-2-(1-(piperidin-4-yl)ethyl)-5,6,7,8-tetrahydro-4H-thieno[3,2-c]azepin-4-one (43 g, 91 mmol) in DCE (600 mL) was added 1-methylcyclobutane-1-carbaldehyde (15.43 g, 149 mmol). The reaction was stirred for 3 min, at which time AcOH (10.88 mL, 190 mmol) was added. After 8 min, NaBH(OAc)$_3$ (57.5 g, 272 mmol) was added as a solid and the reaction was stirred at r.t. for 18 h. LCMS showed reaction was 80% complete. To the reaction mixture was added more NaBH(OAc)$_3$ (5 g, 24 mmol). After 1 h, LCMS showed no change. To the mixture was added 1-methylcyclobutane-1-carbaldehyde (2 g, 20 mmol). The reaction was stirred for 2 h, at which time it was poured into ice and DCM. The pH was adjusted to 10 with a combination of sat. NaHCO$_3$ and sat. Na$_2$CO$_3$. The mixture was stirred for 15 min and the layers were separated. The aqueous layer was extracted with DCM and the combined organics were dried over MgSO$_4$, filtered through Celite® and concentrated. The residue was purified by column chromatography (330 g Isco® silica column; gradient B: 10-80%; A=heptane; B=3:1 EtOAc/EtOH+1% NH$_4$OH). The product-containing fractions were concentrated in vacuo until a white solid precipitated. Heptane was added and the solid was filtered. The filtrate was concentrated until a white precipitate formed. The solid was filtered and rinsed with heptane. The filtrate was concentrated a third time until a white precipitate formed, which was filtered and rinsed with heptane. The combined solids were dried in a vacuum oven at 40° C. for 18 h to give (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one (37.15 g, 71.4 mmol, 79% yield). $^1$H NMR (DMSO-$d_6$) δ 1.10 (s, 4H) 1.13-1.22 (m, 5H) 1.35 (d, J=12.17 Hz, 1H) 1.51-1.60 (m, 2H) 1.61-1.88 (m, 9H) 2.04-2.21 (m, 11H) 2.58-2.77 (m, 4H) 2.84 (quin, J=6.97 Hz, 1H) 3.14-3.29 (m, 2H) 4.51 (d, J=13.69 Hz, 1H) 4.60 (d, J=13.69 Hz, 1H) 5.90 (s, 1H) 11.59 (s, 1H). MS(ES) [M+H]$^+$ 510.3.

Preparation of the Crystalline Hydrochloric Acid Salt of the Compound of Example 10

(R)-5-((4,6-Dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one (20 mg) was combined with CH$_3$CN (0.2 mL). The mixture was heated to 40° C. with stirring. To the slurry was added aqueous HCl (3.0 M, 13 μL). The slurry was temperature-cycled between 40° C. and 5° C. for 3 days. The mixture was cooled to 4° C. and held at 4° C. for 3 days. The slurry was allowed to warm to RT and a portion of the solvent was allowed to slowly evaporate. The slurry was equilibrated at RT for 1 h, isolated by filtration, and analyzed by Raman to give the crystalline HCl salt (Form I), which would be used to seed a larger scale preparation.

CH$_3$CN (6.0 mL, 20 vol) was added to (R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one (303.3 mg, 0.595 mmol). One equivalent of aqueous HCl acid (198 μL; 3 M solution) was added, followed by seed crystals (Form I). The slurry was temperature cycled from 40 to 5° C. for 3 days. The crystalline HCl salt was isolated via vacuum filtration, air-dried for 30 min and dried in a vacuum oven at 40° C. overnight. The yield of the crystalline HCl salt was 72% (235 mg, 0.430 mmol).

DSC data showed a sharp endotherm with an onset at 296.6° C. (ΔH=136.5 J/g). TGA data showed negligible weight loss below 200° C. A weight loss of 1.6% was observed between 200° C. and 270° C. The stoichiometry of HCl salt was confirmed to be 1:1 (parent:HCl acid) by Ion Chromatography (IC). The DVS isotherm plot showed ~0.5% moisture uptake between 5-75% RH with a total uptake of 0.6% water from 5-95% RH indicating a low level of hygroscopicity. The XRPD pattern of the post DVS sample did not show a change in crystal form or crystallinity. Drying at 40° C. in a vacuum oven overnight also did not change the crystal form.

The X-ray powder diffraction (XRPD) pattern of this material (Form I) is shown in FIG. 5 and a summary of the diffraction angles and d-spacings is given in Table II below. The XRPD analysis was conducted on a PANanalytical X'Pert Pro Diffractometer on Si zero-background wafers using X'celerator™ RTMS (Real Time Multi-Strip) detector. The acquisition conditions included: Cu $K_\alpha$ radiation, generator tension: 45 kV, generator current: 40 mA, step size: 0.02° 2θ. Configuration on the incidental beam side: fixed divergence slit (0.250), 0.04 rad Soller slits, anti-scatter slit (0.250), and 10 mm beam mask. Configuration on the diffracted beam side: fixed divergence slit (0.250) and 0.04 rad Soller slit.

TABLE II

| Diff. Angle [°2θ] | d-spacing [Å] |
|---|---|
| 8.0946 | 10.9229 |
| 10.1871 | 8.6834 |
| 11.1596 | 7.9289 |
| 12.3730 | 7.1539 |
| 12.8414 | 6.8939 |
| 13.8164 | 6.4096 |
| 15.3329 | 5.7789 |
| 15.5403 | 5.7022 |
| 16.0341 | 5.5277 |
| 17.1860 | 5.1597 |
| 18.2618 | 4.8581 |
| 18.8118 | 4.7173 |
| 19.4134 | 4.5725 |
| 19.7590 | 4.4933 |
| 20.5922 | 4.3133 |
| 22.4437 | 3.9615 |
| 23.8041 | 3.7381 |
| 24.4061 | 3.6472 |
| 24.8857 | 3.5780 |
| 25.6231 | 3.4767 |
| 26.4085 | 3.3750 |
| 27.4345 | 3.2511 |
| 28.3544 | 3.1477 |
| 29.2340 | 3.0550 |
| 30.9402 | 2.8903 |
| 31.8774 | 2.8074 |
| 32.7645 | 2.7334 |
| 34.5383 | 2.5970 |
| 36.2559 | 2.4778 |
| 38.3009 | 2.3501 |

The Raman spectrum of this material (Form I) was recorded on a Nicolet NXR 9650 FT-Raman Spectrometer, at 4 cm$^{-1}$ resolution with excitation from a Nd:YVO4 laser (λ=1064 nm). The Raman spectrum of this material is shown in FIG. 6 with major peaks observed at 421.6, 435.5, 468.3, 480.1, 504.7, 511.4, 537.7, 549.9, 566.3, 611.1, 658.8, 683.1, 693.2, 728.0, 737.7, 763.9, 776.0, 793.6, 806.5, 813.7, 851.8, 886.9, 924.8, 986.3, 1000.6, 1050.4, 1115.8, 1139.6, 1169.2, 1207.2, 1226.7, 1252.1, 1276.7, 1286.1, 1312.7, 1338.0, 1372.6, 1391.4, 1427.9, 1462.4, 1482.4, 1552.7, 1595.3, 1620.0, 1646.7, 2865.0, 2921.8, 2955.3, 2973.3, and 3062.7 cm$^{-1}$.

The differential scanning calorimetry (DSC) thermogram of this material (Form II) was recorded on a TA Instruments Q100 Differential Scanning Calorimeter equipped with an autosampler and a refrigerated cooling system under 40 mL/min $N_2$ purge and is shown in FIG. 3. The experiments were conducted using a heating rate of 15° C./min in a crimped aluminum pan. The DSC thermogram of this material (Form II) exhibited a large single endotherm with an onset temperature of about 265° C., a peak temperature about 300° C., and enthalpy of 136.5 J/g. A person skilled in the art would recognize that the onset temperature, peak temperature, and enthalpy of the endotherm may vary depending on the experimental conditions.

The thermogravimetric analysis (TGA) thermogram of this material (Form II) was recorded on a TA Instruments Q500 Thermogravimetric Analyzer and is shown in FIG. 4. The experiments were conducted with 40 mL/min $N_2$ flow and a heating rate of 15° C./min. The TGA thermogram of this material (Form II) exhibited a single weight loss event observed prior to the final thermal decomposition. The weight loss event takes place in the temperature range of 30° C. to 260° C. with a weight loss of about 1.6%.

Example 11

(R)-5-((4,6-Dimethyl-2-oxo-1,2-dihydropyridin-3-yl)methyl)-3-methyl-2-(1-(1-((1-methylcyclopropyl)methyl)piperidin-4-yl)ethyl)-5,6,7,8-tetrahydro-4H-thieno[3,2-c]azepin-4-one

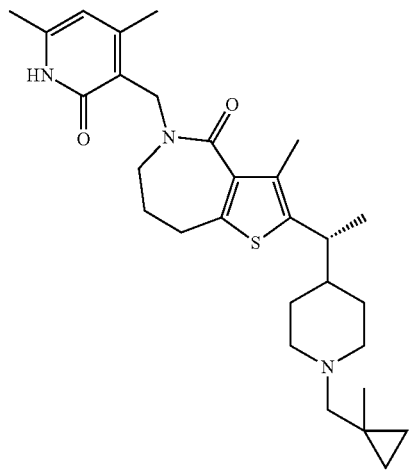 [SMILES: Cc1cc(C)c(CN2CCCc3sc([C@H](C)C4CCN(CC5(C)CC5)CC4)c(C)c3C2=O)c(=O)[nH]1]

Following the general procedure of Example 1, (R)-5-((4,6-dimethyl-2-oxo-1,2-dihydropyridin-3-yl)methyl)-3-methyl-2-(1-(1-((1-methylcyclopropyl)methyl)piperidin-4-yl)ethyl)-5,6,7,8-tetrahydro-4H-thieno[3,2-c]azepin-4-one was prepared. $^1$H NMR (DMSO-d$_6$) δ 0.11-0.33 (m, 4H) 0.98 (s, 3H) 1.07-1.28 (m, 6H) 1.39 (d, J=12.17 Hz, 1H) 1.59-1.82 (m, 5H) 1.97-2.07 (m, 2H) 2.08-2.29 (m, 9H) 2.66 (t, J=7.22 Hz, 2H) 2.81-2.92 (m, 2H) 2.97 (d, J=10.39 Hz, 1H) 3.14-3.31 (m, 2H) 4.51 (d, J=13.43 Hz, 1H) 4.60 (d, J=13.69 Hz, 1H) 5.91 (s, 1H) 11.58 (s, 1H). MS(ES) [M+H]$^+$ 496.6.

Assay Protocol

Compounds contained herein were evaluated for their ability to inhibit the methyltransferase activity of EZH2 within the PRC2 complex. Human PRC2 complex was prepared by co-expressing each of the 5 member proteins (FLAG-EZH2, EED, SUZ12, RbAp48, AEBP2) in Sf9 cells followed by co-purification. Enzyme activity was measured in a scintillation proximity assay (SPA) where a tritiated methyl group is transferred from 3H-SAM to a lysine residue on a biotinylated, unmethylated peptide substrate derived from histone H3. The peptides were captured on streptavidin-coated SPA beads and the resulting signal was read on a ViewLux plate reader.

Part A. Compound Preparation
1. Prepare 10 mM stock of compounds from solid in 100% DMSO.
2. Set up an 11-point serial dilution (1:4 dilution, top concentration 10 mM) in 100% DMSO for each test compound in a 384 well plate leaving columns 6 and 18 for DMSO controls.
3. Dispense 10 nL of compound from the dilution plate into reaction plates (Corning, 384-well polystyrene NBS, Cat #3673).

Part B. Reagent Preparation
Prepare the following solutions:
1. 1× Base Buffer, 50 mM Tris-HCl, pH 8, 2 mM $MgCl_2$: Per 1 L of base buffer, combine 1 M Tris-HCl, pH 8 (50 mL), 1 M $MgCl_2$ (2 mL), and distilled water (948 mL).
2. 1× Assay Buffer: Per 10 mL of 1× Assay Buffer, combine 1× Base Buffer (9.96 mL), 1 M DTT (40 uL), and 10% Tween-20 (1 uL) to provide a final concentration of 50 mM Tris-HCl, pH 8, 2 mM $MgCl_2$, 4 mM DTT, 0.001% Tween-20.
3. 2× Enzyme Solution: Per 10 mL of 2× Enzyme Solution, combine 1× Assay Buffer (9.99 mL) and 3.24 uM EZH2 5 member complex (6.17 uL) to provide a final enzyme concentration of 1 nM.
4. SPA Bead Solution: Per 1 mL of SPA Bead Solution, combine Streptavidin coated SPA beads (PerkinElmer, Cat # RPNQ0261, 40 mg) and 1× Assay Buffer (1 mL) to provide a working concentration of 40 mg/mL.
5. 2× Substrate Solution: Per 10 mL of 2× Substrate Solution, combine 40 mg/mL SPA Bead Solution (375 uL), 1 mM biotinylated histone H3K27 peptide (200 uL), 12.5 uM 3H-SAM (240 uL; 1 mCi/mL), 1 mM cold SAM (57 uL), and 1× Assay Buffer (9.13 mL) to provide a final concentration of 0.75 mg/mL SPA Bead Solution, 10 uM biotinylated histone H3K27 peptide, 0.15 uM 3H-SAM (~12 uCi/mL 3H-SAM), and 2.85 uM cold SAM.
6. 2.67× Quench Solution: Per 10 mL of 2.67× Quench Solution, combine 1× Assay Buffer (9.73 mL) and 10 mM cold SAM (267 uL) to provide a final concentration of 100 uM cold SAM.

Part C. Assay Reaction in 384-well Grenier Bio-One Plates
Compound Addition
1. Stamp 10 nL/well of 1000× Compound to test wells (as noted above).
2. Stamp 10 nL/well of 100% DMSO to columns 6 & 18 (high and low controls, respectively).

Assay
1. Dispense 5 uL/well of 1× Assay Buffer to column 18 (low control reactions).
2. Dispense 5 uL/well of 2× Substrate Solution to columns 1-24 (note: substrate solution should be mixed to ensure homogeneous bead suspension before dispensing into matrix reservoir).
3. Dispense 5 uL/well of 2× Enzyme Solution to columns 1-17, 19-24.
4. Incubate the reaction for 60 min at room temperature.

Quench
1. Dispense 6 uL/well of the 2.67× Quench Solution to columns 1-24.
2. Seal assay plates and spin for ~1 min at 500 rpm.
3. Dark adapt plates in the ViewLux instrument for 15-60 min.

Read Plates
1. Read the assay plates on the Viewlux Plate Reader utilizing the 613 nm emission filter or clear filter (300 s exposure).

Reagent addition can be done manually or with automated liquid handler.

Results

Percent inhibition was calculated relative to the DMSO control for each compound concentration and the resulting values were fit using standard $IC_{50}$ fitting parameters within the ABASE data fitting software package.

The exemplified compounds were generally tested according to the above or an analogous assay and were found to be inhibitors of EZH2. Specific biological activities tested according to such assays are listed in the following table. The $IC_{50}$ values of 10 nM indicate that the activity of compound was approaching the limit of detection in the assay. Repeating the assay run(s) may result in somewhat different $IC_{50}$ values.

| Example | EZH2 $IC_{50}$ (nM) |
| --- | --- |
| 1 | ≤10 |
| 2 | ≤10 |
| 3 | ≤10 |
| 4 | ≤10 |
| 5 | ≤10 |
| 6 | ≤10 |
| 7 | ≤10 |
| 8 | ≤10 |
| 9 | ≤10 |
| 10 | ≤10 |
| 11 | ≤10 |

The invention claimed is:
1. A compound according to Formula (I) or a pharmaceutically acceptable salt thereof:

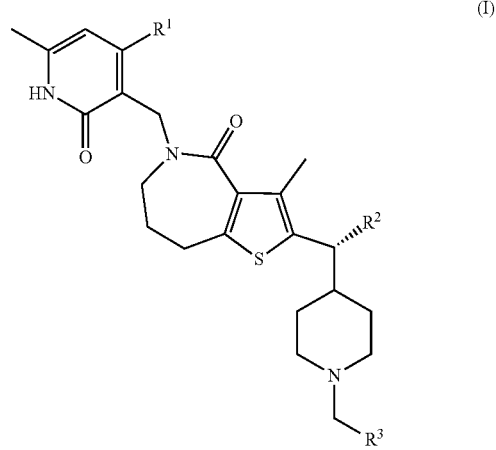

wherein:
$R^1$ is $(C_1-C_4)$alkyl or $(C_1-C_4)$alkoxy;
$R^2$ is $(C_1-C_3)$alkyl; and R³ is (C₁-C₈)alkyl, halo(C₁-C₈)alkyl, hydroxy(C₁-C₈)alkyl, (C₁-C₄)alkoxy(C₁-C₈)alkyl-, (C₃-C₅)cycloalkyl, or (C₆-C₁₀)bicycloalkyl, wherein said (C₃-C₅)cycloalkyl or (C₆-C₁₀)bicycloalkyl are each optionally substituted by one or two groups independently selected from halogen, hydroxyl, (C₁-C₄)alkoxy, (C₁-C₄)alkyl, and halo(C₁-C₄)alkyl.

2. The compound or pharmaceutically acceptable salt thereof according to claim 1, wherein R¹ is (C₁-C₄)alkyl.

3. The compound or pharmaceutically acceptable salt thereof according to claim 1, wherein R¹ is methyl, ethyl, n-propyl, or methoxy.

4. The compound or pharmaceutically acceptable salt thereof according to claim 1, wherein R¹ is methyl.

5. The compound or pharmaceutically acceptable salt thereof according to claim 1, wherein R² is methyl.

6. The compound or pharmaceutically acceptable salt thereof according to claim 1, wherein R³ is (C₁-C₆)alkyl, halo(C₁-C₆)alkyl, (C₃-C₅)cycloalkyl, or (C₆-C₁₀)bicycloalkyl, wherein said (C₃-C₅)cycloalkyl or (C₆-C₁₀)bicycloalkyl are each optionally substituted by one or two groups independently selected from halogen and (C₁-C₄)alkyl.

7. The compound or pharmaceutically acceptable salt thereof according to claim 6, wherein R³ is (C₁-C₆)alkyl or halo(C₁-C₆)alkyl.

8. The compound or pharmaceutically acceptable salt thereof according to claim 6, wherein R³ is (C₃-C₅)cycloalkyl or (C₆-C₁₀)bicycloalkyl, each of which is optionally substituted by one or two groups independently selected from halogen and (C₁-C₄)alkyl.

9. The compound or pharmaceutically acceptable salt thereof according to claim 8, wherein R³ is (C₃-C₅)cycloalkyl which is optionally substituted by fluoro or methyl.

10. The compound according to claim 1 which is:
(R)-5-((4,6-dimethyl-2-oxo-1,2-dihydropyridin-3-yl)methyl)-3-methyl-2-(1-(1-neopentylpiperidin-4-yl)ethyl)-5,6,7,8-tetrahydro-4H-thieno[3,2-c]azepin-4-one;
(R)-2-(1-(1-(cyclobutylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one;
(R)-5-((4,6-dimethyl-2-oxo-1,2-dihydropyridin-3-yl)methyl)-2-(1-(1-isobutylpiperidin-4-yl)ethyl)-3-methyl-5,6,7,8-tetrahydro-4H-thieno[3,2-c]azepin-4-one;
(R)-2-(1-(1-(cyclopentylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one;
(R)-5-((4,6-dimethyl-2-oxo-1,2-dihydropyridin-3-yl)methyl)-2-(1-(1-(2,2-dimethylbutyl)piperidin-4-yl)ethyl)-3-methyl-5,6,7,8-tetrahydro-4H-thieno[3,2-c]azepin-4-one;
(R)-5-((4,6-dimethyl-2-oxo-1,2-dihydropyridin-3-yl)methyl)-2-(1-(1-(2-fluoro-2-methylpropyl)piperidin-4-yl)ethyl)-3-methyl-5,6,7,8-tetrahydro-4H-thieno[3,2-c]azepin-4-one;
(R)-2-(1-(1-(cyclopropylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one;
(R)-5-((4,6-dimethyl-2-oxo-1,2-dihydropyridin-3-yl)methyl)-3-methyl-2-(1-(1-((1-methylcyclopentyl)methyl)piperidin-4-yl)ethyl)-5,6,7,8-tetrahydro-4H-thieno[3,2-c]azepin-4-one;
(R)-2-(1-(1-(bicyclo[2.2.2]octan-1-ylmethyl)piperidin-4-yl)ethyl)-5-((4,6-dimethyl-2-oxo-1,2-dihydropyridin-3-yl)methyl)-3-methyl-5,6,7,8-tetrahydro-4H-thieno[3,2-c]azepin-4-one;
(R)-5-((4,6-dimethyl-2-oxo-1,2-dihydropyridin-3-yl)methyl)-3-methyl-2-(1-(1-((1-methylcyclobutyl)methyl)piperidin-4-yl)ethyl)-5,6,7,8-tetrahydro-4H-thieno[3,2-c]azepin-4-one; or
(R)-5-((4,6-dimethyl-2-oxo-1,2-dihydropyridin-3-yl)methyl)-3-methyl-2-(1-(1-((1-methylcyclopropyl)methyl)piperidin-4-yl)ethyl)-5,6,7,8-tetrahydro-4H-thieno[3,2-c]azepin-4-one;
or a pharmaceutically acceptable salt thereof.

11. The compound according to claim 1 which is:

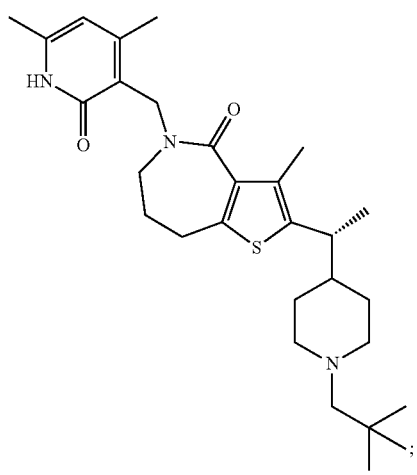 [SMILES: Cc1cc(C)c(CN2CCCc3sc([C@H](C)C4CCN(CC(C)(C)C)CC4)c(C)c3C2=O)c(=O)[nH]1]

or a pharmaceutically acceptable salt thereof.

12. The compound or pharmaceutically acceptable salt thereof according to claim 11 which is a hydrochloric acid salt.

13. The hydrochloric acid salt according to claim 12 in a crystalline form which is characterized by an X-ray powder diffraction (XRPD) pattern comprising diffraction angles, when measured using Cu K$_\alpha$ radiation, of about 8.9, 10.7, 14.3, 14.8, 16.9, and 24.0 degrees 2θ.

14. A pharmaceutical composition comprising the compound or pharmaceutically acceptable salt thereof according to claim 1 and a pharmaceutically acceptable excipient.

15. A pharmaceutical composition comprising the compound or pharmaceutically acceptable salt thereof according to claim 11 and a pharmaceutically acceptable excipient.

16. A pharmaceutical composition comprising the hydrochloric acid salt according to claim 13 and a pharmaceutically acceptable excipient.

* * * * *